United States Patent
Kitade et al.

(10) Patent No.: US 10,487,103 B2
(45) Date of Patent: Nov. 26, 2019

(54) OLIGONUCLEOTIDE DERIVATIVE, OLIGONUCLEOTIDE CONSTRUCT USING THE SAME, AND METHODS FOR PRODUCING THEM

(71) Applicant: GIFU UNIVERSITY, Gifu-shi, Gifu (JP)

(72) Inventors: Yukio Kitade, Gifu (JP); Aya Shibata, Gifu (JP)

(73) Assignee: GIFU UNIVERSITY, Gifu-Shi (JP)

( * ) Notice: Subject to any disclaimer, the term of this patent is extended or adjusted under 35 U.S.C. 154(b) by 0 days.

(21) Appl. No.: 15/560,994

(22) PCT Filed: Mar. 24, 2016

(86) PCT No.: PCT/JP2016/059398
§ 371 (c)(1),
(2) Date: Sep. 22, 2017

(87) PCT Pub. No.: WO2016/152980
PCT Pub. Date: Sep. 29, 2016

(65) Prior Publication Data
US 2018/0094017 A1 Apr. 5, 2018

(30) Foreign Application Priority Data
Mar. 24, 2015 (JP) ................. 2015-060689

(51) Int. Cl.
*C07H 13/04* (2006.01)
*C07H 21/02* (2006.01)
(Continued)

(52) U.S. Cl.
CPC ........... *C07H 19/056* (2013.01); *C07H 13/04* (2013.01); *C07H 21/02* (2013.01); *C07H 21/04* (2013.01);
(Continued)

(58) Field of Classification Search
CPC ...... C07H 19/056; C07H 13/04; C07H 21/04; C07H 21/02; C12N 15/09
See application file for complete search history.

(56) References Cited

U.S. PATENT DOCUMENTS

2009/0124571 A1 5/2009 Morvan et al.
2010/0081137 A1 4/2010 Carell et al.
(Continued)

FOREIGN PATENT DOCUMENTS

JP 2009-535323 A 10/2009
JP 2010-508015 A 3/2010
(Continued)

OTHER PUBLICATIONS

Google machine translation of JP2010195698A, https://patents.google.com/patent/JP2010195698A/en?oq=JP2010195698A, accessed online on Dec. 13, 2018. (Year: 2018).*
(Continued)

*Primary Examiner* — Jonathan S Lau
(74) *Attorney, Agent, or Firm* — Birch, Stewart, Kolasch & Birch, LLP

(57) ABSTRACT

The oligonucleotide derivative of the present invention is represented by Formula (1). This derivative is considered to be introduced into cells by binding of its amino sugar chain moiety to a ligand on cell surfaces, and have selective drug delivery function. The oligonucleotide derivative can be easily synthesized and introduced into cells without using a lipofection reagent.

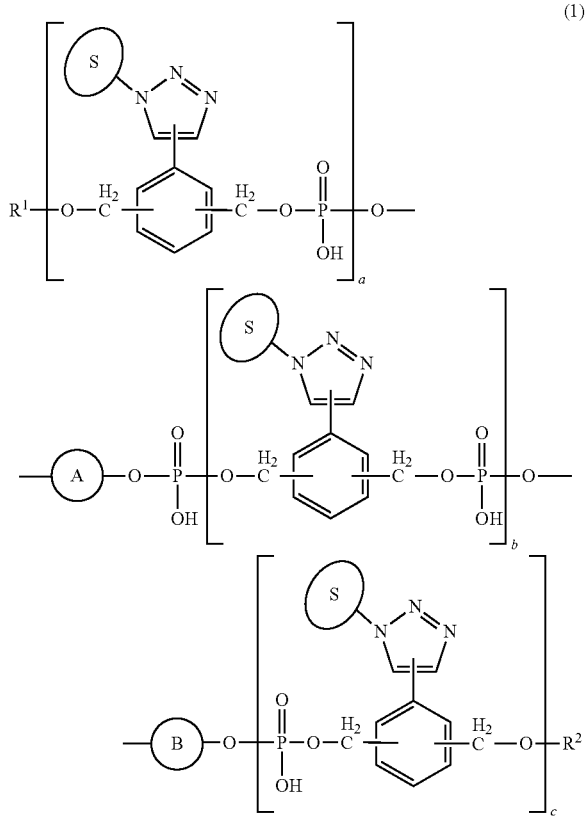

wherein A and B are independently modified or unmodified oligonucleotides whose total chain length is 3 or more, and A and B do not contain hydroxyl groups at 3' and 5' ends of the oligonucleotide; S represents a sugar substituent, a peptide chain, or a tocopherol-binding group; and an alkyl group may be bound instead of hydrogen bound to a benzene ring.

25 Claims, 13 Drawing Sheets

Specification includes a Sequence Listing.

(51) Int. Cl.
    *C07H 21/04*  (2006.01)
    *C12N 15/09*  (2006.01)
    *C07H 19/056* (2006.01)

(52) U.S. Cl.
    CPC ....... *C12N 15/09* (2013.01); *C12Q 2600/158* (2013.01)

(56) References Cited

U.S. PATENT DOCUMENTS

2010/0234282 A1  9/2010  Yokota et al.
2012/0035115 A1  2/2012  Manoharan et al.

FOREIGN PATENT DOCUMENTS

| JP | 2010-132578 A | 6/2010 |
| JP | 2010-195698 A | 9/2010 |
| JP | 2011-504874 A | 2/2011 |
| JP | 2012-513953 A | 6/2012 |
| JP | 2013-541334 A | 11/2013 |
| WO | WO 2012/037254 A1 | 3/2012 |
| WO | WO 2013/139803 A1 | 9/2013 |

OTHER PUBLICATIONS

English translation of the International Preliminary Report on Patentability (Forms PCT/IB/338 and PCT/IPEA/409), dated Sep. 28, 2017, for International Application No. PCT/JP2016/059398.

Fujimoto et al, "Synthesis of versatile fluorescent sensors based on Click chemistry: detection of unsaturated fatty acids by their pyrene-emission switching", Chemical Communications, No. 46, 2009, pp. 7164-7166.

International Preliminary Report on Patentability (PCT/IPEA/409) issued in PCT/JP2016/059398, completed on Aug. 9, 2016.

International Search Report (PCT/ISA/210) issued in PCT/JP2016/059398, dated Jun. 14, 2016.

Jouanno et al., "Kondrat'eva Ligation: Diels-Alder-Based Irreversible Reaction for Bioconjugation", The Journal of Organic Chemistry, vol. 79, No. 21, 2014, pp. 10353-10366.

Peschke et al, "Controlled coupling of peptides at their C-termini", Peptides, vol. 30, No. 4, 2009, pp. 689-698.

Written Opinion (PCT/ISA/237) issued in PCT/JP2016/059398, dated Jun. 14, 2016.

\* cited by examiner (2)

(6)

(7)

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Synthetic: antisense strand of siRNA (mixed
      DNA/RNA sequence)
<220> FEATURE:
<221> NAME/KEY: misc_feature
<222> LOCATION: (1)..(19)
<223> OTHER INFORMATION: nucleotides are RNA
<220> FEATURE:
<221> NAME/KEY: misc_feature
<222> LOCATION: (20)..(21)
<223> OTHER INFORMATION: nucleotides are DNA

<400> SEQUENCE: 1
guaggaguag ugaaaggcct t                                             21

<210> SEQ ID NO 2
<211> LENGTH: 20
<212> TYPE: DNA
<213> ORGANISM: Artificial Sequence
<220> FEATURE:
<223> OTHER INFORMATION: Synthetic: sense strand of siRNA (mixed DNA/RNA
      sequence)
<220> FEATURE:
<221> NAME/KEY: misc_feature
<222> LOCATION: (1)..(19)
<223> OTHER INFORMATION: nucleotides are RNA
<220> FEATURE:
<221> NAME/KEY: misc_feature
<222> LOCATION: (20)..(20)
<223> OTHER INFORMATION: nucleotides are DNA
<220> FEATURE:
<221> NAME/KEY: misc_feature
<222> LOCATION: (20)..(20)
<223> OTHER INFORMATION: 3' BE
```

```
<400> SEQUENCE: 2
ggccuuucac uacuccuact                                              20

<210> SEQ ID NO 3
<211> LENGTH: 19
<212> TYPE: RNA
<213> ORGANISM: Artificial Sequence
<220> FEATURE:
<223> OTHER INFORMATION: polynucleotide
<220> FEATURE:
<221> NAME/KEY: misc_feature
<222> LOCATION: (19)..(19)
<223> OTHER INFORMATION: 3' C4BE

<400> SEQUENCE: 3
ggccuuucac uacuccuac                                               19

<210> SEQ ID NO 4
<211> LENGTH: 19
<212> TYPE: RNA
<213> ORGANISM: Artificial Sequence
<220> FEATURE:
<223> OTHER INFORMATION: polynucleotide
<220> FEATURE:
<221> NAME/KEY: misc_feature
<222> LOCATION: (19)..(19)
<223> OTHER INFORMATION: 3' C4C4BE

<400> SEQUENCE: 4
ggccuuucac uacuccuac                                               19

<210> SEQ ID NO 5
<211> LENGTH: 19
<212> TYPE: RNA
<213> ORGANISM: Artificial Sequence
<220> FEATURE:
<223> OTHER INFORMATION: polynucleotide
<220> FEATURE:
<221> NAME/KEY: misc_feature
<222> LOCATION: (19)..(19)
<223> OTHER INFORMATION: 3' C4C4BGlcNAc

<400> SEQUENCE: 5
ggccuuucac uacuccuac                                               19

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Lys Pro Phe Val Tyr Leu Ile
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Cys Asp Gly Arg
1
```

```
<210> SEQ ID NO 8
<211> LENGTH: 7
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminus Azide

<400> SEQUENCE: 8

Lys Pro Phe Val Tyr Leu Ile
1               5

<210> SEQ ID NO 9
<211> LENGTH: 4
<212> TYPE: PRT
<213> ORGANISM: Artificial Sequence
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: N-terminus Azide

<400> SEQUENCE: 9

Cys Asp Gly Arg
1
```

OLIGONUCLEOTIDE DERIVATIVE, OLIGONUCLEOTIDE CONSTRUCT USING THE SAME, AND METHODS FOR PRODUCING THEM

TECHNICAL FIELD

The present invention relates to an oligonucleotide derivative, an oligonucleotide construct using the same, and methods for producing them.

BACKGROUND ART

In recent years, various oligonucleotides such as DNAs and RNAs have come to be used for treatment, diagnosis, etc. For example, specific gene knockdown techniques using RNA interference (RNAi) have attracted attention as nucleic-acid technologies. RNAi is a phenomenon in which the function of a gene is inhibited by the action of a double-stranded RNA (dsRNA) having a sequence homologous to the gene. Nucleic acid medicines using this RNAi are highly expected as next-generation therapeutic medicines.

On the other hand, studies have also been made to chemically modify oligonucleotides to impart new functions that natural forms do not have. The present inventors have also developed a technique for introducing an ethynyl group at the end of an oligonucleotide and further modifying the ethynyl group with a new substituent, such as a benzene ring, by utilizing a click reaction (Patent Literature 1). Further, it has been revealed that an artificial oligonucleotide obtained by this technique has higher nuclease resistance than a natural oligonucleotide and is less likely to be decomposed in cells.

However, a nucleic acid itself is negatively charged and cannot pass through the cell membrane. Therefore, nucleic acid medicines require a drug delivery system (DDS) that allows nucleotides to pass through the cell membrane. At present, a lipofection technique using liposomes has been developed as a technique for introducing nucleotides into cells. In this technique, a complex is formed by binding a positively-charged cationic liposome around negatively-charged DNA to allow the DNA etc. to be incorporated into cells through cell surfaces by an endocytosis phenomenon.

However, there is a problem that a lipofection reagent used in the lipofection technique is toxic to the liver and the kidney. Further, the lipofection technique is a DDS utilizing mere endocytosis, and therefore lacks in cell selectivity.

In order to solve these problems, a chemically-modified oligonucleotide has been developed which is obtained by introducing asialoglycopeptide chains at the 3' end of an oligonucleotide so as to be introduced into cells through an asialoglycoprotein receptor (ASGPR) (Patent Literatures 2 and 3). However, as shown in FIG. 4, a chemically-modified oligonucleotide obtained by this method has a complicated chemical structure having three asialoglycopeptide chains, and its synthesis requires complicated operations.

CITATIONS LIST

Patent Literatures

Patent Literature 1: JP-A-2010-195698
Patent Literature 2: WO 2012-037254
Patent Literature 3: JP-T-2013-541334

SUMMARY OF INVENTION

Technical Problems

In view of the above circumstances, it is an object of the present invention to provide a novel oligonucleotide derivative that can be easily synthesized and that can be introduced into cells without using a lipofection reagent.

Solutions to Problems

As described above, the present inventors have succeeded in introducing an ethynyl group into an oligonucleotide (Patent Literature 1). Therefore, the present inventors have tried to further bind a saccharide, a peptide chain, or a natural compound to this ethynyl group by a click reaction. This is because it is known that many receptors that recognize a specific saccharide are present on cell membrane surfaces (e.g., desmin and vimentin present on the surfaces of hepatocytes etc. are known to selectively recognize N-acetylglucosamine), and therefore drug delivery via receptors that recognize a sugar chain can be expected. The same can be expected for a peptide chain and a natural compound. As a result of intensive studies, the present inventors have found that when a saccharide, a peptide chain, or a natural compound is bound to an ethynyl group-modified oligonucleotide by a click reaction, a sugar-modified oligonucleotide derivative can be easily synthesized in good yield. Further, the present inventors have found that a siRNA modified with this oligonucleotide derivative can be introduced into cells without using a lipofection reagent. These findings have led to the completion of the present invention.

More specifically, an oligonucleotide derivative according to a first aspect of the present invention is represented by the following formula (1). Here, a saccharide substituent represented by S in the formula includes a disaccharide substituent and a polysaccharide substituent as well as a monosaccharide substituent. Further, the sugar substituent includes also an amino sugar and an amino sugar derivative having an acylated amino group.

[Chemical Formula 1]

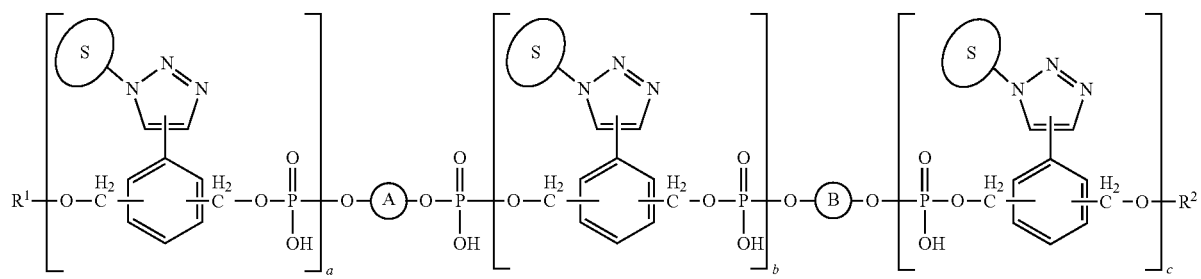

(1)

wherein $R^1$ and $R^2$ each independently represent hydrogen or a phosphate group; a, b, and c are independently integers of 0 or more, and at least one of them is 1 or more; A and B are independently modified or unmodified oligonucleotides whose total chain length is 3 or more, and A and B do not contain hydroxyl groups at 3' and 5' ends of the oligonucleotide; S represents a sugar substituent, a peptide chain, or a tocopherol-binding group; and an alkyl group may be bound instead of hydrogen bound to a benzene ring.

Further, an oligonucleotide derivative according to a second aspect of the present invention is represented by the formula (2) as shown in FIG. 6. Here, S in the formula is a sugar substituent, a peptide chain, or a tocopherol-binding group, and the sugar substituent includes a disaccharide substituent and a polysaccharide substituent as well as a monosaccharide substituent. Further, the sugar substituent includes also an amino sugar and an amino sugar derivative having an acylated amino group.

In the formula (2), $R^1$ and $R^2$ each independently represent hydrogen or a phosphate group; a, b, and c are independently integers of 0 or more, and at least one of them is 1 or more; A and B are independently modified or unmodified oligonucleotides whose total chain length is 3 or more, and A and B do not contain hydroxyl groups at 3' and 5' ends of the oligonucleotide; an alkyl group may be bound instead of hydrogen bound to a benzene ring; S represents a sugar substituent, a peptide chain, or a tocopherol-binding group; n represents a natural number of 0 to 4; LINKER represents a linker; and X represents any one of

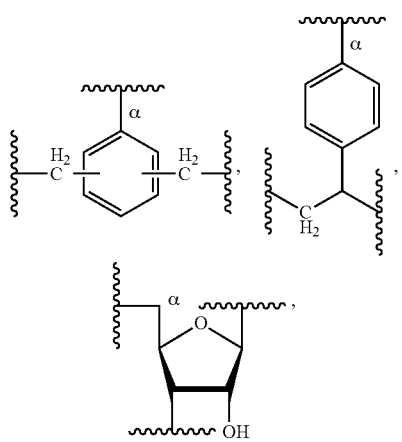

wherein carbon marked with α is bound to a triazole ring, and fluorine and/or an alkyl group may be bound instead of hydrogen bound to X.

When S in the oligonucleotide derivative according to the present invention is a sugar substituent, the sugar substituent may be one represented by the following chemical structural formula (3) or (3'):

[Chemical Formula 3]

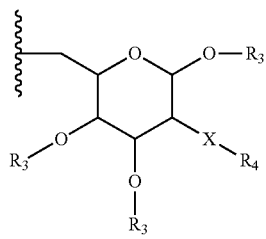

(3)

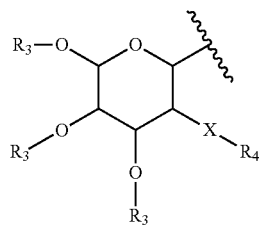

(3')

X=O or NH; and
$R_3$ and $R_4$ are each independently H, Ac, or $COCF_3$ ($R_3$=H, Ac, or $COCF_3$; $R_4$=H, Ac, or $COCF_3$).

When the sugar substituent S has an acyl group, the acyl group may be modified with a fluorine atom (e.g., a trifluoroacetyl group). When a fluorine atom is introduced into the sugar substituent, hydrophobicity can be increased. Therefore, it is considered that when a receptor on a cell membrane surface easily receives a hydrophobic functional group, permeability is increased.

An oligonucleotide derivative according to a third aspect of the present invention is represented by the formula as shown in FIG. 7.

In the formula as shown in FIG. 7, $R^1$ and $R^2$ each independently represent hydrogen or a phosphate group; a, b, and c are independently integers of 0 or more, and at least one of them is 1 or more; A and B are independently modified or unmodified oligonucleotides whose total chain length is 3 or more, and A and B do not contain hydroxyl groups at 3' and 5' ends of the oligonucleotide; an alkyl group may be bound instead of hydrogen bound to a benzene ring; LINKER represents a linker; and
X represents any one of

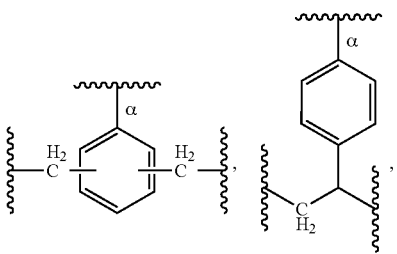

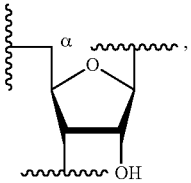

wherein carbon marked with α is bound to a triazole ring, and fluorine and/or an alkyl group may be bound instead of hydrogen bound to X.

Further, $R^1$ and $R^2$ in the oligonucleotide derivative according to the present invention may be H. Further, b may be 0. Further, both a and b may be 0. Further, c may be 1 or more and 5 or less.

Further, A and B may have a partial sequence of mRNA of a predetermined gene or its complementary sequence. In this case, RNA interference can be exerted on the mRNA, and therefore protein synthesis by the target mRNA can be inhibited.

Further, the total chain length of A and B may be 10 or more and 35 or less. Usually, siRNAs and miRNAs have lengths within this range, and can inhibit protein synthesis by their target RNA.

Further, A and B may be oligoribonucleotides.

The oligonucleotide derivative according to the present invention can be used to regulate gene expression. That is, an oligonucleotide construct according to the present invention is an oligonucleotide construct for regulating gene expression, and comprises the oligonucleotide derivative according to the present invention. Specific examples of the application of such an oligonucleotide construct for regulating gene expression include single- and double-stranded DNAs, single- and double-stranded RNAs, DNA/RNA chimeras, and DNA/RNA hybrids. Other examples of the application include antigenes, antisenses, aptamers, siRNAs, miRNAs, shRNAs, and ribozymes.

Further, the oligonucleotide construct according to the present invention may have a unit represented by the formula (4) or (5) as shown in FIGS. 8A and 8B at a dangling end.

In FIG. 8A, S represents a sugar substituent, a peptide chain, or a tocopherol-binding group; n represents a natural number of 0 to 4; LINKER represents a linker.

In FIG. 8B, carbon marked with α is bound to a triazole ring, and fluorine and/or an alkyl group may be bound instead of hydrogen bound to X.

The oligonucleotide construct according to the present invention may be a siRNA wherein in the oligonucleotide derivative, a and b are 0, c is 1 or 2, and a unit represented by the formula (4) or (5) is contained at a 3' dangling end.

The oligonucleotide derivative according to the present invention may be used as an oligonucleotide construct for genetic diagnosis. Further, this construct may be a probe.

The oligonucleotide derivative according to the present invention can be synthesized by a so-called click reaction using a compound according to the present invention represented by the formula (6) or (7) as shown in FIG. 9 and an ethynyl group-containing oligonucleotide.

In FIG. 9, S represents a sugar substituent, a peptide chain, or a tocopherol-binding group; n represents a natural number of 0 to 4; and LINKER represents a linker.

This compound can be used as a unit for chemically modifying the dangling end of a siRNA.

An oligonucleotide can be modified with one or two or more selected from the above compounds according to the present invention. Further, at least one unit represented by the formula (4) or (5) can be introduced into an oligonucleotide by any one of addition, substitution, and insertion, or a combination of two or more of them.

DESCRIPTION OF EMBODIMENTS (Oligonucleotide Derivative)

Figure 6:
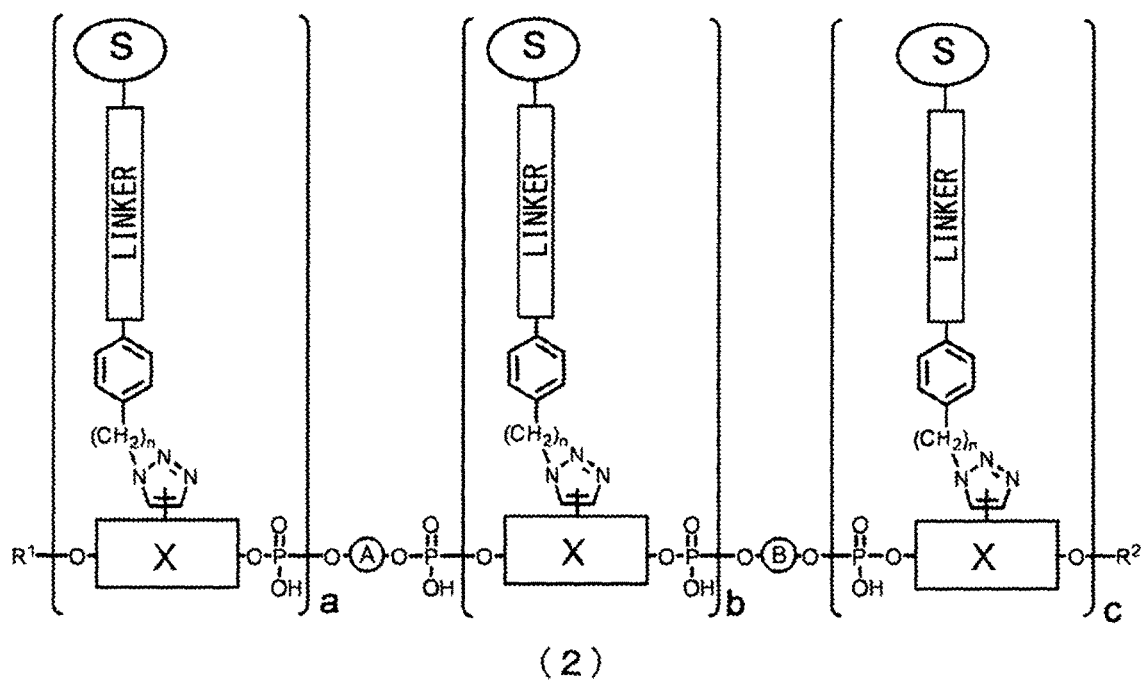
FIG. 6 shows the formula (2).
Figure 7:
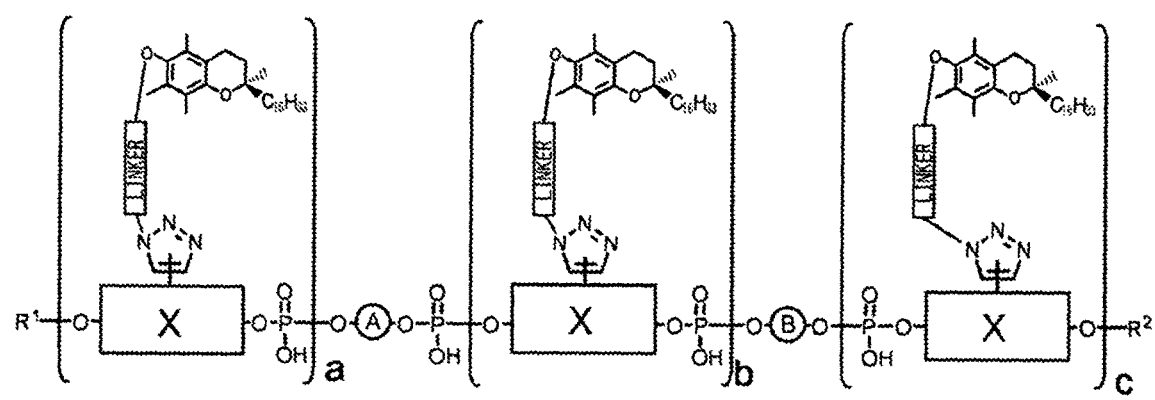
FIG. 7 shows an oligonucleotide derivative according to a third aspect of the present invention.
Figure 8A:
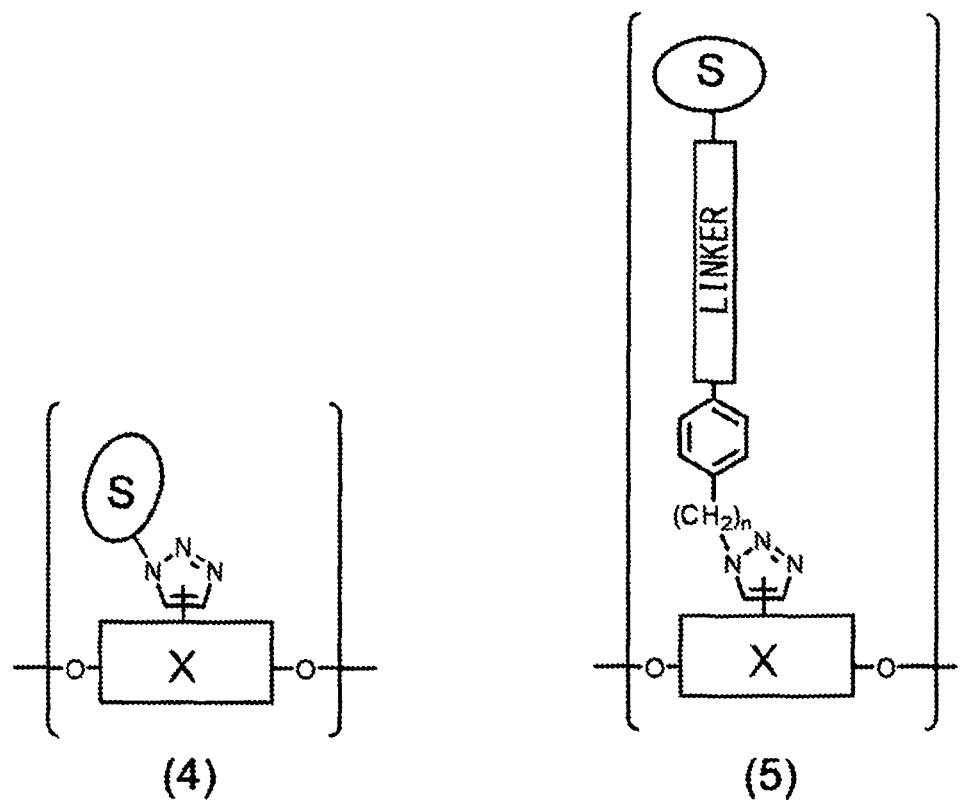
FIGS. 8A and 8b show the formulas (4) and (5).
Figure 8B:
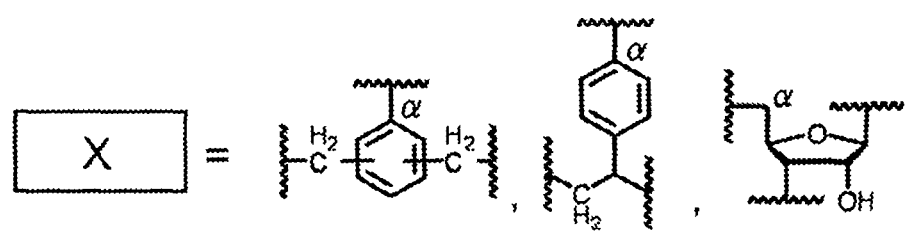

An oligonucleotide derivative according to a first aspect of the present invention is represented by the following formula (1), and an oligonucleotide derivative according to a second aspect of the present invention is represented by the formula (2) as shown in FIG. 6.

[Chemical Formula 7]

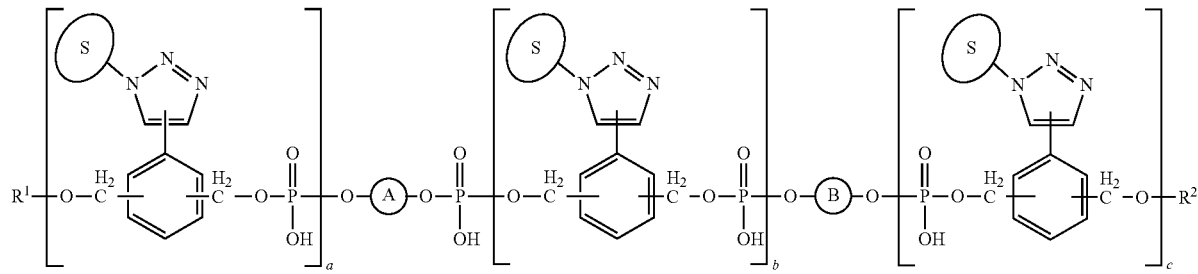

(1)

wherein R¹ and R² each independently represent hydrogen or a phosphate group; a, b, and c are independently integers of 0 or more, and at least one of them is 1 or more; A and B are independently modified or unmodified oligonucleotides whose total chain length is 3 or more, and A and B do not contain hydroxyl groups at 3' and 5' ends of the oligonucleotide; S represents a sugar substituent, a peptide chain, or a tocopherol-binding group; an alkyl group may be bound instead of hydrogen bound to a benzene ring.

In the formula (2), R¹ and R² each independently represent hydrogen or a phosphate group; a, b, and c are independently integers of 0 or more, and at least one of them is 1 or more; A and B are independently modified or unmodified oligonucleotides whose total chain length is 3 or more, and A and B do not contain hydroxyl groups at 3' and 5' ends of the oligonucleotide; an alkyl group may be bound instead of hydrogen bound to a benzene ring; S represents a sugar substituent, a peptide chain, or a tocopherol-binding group; n represents a natural number of 0 to 4; LINKER represents a linker; and X represents any one of

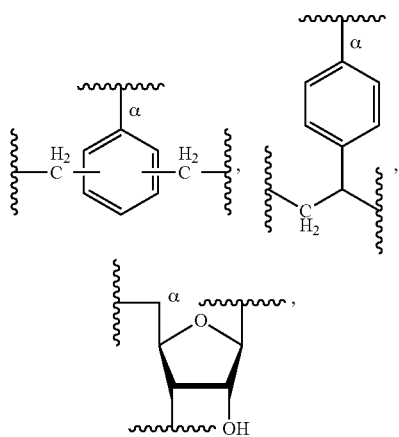

wherein carbon marked with α is bound to a triazole ring, and fluorine and/or an alkyl group may be bound instead of hydrogen bound to X.

The oligonucleotide derivative according to the first aspect of the present invention has a partial structure represented by the formula (4) at at least one of the both ends and middle of the oligonucleotide derivative. Further, the oligonucleotide derivative according to the second aspect of the present invention has a partial structure represented by the formula (5) at at least one of the both ends and middle of the oligonucleotide derivative. When such a partial structure has a sugar substituent, the oligonucleotide derivative can be introduced into cells through ligands on cell membrane surfaces, such as vimentin and an asialoglycoprotein receptor (ASGPR). Also when S is a peptide chain or a tocopherol-binding group, similar cell membrane permeability can be expected. Further, improvement in nuclease resistance can be expected due to the presence of such an artificial partial structure. Such a partial structure can be introduced into an oligonucleotide of known or unknown sequence by any one of addition, substitution, and insertion or a combination of two or more of them. It is to be noted that the term "oligonucleotide" as used herein is a concept including a modified oligonucleotide.

The sugar substituent in the above (4) and (5) is not particularly limited, and may be a monosaccharide such as glucose, fructose, galactose, mannose, fucose, glucosamine, fructosamine, galactosamine, or mannosamine, or an oligosaccharide of dimer or higher oligomer such as sucrose, lactose, or maltose. Further, the sugar substituent may be an amino sugar or an amino sugar in which an acyl group has been bound to an amino group. In this case, a fluorine element may be bound to the acyl group.

Further, the linker in the (5) is not particularly limited as long as it is a linker that can be adapted to a sugar substituent, a peptide chain, or a hydroxyl group of tocopherol. Examples of the linker will be shown below (in the formulas, n is a natural number). The linker increases the degree of freedom of movement of a sugar substituent or a peptide chain. Therefore, it can be considered that the introduction of the linker makes it easy to bind a sugar substituent or a peptide chain to a ligand (receptor) on the cell membrane.

[Chemical Formula 10]

Examples of the linker used when S is a sugar substituent

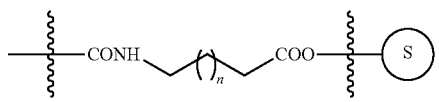
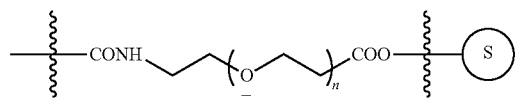

-continued

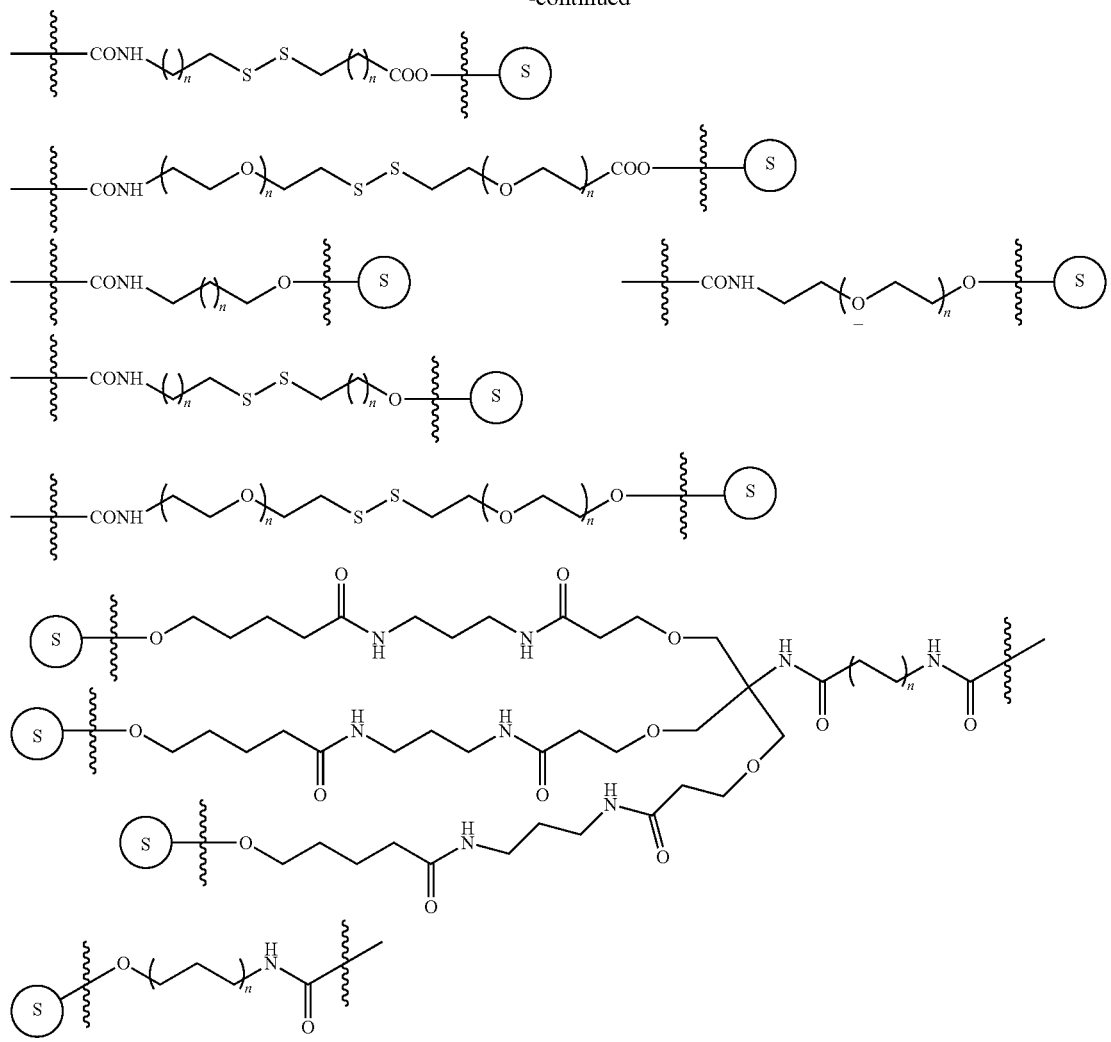

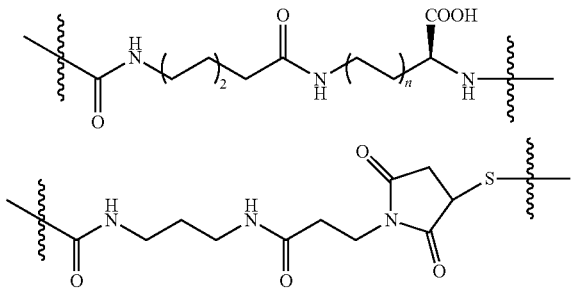

(A linker that binds to the sulfur element of cystine)

In the partial structures represented by the above formulas (4) and (5), two "—CH₂O—" groups and a triazole ring on a benzene ring may be bound to any positions on the benzene ring. Further, an alkyl group may be bound instead of hydrogen directly bound to the benzene ring. Examples of the alkyl group include alkyl groups having 1 to 4 carbon atoms. Specific examples of such an alkyl group include a methyl group, an ethyl group, a n-propyl group, a n-butyl group, an isobutyl group, and a tert-butyl group.

Further, when this partial structure (4) or (5) is provided at the 5' end of an oligonucleotide, resistance to exonuclease that acts on the 5' end is effectively imparted. On the other hand, when provided at the 3' end of an oligonucleotide, this partial structure (4) or (5) is effective for exonuclease that acts on the 3' end, and is effective for improving the silencing effect of RNAi. Therefore, for example, when resistance to nuclease that acts on the 3' end needs to be improved, a and b may be 0. On the other hand, when resistance to nuclease that acts on the 5' end needs to be improved, b and c may be 0. Further, when nuclease resistance needs to be achieved, a, b, and c shall each be at least 1, but a, b, and c may each be 2 or more, or a total of any two of a, b, and c may be 2 or more.

Further, when this partial structure (4) or (5) is provided at a site other than the both ends of an oligonucleotide, endonuclease resistance can be effectively imparted to a site other than the 3' and 5' ends of the oligonucleotide.

Further, the number and positions of the partial structures (4) or (5) in the oligonucleotide derivative according to the present invention are determined in consideration of nuclease resistance and the effect of introduction of the partial Examples of the linker used when S is a peptide chain structure (4) or (5) on the oligonucleotide derivative. For example, when a siRNA or a shRNA is constructed using the oligonucleotide derivative according to the present invention, a and b may be 0, and 1 to 3 (c=1 to 3), preferably 1 or 2 (c=1, 2) partial structures (U) may be added to the 3' end of a 3' dangling end nucleotide (e.g., dT (deoxythymidine)) of such a construct, or one or both of, for example, two dT nucleotides of a siRNA may be replaced with the partial structures (4) or (5) (c=1, 2). Further, the partial structure (4) or (5) may be inserted at the 3' dangling end. The mode in which an existing nucleotide is replaced with the partial structure (4) or (5) has an advantage that the chain length of a siRNA is not increased.

Further, when an anti-gene, an antisense, an aptamer, a miRNA, or a ribozyme is constructed using the oligonucleotide derivative according to the present invention, the partial structure (4) or (5) may be appropriately provided, if necessary. For example, in the case of an antisense RNA, the partial structures (4) or (5) can be formed on the 3' and 5' end sides. Further, in the case of an aptamer or a ribozyme, the partial structure (4) or (5) provided at a site other than the 5' and 3' ends may be effective. Further, in the case of a probe, the partial structure (4) or (5) may be provided on one or both of the 3' and 5' end sides.

In the oligonucleotide derivative according to the present invention, A and B are each independently modified or unmodified oligonucleotides, and may be the same or different. The term "oligonucleotide" as used herein refers to a polymer having nucleotides, which are monomers generally constituting an oligonucleotide or a polynucleotide, as monomer units. Further, the term "nucleotide" refers to a deoxyribonucleotide and/or a ribonucleotide as a monomer unit. In general, a polymer having deoxyribonucleotides, which are nucleotides, as monomer units is referred to as DNA, and a polymer having ribonucleotides, which are nucleotides, as monomer units is referred to as RNA. However, the oligonucleotide derivative according to the present invention includes not only so-called DNAs and RNAs but also oligomers of monomer units thereof. Further, the oligonucleotide includes also RNA/DNA chimeras. Further, the modified or unmodified oligonucleotide includes not only oligonucleotides made of only nucleotides containing natural bases such as guanine, cytosine, thymine, adenine, uracil, and methyl cytosine that are purines and pyrimidines but also oligonucleotides having one or two or more nucleotides chemically modified at any of the base moiety, sugar moiety, and phosphate moiety thereof.

In the oligonucleotide derivative according to the present invention, each of the base sequence of the oligonucleotide A and the base sequence of the oligonucleotide B or a combination of them may have a partial sequence of sense or antisense strand of DNA or mRNA of a predetermined gene or a complementary sequence thereof. Such complementarity allows hybridization with a target nucleic acid of any kind, which makes it possible to allow the oligonucleotide derivative to fulfill its intended function. In the oligonucleotide derivative according to the present invention, the length of A and B is not particularly limited, and can be set according to the intended use. However, in consideration of the ease of synthesis of an oligonucleotide and the fulfillment of an expected effect, the length of A and B is preferably 10 or more and 35 or less. Further, in the case of an antisense, the length of A and B may be about 10 or more and 30 or less. In the case of a siRNA, the total chain length of A and B is preferably 15 or more and 35 or less, more preferably 30 or less. Further, in the case of a primer, the total chain length of A and B is 10 or more and 30 or less, and in the case of a probe, the total chain length of A and B is preferably 10 or more and 30 or less.

When the oligonucleotide derivative according to the present invention is used for, for example, a siRNA, an shRNA, an antisense, a ribozyme, or an aptamer, the monomer units of A and B may be modified or unmodified oligoribonucleotides.

(Oligonucleotide Construct)

An oligonucleotide construct according to the present invention has one or two or more kinds of the oligonucleotide derivatives according to the present invention. Depending on the type of the oligonucleotide derivative or the combination of the oligonucleotide derivatives in the oligonucleotide construct, the oligonucleotide construct may have a single form of single-stranded DNA, double-stranded DNA, single-stranded RNA, double-stranded RNA, DMA/RNA chimera, or DNA/RNA hybrid or a combination form of two or more of them. As has been described above, since the oligonucleotide moiety constituting the oligonucleotide derivative includes a modified oligonucleotide, the oligonucleotide construct may contain a modified oligonucleotide.

The oligonucleotide construct having any of such forms preferably has the partial structure (4) or (5) at a site that may be a target of nuclease. These partial structures can be provided at a terminal mismatch or dangling end. Considering exonuclease resistance, the partial structure (4) or (5) is preferably provided at a dangling end. Further, the partial structure (4) or (5) can be provided in a bulge, mismatch internal loop, hair pin loop, or the like.

The oligonucleotide construct according to the present invention has improved nuclease resistance, and therefore can be used for various applications such as regulation of gene expression, research, and diagnosis. Examples of the application of the oligonucleotide construct for regulating gene expression include anti-genes, antisenses, aptamers, siRNAs, miRNAs, shRNAs, and ribozymes. In particular, in the case of siRNAs and shRNAs, both nuclease resistance and silencing activity can be improved by substitutionally or additionally introducing the partial structure (4) or (5) into dT at a 3' overhang end.

Figure 1:
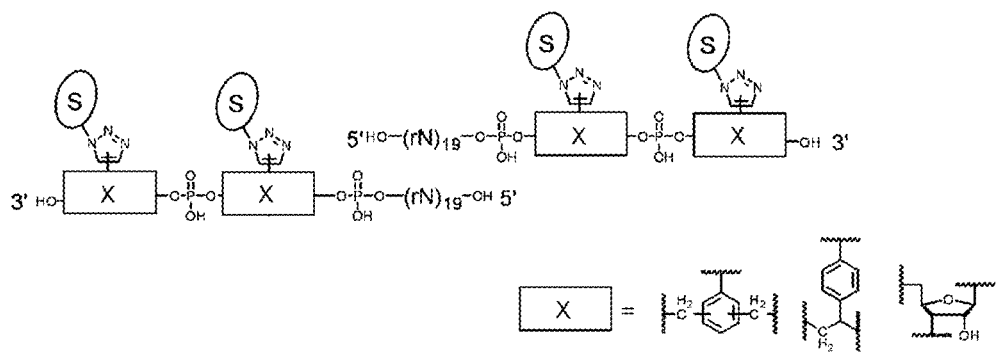
FIG. 1 is a diagram showing an example of a siRNA having partial structures (4) at its 3' ends.

FIG. 1 shows an example of a siRNA having the partial structures (4) at its 3' ends. Further, an example of the oligonucleotide construct for diagnosis or research includes a probe. A probe is an oligonucleotide that has a sequence specific to a target nucleic acid defined by design or selection and that is obtained so as to hybridize with the target nucleic acid under predetermined stringency conditions. A probe constructed using the oligonucleotide derivative has enhanced nuclease resistance, and therefore the effect of nuclease contained in a sample containing a target nucleic acid can be reduced or avoided. Therefore, a sample can be prepared even when nuclease is poorly removed or nuclease removal treatment is omitted. As a result, a genetic diagnosis or examination can be performed easily.

(Method for Producing Oligonucleotide Derivative)

Figure 9:
FIG. 9 shows the formulas (6) and (7).
Figure 9:
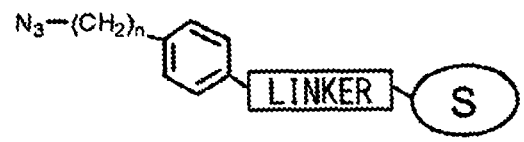

A compound represented by a formula (6) or (7) as shown in FIG. 9 is a compound preferably used for producing the oligonucleotide derivative according to the present invention:

In FIG. 9, S represents a sugar substituent, a peptide chain, or a tocopherol-binding group; n represents a natural number of 0 to 4; and LINKER represents a linker.

(Method for Producing Oligonucleotide Derivative)

An oligonucleotide having an ethynyl group can be obtained by a conventionally-known nucleic acid synthesis method. Then, a click reaction with the compound (6) or (7)

according to the present invention is appropriately performed. In this way, the oligonucleotide derivative according to the present invention can be produced.

For example, an oligonucleotide derivative having the partial structure (4) or (5) at its 5' end can be obtained by introducing the partial structure (4) or (5) into an oligonucleotide having an ethynyl group at its 5' end obtained by a conventional nucleic acid synthesis method by a click reaction with the compound (6) and (7). Further, the two or more partial structures (4) or (5) may be continuously introduced by performing a click reaction with an oligonucleotide having continuous ethynyl groups at its 5' end. In this way, an oligonucleotide derivative having one or two or more partial structures (4) or (5) on its 5' end side can be obtained.

Further, an oligonucleotide derivative having a unit of the partial structure (4) or (5) on its 3' end side can be obtained by a click reaction between an oligonucleotide having an ethynyl group at its 5' end obtained by a conventional nucleic acid synthesis method and the compound (6) or (7). Further, an oligonucleotide derivative having the partial structure (4) or (5) at a site other than its 3' and 5' ends can be obtained by a click reaction between an oligonucleotide having an ethynyl group at a site other than its 3' and 5' ends and the compound (6) or (7) according to the present invention.

(Method for Modifying Oligonucleotide)

An oligonucleotide can be modified by introducing at least one partial structure (4) or (5) into an oligonucleotide of known or unknown sequence by any of addition, substitution, and insertion or a combination of two or more of them. Such modification makes it possible to obtain an RNA construct having high silencing effect in addition to nuclease resistance. The introduction of the partial structure (4) or (5) may be performed in accordance with the method for producing an oligonucleotide derivative.

(Use of Oligonucleotide Derivative)

The oligonucleotide derivative according to the present invention can be used as a gene expression inhibitor when constructed so as to function as a siRNA, an antisense, or the like. Further, the oligonucleotide derivative according to the present invention can be used as an active ingredient of a pharmaceutical composition for preventing or treating a disease in humans and non-human animals. For example, the oligonucleotide derivative according to the present invention constructed as a gene expression inhibitor is effective for preventing or treating a disease associated with gene expression.

Further, the oligonucleotide derivative according to the present invention can be used as a test reagent or a diagnostic reagent such as a probe when constructed so as to fulfill its hybridization function. Further, such an oligonucleotide construct can be supported by a solid carrier such as a chip or beads so as to be used as an inspection device, a diagnostic device, or a part thereof. Further, such a test reagent or diagnostic reagent can also be used in combination with another reagent or diagnostic reagent or another device to provide a test or diagnostic kit.

The oligonucleotide derivative according to the present invention can also be used for a gene expression inhibition method utilizing the gene expression inhibitory action of an oligonucleotide construct comprising the oligonucleotide derivative according to the present invention. Further, the oligonucleotide derivative according to the present invention can also be used for a gene detection method utilizing the hybridization function of the oligonucleotide construct according to the present invention.

EXAMPLES

Hereinbelow, examples of the present invention will be specifically described in detail.

(Preparation of Amidited CPG Resin)

A compound 6 as an amidited nucleotide derivative and a compound 8 as a CPG resin were synthesized through a synthetic route shown in the following schemes I and II. More specifically, the amino group of dimethyl 5-aminoisophthalate 1 was iodinated to obtain a compound 2 in a yield of 55%, and then an iodine group was converted to trimethylsilylacetylene to obtain a compound 3 in a yield of 95%. Further, reduction and detrimethylsilylation were performed to obtain a compound 4 in a yield of 70%.

Scheme I

[Chemical Formula 12]

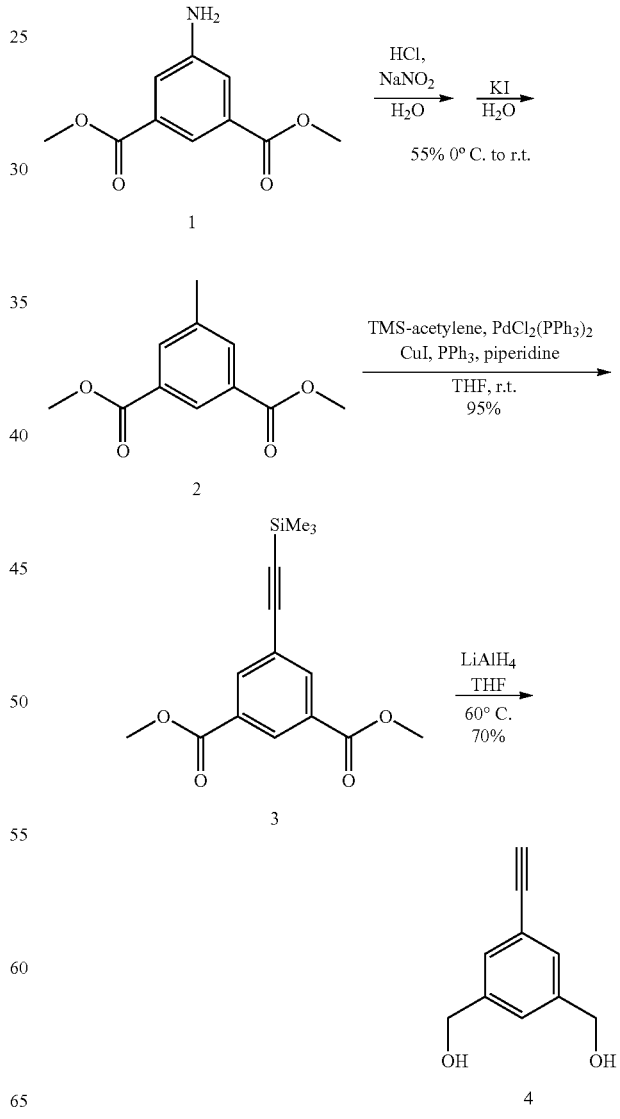

The thus obtained compound 4 was modified with 4,4'-dimethoxytrityl chloride (DMTrCl) as shown in Scheme II to obtain a compound 5 in a yield of 49%, and the compound 5 was further amidited to obtain a compound 6 in a yield of 38%. Further, the compound 5 was succinylated, and then a CPG resin was modified therewith to obtain a compound 8 with an activity of 48.9 µmol/g.

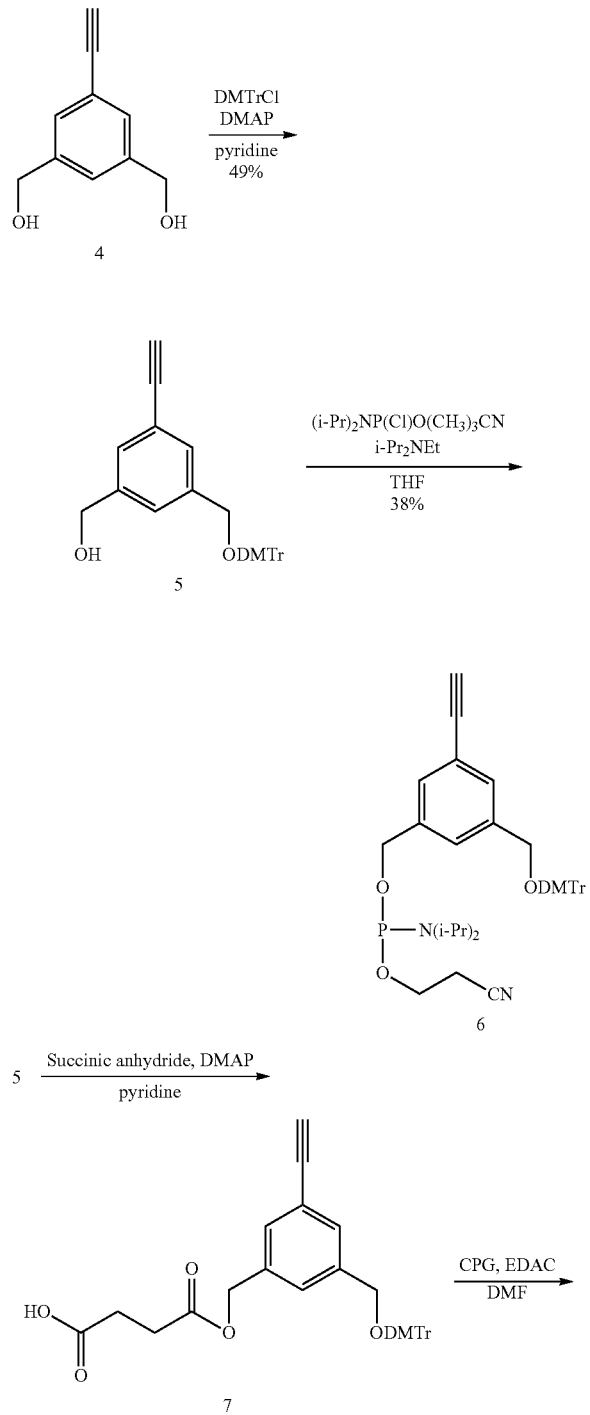

48.9 µmol/g
EDAC: 1-Ethyl,3-(3-dimethylaminopropyl)carbodimide, hydrochloride

Hereinafter, each of the steps in Scheme I and Scheme II will be described in detail.

Synthesis of Dimethyl 5-iodoisophthalate (2)

Under an Ar atmosphere, dimethyl 5-aminoisophthalate (1) (6.27 g, 30.0 mmol) was added to 39 mL of hydrochloric acid (2 M) cooled with ice. After the mixture was stirred at 0° C. or less for several minutes, 21.6 mL of an aqueous solution of $NaNO_2$ (2.52 g, 36.5 mmol, 1.2 eq.) cooled with ice was added dropwise. Further, 30 mL of dichloromethane was added, and the mixture was stirred for 5 hours after reaching room temperature. Then, 70 mL of an aqueous solution of KI (7.47 g, 45.0 mmol, 1.5 eq.) was added dropwise with ice cooling, and the mixture was stirred at room temperature for 12 hours. After the completion of the stirring, the aqueous layer was subjected to extraction with EtOAc, and the organic layer was washed with brine, dried over magnesium sulfate, and then subjected to silica gel chromatography ($SiO_2$, hexane) to isolate a compound 2 (5.285 g, 16.5 mmol, 55%).

$^1$H-NMR (400 MHz, $CDCl_3$) δ; 8.62 (t, 1H, J=1.4 Hz), 8.53 (s, 2H, J=1.4 Hz), 3.94 (s, 6H).

$^{13}$C-NMR (100 MHz, $CDCl_3$) d 165.2 (2C), 142.9 (2C), 132.6 (2C), 130.2, 93.8, 53.1 (2C), MS (EI) m/z 320 ($M^+$), HRMS Calcd for $C_{10}H_9IO_4$: 319.9546. Found: 319.9553. Anal. Calcd for $C_{10}H_9IO_4$: C, 37.52; H, 2.83. Found: C, 37.44; H, 2.86.

Synthesis of Dimethyl 5-trimethylsilylisophthalate (3)

Under an argon atmosphere, the compound 2 (96.0 mg, 0.3 mmol), bis(triphenylphosphine)palladium dichloride (16.8 mg, 4 mol %), cuprous iodide (4.6 mg, 8 mol %), and triphenylphosphine (11.8 mg, 15 mol %) were subjected to freeze-pump-thaw cycles for three times. Further, trimethylsilyl acetylene (83.9 µL, 2.0 eq) and piperidine (0.5 mL, 16.8 eq) were dissolved in THF (5 mL). Then, the solution was subjected to freeze-pump-thaw cycles for three times and then mixed with the compound 2 (96.0 mg, 0.3 mmol), bis(triphenylphosphine)palladium dichloride (16.8 mg, 4 mol %), cuprous iodide (4.6 mg, 8 mol %), and triphenylphosphine that had been subjected to freeze-pump-thaw cycles, and the mixture was stirred at room temperature for 12 hours. Then, the solvent was distilled off under reduced pressure. Then, the residue was subjected to extraction with chloroform, and the organic layer was washed with a saturated ammonium chloride solution, dried over sodium sulfate, and subjected to silica gel chromatography (SiO$_2$, hexane/EtOAc=100:1) to isolate a compound 3 (82.7 mg, 95%).

H-NMR (400 MHz, CDCl$_3$) δ; 8.60 (t, 1H, J=1.7 Hz), 8.29 (d, 2H, J=1.7 Hz), 3.95 (s, 6H). 0.26 (s, 9H) $^{13}$C-NMR (100 MHz, CDCl$_3$) d 165.8 (2C), 137.1 (2C), 131.0 (2C), 130.5, 124.4, 102.9, 96.9, 52.7 (2C), 0.0 (2C), MS (EI) m/z 290 (M$^+$), HRMS Calcd for C$_{15}$H$_{18}$O$_4$Si: 290.0974 Found: 290.0979. Anal. Calcd for C$_{15}$H$_{18}$O$_4$Si: C, 62.04; H, 6.25. Found: C, 62.86; H, 6.23.

Synthesis of 5-ethynyl-1,3-benzenedimethanol (4)

Under an Ar atmosphere, the compound 3 (6.64 g, 22.9 mmol) was dissolved in THF (100 mL), lithium aluminum hydride (2.60 g, 68.5 mmol, 3.0 eq) was added at room temperature, and the temperature of the mixture was raised to 60° C. and stirred for 12 hours. The reaction was quenched with a NaHCO$_3$ solution. Then, extraction with EtOAc was performed, and the organic layer was washed with brine, dried over sodium sulfate, and then subjected to silica gel chromatography (neutral SiO$_2$, hexane/EtOAc=2:1) to isolate a compound 4 (2.26 g, 69%, 13.9 mmol).

H-NMR (400 MHz, CDCl$_3$) δ; 7.43 (s, 2H), 7.38 (s, 1H), 4.70 (d, 4H, J=6.0 Hz), 3.08 (s, 1H), 1.68 (t, 2H, J=6.0 Hz)$^{13}$C-NMR (100 MHz, CDCl$_3$) d 1601 (2C), 129.6 (2C), 125.7 (2C), 122.5, 83.3, 77.2, 64.6 (2C), MS (EI) m/z 162 (M$^+$), HRMS Calcd for C$_{10}$H$_{10}$O$_2$: 162.0681 Found: 162.0685. Anal. Calcd for C$_{10}$H$_{10}$O$_2$: C, 74.06; H, 6.21. Found: C, 73.83; H, 6.19.

Synthesis of 1-(4,4'-dimethoxytrityloxymethyl)-5-ethnyl-3-benzenemethanol (5)

Under an Ar atmosphere, the compound 4 (649.0 mg, 2.45 mmol) and DMTrCl (1.6 g, 4.72 mmol, 1.92 mmol) were stirred in pyridine (20 mL) at room temperature for 12 hours. A NaHCO$_3$ solution was added to quench the reaction. After extraction with EtOAc, the organic layer was washed with brine, dried over sodium sulfate, and then subjected to silica gel chromatography (neutral SiO$_2$, hexane/EtOAc=2:1) to isolate a compound 5 (941.4 mg, 50%, 1.25 mmol).

$^1$H-NMR (400 MHz, CDCl$_3$) δ; 7.54-7.22 (m, 12H), 6.84 (d, 4H, J=9.0 Hz), 4.65 (s, 2H), 4.18 (s, 2H), 3.79 (s, 6H) 3.09 (s, 1H), 1.82 (s, 1H) $^{13}$C-NMR (100 MHz, CD$_3$OD) d 160.1 (2C), 146.5, 143.3, 141.1, 137.3 (2C), 131.2 (4C), 130.3, 130.1, 129.2 (2C), 128.8 (2C), 127.8, 127.0, 123.7, 114.1 (4C), 87.9, 84.5, 78.5, 66.3, 64.6, 55.7 (2C), MS (FAB$^+$) m/z 646 (M$^+$), HRMS Calcd for C$_{31}$H$_{28}$O$_4$: 464.5516 Found: no date. Anal. Calcd for C$_{31}$H$_{28}$O$_4$: C, 80.15; H, 6.08. Found: C, 79.16; H, 6.35.

Synthesis of 1-[[(2-cyanoethoxy)(N,N-diisopropylamino)phosphinyloxymethyl]-3-(4,4'-dimethoxytyloxymethyl)-5-ethynylbenzene (6)

In a glove bag under an Ar atmosphere, the compound 5 (646 mg, 1.0 mmol) was dissolved in THF (5.0 mL), N,N-diisopropylethylamine (0.86 mL, 5.0 mmol, 5.0 eq.) was added, and chloro(2-cyanoethoxy)(N,N-diisopropylamino)phosphine (0.44 mL, 2.0 mmol, 2.0 eq.) was further added dropwise. After the mixture was stirred at room temperature for 1 hour, the reaction was quenched with a NaHCO$_3$ solution. Then, extraction with chloroform was performed, and the organic layer was washed with a NaHCO$_3$ solution, dried over sodium sulfate, and then subjected to silica gel chromatography (neutral SiO$_2$, hexane/EtOAc=1:1) to give a compound 6 (252.7 mg, 37%).

$^{31}$P NMR (162 MHz, CDCl$_3$) δ 149.3.

Production Example of CPG Resin (8) of 5-Ethynyl-1,3-Benzenedimethanol Derivative The compound 5 (674.9 mg, 1.45 mmol), succinic anhydride (580.8 mg, 5.80 mmol), and DMAP (1.91 mg, 0.017 mmol) were dissolved in pyridine (3.9 mL), the solution was stirred at room temperature under an Ar atmosphere for 72 hours, CHCl$_3$ and H$_2$O were added, and the organic layer was washed with H$_2$O and brine, dried over sodium sulfate, distilled under reduced pressure, and vacuum-dried. The thus obtained compound 7, aminopropyl controlled pore glass (837.5 mg, 77 µmol), and 1-ethyl-3-(3-dimethylaminopropyl)carbodiimide hydrochloride (720 mg, 3.76 mmol) were added to DMF (15 mL), and the mixture was stirred at room temperature for 72 hours. After washing the CPG resin with pyridine, a capping solution (8 mL, 0.1 MDMAP in pyridine:Ac$_2$O (9:1, v/v)) was added. After stirring for 16 hours at room temperature, the CPG resin was washed with pyridine, EtOH, and MeCN and then vacuum-dried to obtain a compound 8 as a chemically-modified CPG resin with an activity of 48.9 µmol/g. The activity was determined by placing 6 mg of this CPG resin on a glass filter, pouring a solution of HClO$_4$: EtOH (3:2, v/v) to obtain a filtrate, and measuring the absorbance of the filtrate at a UV wavelength of 498 nm (wavelength of DMTr group).

Synthesis of 1,3,4-tri-O-acetyl-2-acetamido-6-azido-β-D-glucopyranose (9)

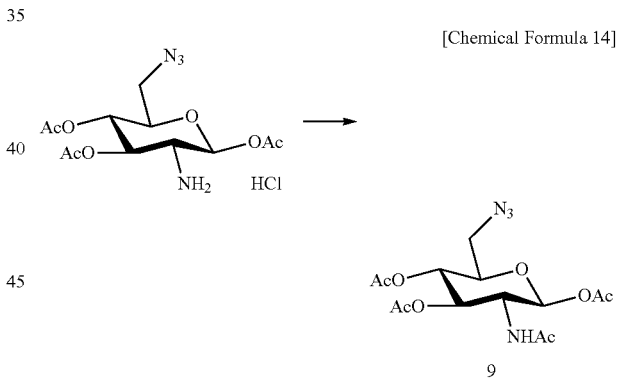

[Chemical Formula 14]

A compound 9 represented by the above formula was synthesized as a compound for constructing an amino sugar moiety having an acylated amino group in the oligonucleotide derivative according to the present invention. The details will be described below.

First, 2-amino-1,3,4-O-acetyl-6-azido-β-D-glucopyranose hydrochloride (134 mg, 0.4 mmol) was dissolved in dichloromethane (dehydrated) (4 mL), and triethylamine (224 µL, 1.6 mmol) and acetic anhydride (454 µL) were added thereto in an ice bath. Then, the ice bath was removed, and the mixture was stirred. It is to be noted that the azide compound as a raw material was prepared by a method described in J. Morel, Helv. Chim. Acta, 1958, 41, 1501-1504; S. Ogawa, H. Fujimori, T. Suami, Bull. Soc. Chim. Jpn., 1976, 49, 2585-2586. The disappearance of the raw material was confirmed by TLC after 18 hours. The reaction was quenched by adding methanol, and the solvent was distilled off under reduced pressure. Then, the residue was dissolved in ethyl acetate, and the solution was washed with 1 N hydrochloric acid, a saturated aqueous sodium hydrogen carbonate solution, and brine, and then dried by adding anhydrous sodium sulfate. Then, the mixture was filtered and distilled under reduced pressure to obtain a compound 9 as a white crystal (134 mg, 0.4 mmol, 97%).

$^1$H-NMR (400 MHz, CDCl$_3$) δ: 5.68 (d, 1H, J=8.4 Hz), 5.56 (d, 1H, J=8.4 Hz), 5.43 (t, 1H, J=9.8 Hz), 5.04 (t, 1H, J=9.8 Hz), 4.26 (q, 1H, J=9.6 Hz), 3.75 (m, 1H), 3.39-3.34 (m, 2H), 2.10 (s, 3H), 2.04 (s, 3H), 2.03 (s, 3H), 1.91 (s, 3H).

<Huisgen Reaction (Click Reaction)>

Before the synthesis of the oligonucleotide derivative according to the present invention, Huisgen reaction (click reaction) between the above-described compound 9 and compound 4 was performed as a model reaction. As a result, it was confirmed that a compound 10 having a 1,2,3-triazole ring was obtained. On the other hand, the same reaction was performed with the unacylated amino sugar derivative hydrochloride used as a raw material of the compound 9, but Huisgen reaction (click reaction) did not occur

[Chemical Formula 15]

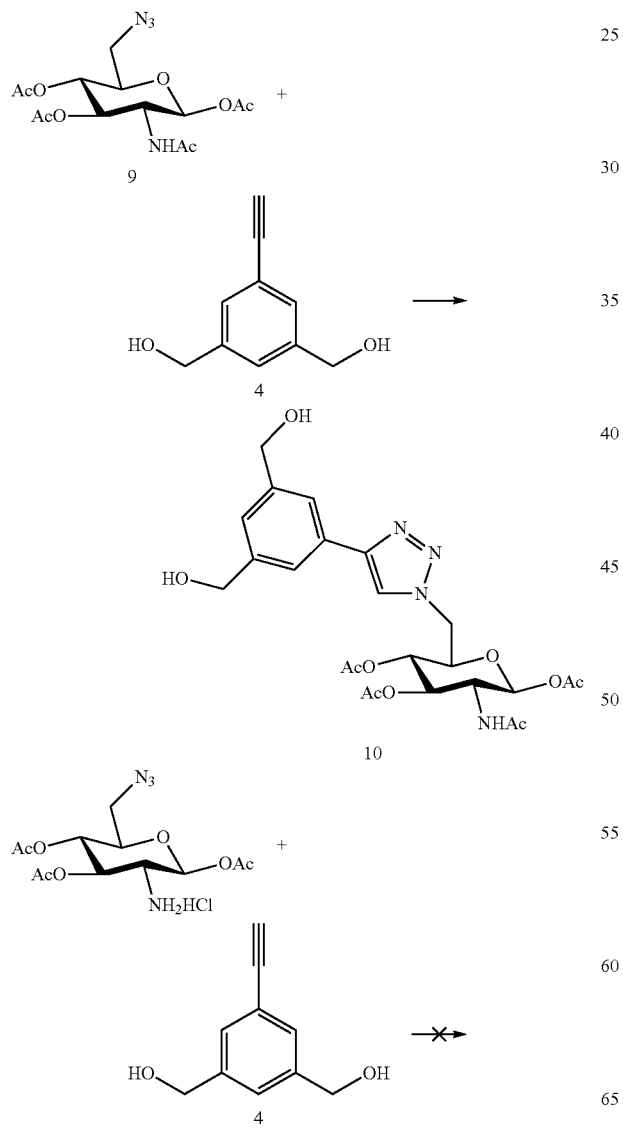

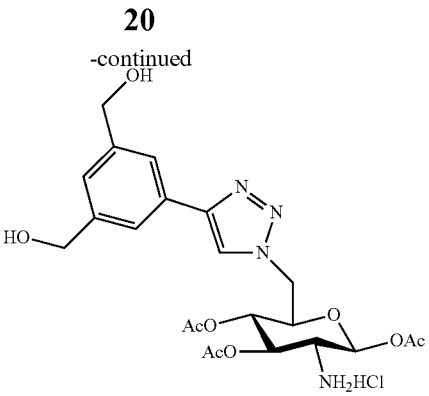

Synthesis of 1-[1,3,4-tri-O-acetyl-2-N-acetyl-β-D-glucopyranose]-4-[3,5-bis(hydroxymethyl)phenyl]-1H-1,2,3-triazole (10)

First, 5-ethynyl-1,3-benzenedimethanol (4) (100 mM solution in DMSO, 2 μL, 0.2 μmol), the compound 1 (100 mM solution in DMSO, 2 μL, 0.2 μmol), copper sulfate pentahydrate (1 M solution in Milli-Q water, 2 μL, 2 μmol), sodium ascorbate (1 M solution in Milli-Q water, 2 μL, 2 μmol), acetonitrile (4 μL), 1 M phosphate buffer (pH 7.0) (4 μL), and Milli-Q water (24 μL) were added to an Eppendorf tube and stirred for 1 second by a vortex mixer, and the mixture was allowed to stand at room temperature for 15 minutes. After lyophilization, the structure of the compound 10 was confirmed by MALDI-TOF/Ms. MALDI-TOF/Ms ([M+H]$^+$); Calculated For C$_{20}$H$_{30}$N$_4$NaO$_{10}$: 557.2, Found: 557.0.

<Preparation of Amidite>

An amidite 13 was prepared from a compound 11 via a trityl 12 through the following synthetic route.

[Chemical Formula 16]

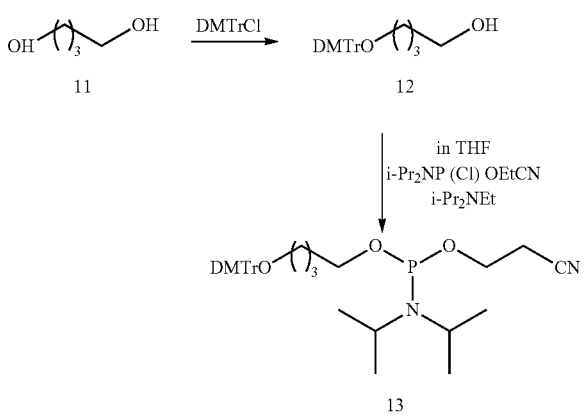

(Synthesis of Trityl 12)

A compound 11 shown in the above synthetic route was used as a starting material, and one of the hydroxyl groups was 4,4'-dimethoxytrityl-protected with DMTrCl to obtain a trityl 12. The details will be described below.

First, 30 mL of dry pyridine was added to dissolve 1.00 g of well-dried DMTrCl therein, and 3 equivalents of butanediol (compound 11, 0.79 mL) were added thereto, and the mixture was stirred at room temperature for 3 hours. Then, the reaction solution was subjected to liquid-liquid extraction with ethyl acetate and distilled water, and the organic layer was washed with saturated $NaHCO_3$ aq. and saturated NaCl aq. and dried by adding anhydrous $Na_2SO_4$. The solvent was distilled off under reduced pressure, and then the residue was purified by neutral silica gel chromatography (hexane:EtOAc=3:1) to isolate and obtain a desired compound 12 (0.90 g, 77%).

1H NMR (400 MHz, $CDCl_3$) δ [ppm];

7.44~7.20 (9H, m), 6.82 (4H, d, J=7.6 z), 3.79 (6H, s), 3.64 (2H, s), 3.11 (2H, s), 1.68 (4H, s)

Synthesis of Compound 13

The hydroxyl group of the trityl 12 was phosphitylated to obtain an amidite 13. The operation was performed in a glove bag under completely anhydrous conditions.

The compound 12 (0.172 g) vacuum-dried overnight was dissolved in dry THF, and DIPEA (3 equivalents) and a phosphitylation reagent (1.5 equivalents) were added. Then, the mixture was taken out of the glove bag and stirred at room temperature for 0.5 to 1 hour. The disappearance of the raw material was confirmed by TLC (hexane:EtOAc=2:1). Then, extraction was performed using $CHCl_3$ and saturated $NaHCO_3$ aq, and the organic layer was washed with saturated NaCl aq and dried by adding anhydrous $Na_2SO_4$. The solvent was distilled off under reduced pressure, and then the residue was purified by neutral silica gel chromatography (hexane:EtOAc=3:1) to isolate and obtain an amidite 13 (1.09 g, 88%).

31P NMR (160 MHz, CDCl3)[ppm]: 147.92

Synthesis of siRNAs

Various siRNAs shown in Table 1 were synthesized by the following procedures. (This sequence targets *Renilla* Luciferase). In the table, AS denotes a common antisense strand, and S1, S2, S3, and S3-GlcNAc denote sense strands. Further, in the sequences shown in the table, the upper-case letters denote DNA, and the lower-case letters denote RNA. The structures of the 3' ends of the sequences are shown below.

TABLE 1

| Oligonucleotide | Sequence (5'-3') | [M − H]⁻ Calculated | Found |
|---|---|---|---|
| AS | guaggaguagugaaaggccTT | 6809.0 | 6808.5 |
| S1 | ggccuuucacuacuccuacTB$^E$ | 6748.9 | 6749.5 |
| S2 | ggccuuucacuacuccuacC$_4$B$^E$ | 6596.9 | 6597.2 |
| S3 | ggccuuucacuacuccuacC$_4$C$_4$B$^E$ | 6748.9 | 6749.1 |
| S3-GlcNAc | ggccuuucacuacuccuacC$_4$C$_4$B$^{GlcNAc}$ | 6791.0 | 6791.6 |

TABLE 1-continued

| Oligonucleotide | Sequence (5'-3') | [M − H]⁻ Calculated | Found |
|---|---|---|---|

[Chemical Formula 17]

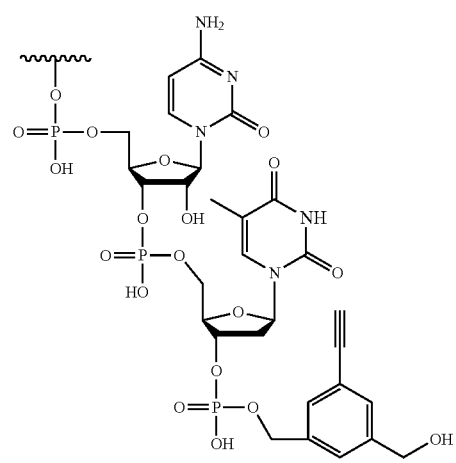

S1: ggccuuucacuacuccuacTB$^E$

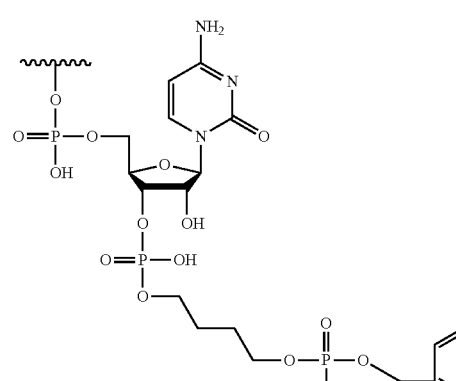

S2: ggccuuucacuacuccuacC$_4$B$^E$

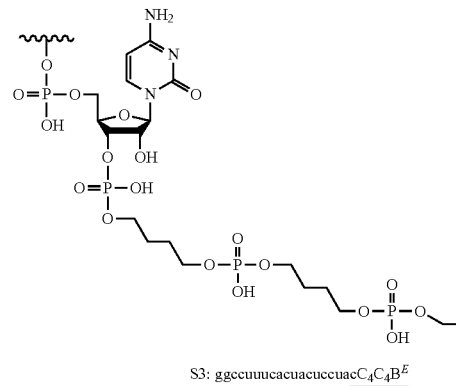

S3: ggccuuucacuacuccuacC$_4$B$^E$

TABLE 1-continued

| Oligonucleotide | Sequence (5'-3') | [M − H]⁻ | |
|---|---|---|---|
| | | Calculated | Found |

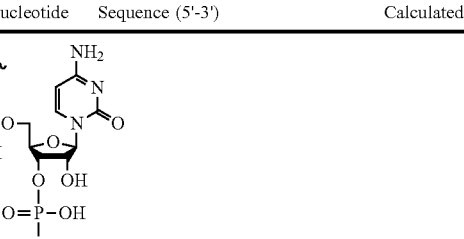

S3-GlcNAc: ggccuuucacuacuccuacC₄C₄B^(GlcNAc)

Synthesis of AS

AS was synthesized using a DNA automatic synthesizer (ABI 3400 DNA Synthesizer; Applied Biosystems) on a scale of 1 μmol of a dT-modified solid-phase carrier (Glen Research). First, dT-CE Phosphoramidite (Glen Research) and RNA Phosphoramidite (Sigma-Aldrich) were prepared in a 0.1 M acetonitrile solution. The coupling time of the phosphoramidites was set to 20 minutes. The synthesis was terminated in a state where a DMTr group was removed. The cleavage of AS from the solid-phase carrier and deprotection were performed in accordance with standard methods. The residue after drying under reduced pressure was purified by 20% denatured PAGE. The band of the AS was excised and shaken overnight in a gel elution buffer (0.1 N TEAA (pH 7.0), 1 mM EDTA). The AS was recovered from the gel elution buffer using a Sep-Pak (trademark) tC₁₈ reversed phase column. The structure of the purified AS was confirmed by MALDI-TOF/Ms (AXIMA-CFR plus; Shimadzu Corporation).

Synthesis of S1

Synthesis of S1 was performed using 1 μmol of the solid-phase carrier compound 8. The other conditions and the structure confirmation method are the same as those used in the synthesis of AS.

Synthesis of S2

Synthesis of S2 was performed using 1 μmol of the solid-phase carrier compound 8. The compound 13 was prepared and used as a 0.15 M acetonitrile solution. The other conditions and the structure confirmation method are the same as those used in the synthesis of AS.

Synthesis of S3

Synthesis of S3 was performed using 1 μmol of the solid-phase carrier compound 8. The compound 13 was prepared and used as a 0.15 M acetonitrile solution. The other conditions and the structure confirmation method are the same as those used in the synthesis of AS.

Synthesis of S3-GlcNAc

The S3 (2 mM solution in H₂O, 1 μL, 2 nmol), 1,3,4-tri-O-acetyl-2-acetamido-6-azido-β-D-glucopyranose (9) (10 mM solution in DMSO, 3 μL, 30 nmol), and acetonitrile (2.2 μL) were added to sterilized 1 M phosphate buffer (pH 7.0) (2.2 μL) and sterilized water (9.6 μL) in an Eppendorf tube, and were stirred for 1 minute by a vortex mixer. Then, sodium ascorbate (100 mM solution in H₂O, 2 μL, 200 nmol) and copper sulfate pentahydrate (100 mM solution in H₂O, 2 μL, 200 nmol) were added in order, and the mixture was stirred for 1 minute by a vortex mixer and allowed to stand at room temperature for 15 minutes. Purification was performed by HPLC to obtain a desired product (S3-GlcNAc).

<Evaluation of Ability to Inhibit Gene Expression by Dual-Luciferase Reporter Assay>

Each of the antisense strand AS and the sense strand S3-GlcNAc synthesized in such a manner as described above was transferred to an Eppendorf tube in an amount of 210 pmol, dried, and dissolved in siRNA buffer (GE Dharmacon) (100 μL), and the solution was heated at 100° C. for 5 minutes and then allowed to stand for 1 hour or more to form a double strand. Each of the 2.1 μM samples was diluted 10-fold and 100-fold to prepare samples for assay.

Further, a siRNA (having TT as dangling end nucleotides in both strands) was synthesized from the antisense strand AS and a sense strand complementary to the antisense strand AS by the same method and used as a control.

HeLa cells (provided from NIH) were suspended in OPTI-MEM at 4000 cells/45 μL on the day before introduction of siRNA, and then 0.1 μg/μL psi-CHECK (registered trademark)-2 vector (Promega) (18 μL), TransFast (registered trademark) Transfection Reagent (Promega) (27 μL), Opti-MEM (registered trademark) (Life Technologies) (315 μL) were added. Then, 50 μL of the cell suspension was placed in each well of a 96 well plate and incubated at 37° C. for 1 hour. Then, 15% BS in DMEM (100 μL) was added, and the cell suspension was cultured for 24 hours.

Introduction of siRNA was performed by two methods, one of which used a transfection reagent and the other of which did not. That is, when a transfection reagent was used, siRNA was transfected in different amounts into cells using OPTI-MEM and TransFast. When a transfection reagent was not used, siRNA was mixed in different amounts with DMEM, and the mixture was added to the cells. After 4 hours, 10% BS in DMEM (100 μL) was added, and the cells were cultured for 48 hours.

After the 48-hour cultivation, the medium was sucked out, and the cells were frozen at −80° C. On the next day, the ability to inhibit gene expression was evaluated using Dual-Glo (registered trademark) Luciferase Assay System (Promega). The evaluation was made in accordance with protocols provided by Promega.

Figure 2:
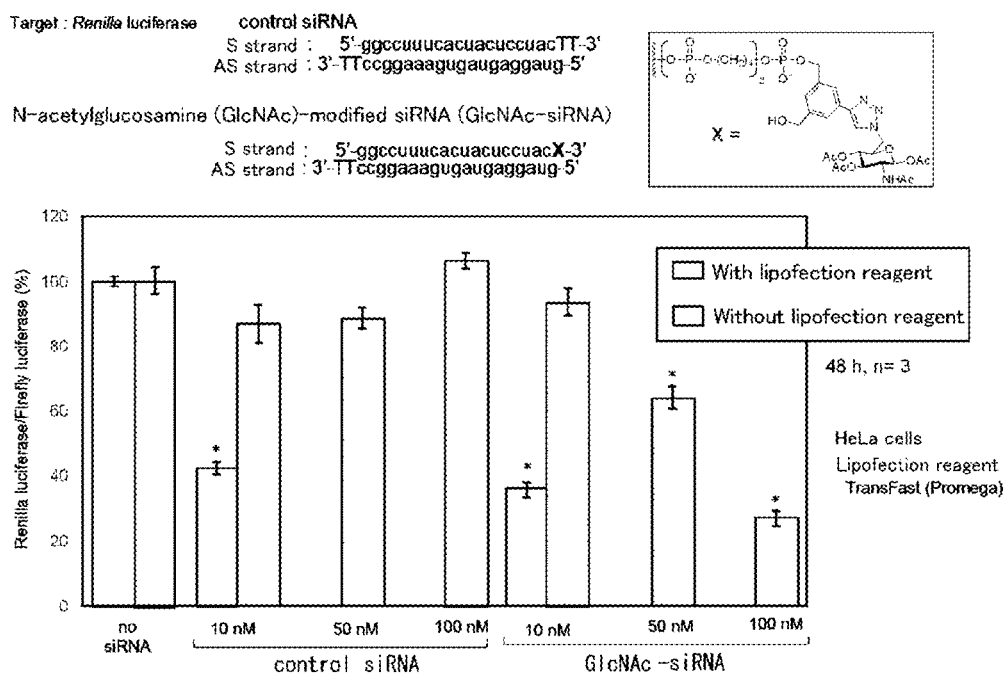
FIG. 2 is a graph showing the results of evaluation of the ability to inhibit gene expression by Dual-Luciferase reporter assay.

The results are shown in FIG. 2.

When a lipofection reagent was not used, the activity of Luciferase was reduced as the amount of the siRNA, having S3-GluNAc as a sense strand, added was increased from 10 nM to 50 nM and 100 nM. From the result, it was revealed that the siRNA fulfilled the function of silencing a gene associated with Luciferase. However, in the case of the control siRNA whose sense strand had TT as its dangling end nucleotides, the activity of Luciferase was not reduced even when the amount of the control siRNA added was increased from 10 nM to 50 nM and 100 nM, and therefore the siRNA did not fulfill the function of silencing a gene associated with Luciferase.

On the other hand, when a lipofection reagent was used, both the siRNAs fulfilled the function of silencing a gene associated with Luciferase.

Figure 3:
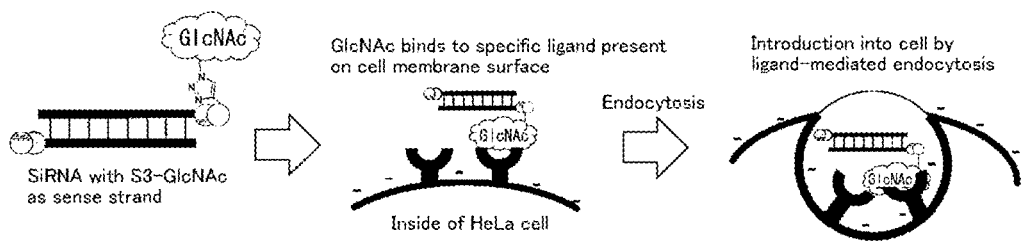
FIG. 3 is a schematic diagram showing that a siRNA selectively binds to a ligand and is selectively delivered into a cell.
Figure 4:
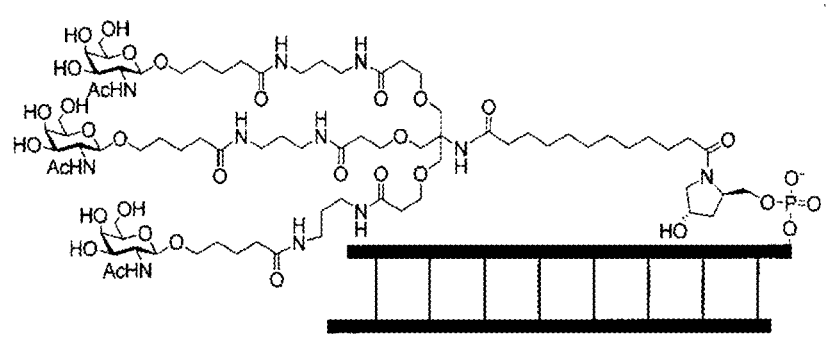
FIG. 4 is a molecular formula of a chemically-modified oligonucleotide described in Patent Literature 2 which is obtained by introducing asialoglycopeptide chains at the 3' end of an oligonucleotide.

The above results are interpreted as follows. That is, as shown in FIG. 3, the siRNA having S3-GlcNAc as a sense strand binds to a specific ligand that is present on the cell membrane surfaces of HeLa cells and that recognizes an amino sugar chain, and is introduced into the cells by endocytosis mediated by this ligand. This indicates the possibility that a siRNA using the oligonucleotide derivative according to the present invention selectively binds to a ligand and is selectively delivered into cells. Further, it is considered that such a delivery system can be applied not only to siRNAs but also to anti-genes, antisenses, aptamers, miRNAs, shRNAs, and the like.

<Oligonucleotide Derivative Obtained by Introducing Trifluoroacetyl Group>

In the oligonucleotide derivative according to the present invention, an amino sugar substituent S having a trifluoroacetylated amino group (see the following partial structure b) may be used instead of an amino sugar substituent S having an acetylated amino group (see the following partial structure a).

[Chemical Formula 18]

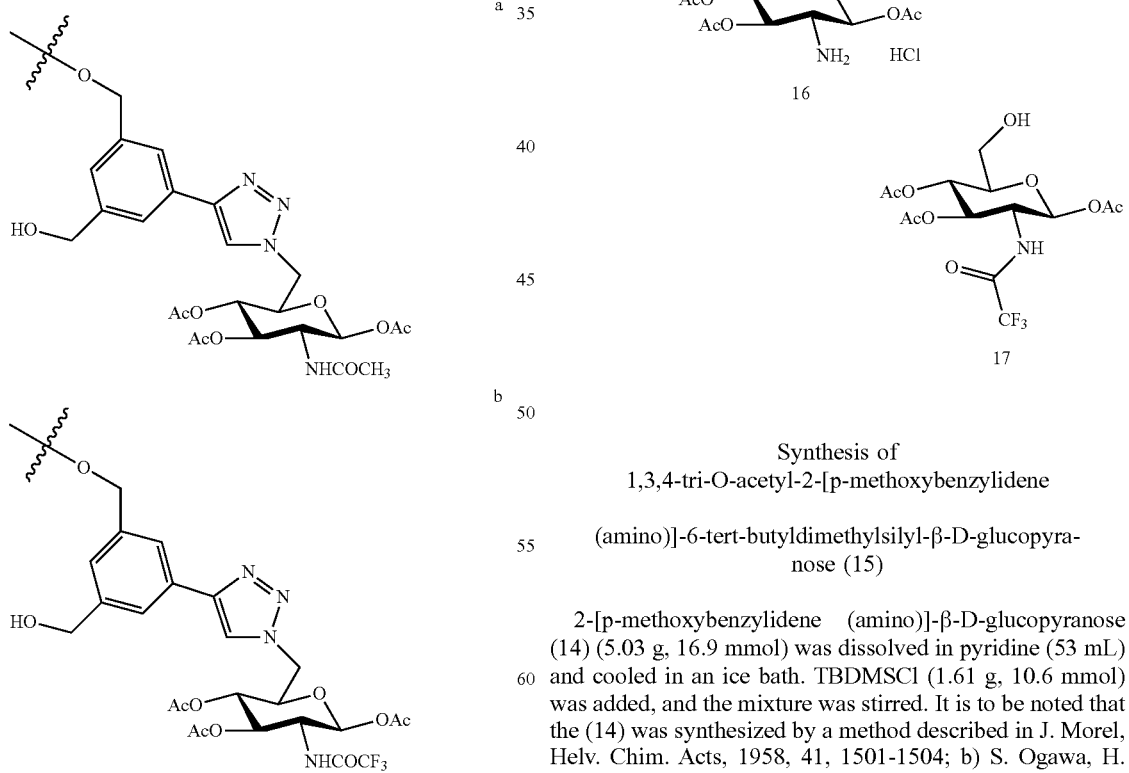

A trifluoroacetylglucosamine derivative 17 was synthesized through the following synthetic route.

[Chemical Formula 19]

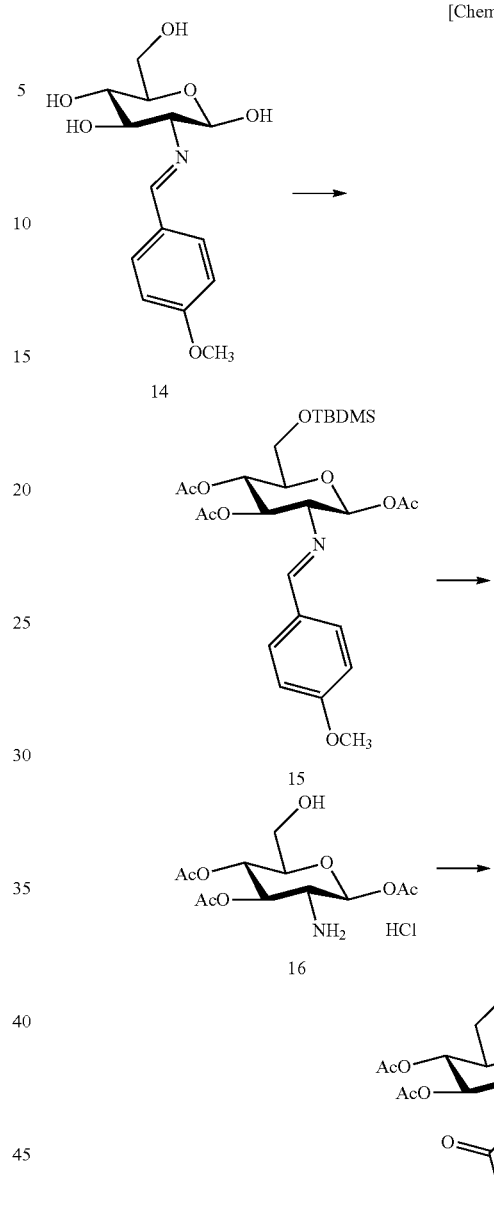

Synthesis of 1,3,4-tri-O-acetyl-2-[p-methoxybenzylidene (amino)]-6-tert-butyldimethylsilyl-β-D-glucopyranose (15)

2-[p-methoxybenzylidene (amino)]-β-D-glucopyranose (14) (5.03 g, 16.9 mmol) was dissolved in pyridine (53 mL) and cooled in an ice bath. TBDMSCl (1.61 g, 10.6 mmol) was added, and the mixture was stirred. It is to be noted that the (14) was synthesized by a method described in J. Morel, Helv. Chim. Acts, 1958, 41, 1501-1504; b) S. Ogawa, H. Fujimori, T. Suami, Bull. Soc. Chim. Jpn., 1976, 49, 2585-2586. The disappearance of the raw material was confirmed by TLC after 8 hours. Acetic anhydride (7.6 mL) was added, and the temperature of the mixture was raised to room temperature and stirred. The disappearance of the intermediate product was confirmed by TLC after 20 hours. After extraction with ethyl acetate and distilled water, the organic layer was washed with brine, dried over anhydrous sodium sulfate, and distilled under reduced pressure. Then, the residue was purified by silica gel column chromatography (hexane/ethyl acetate=5/1, 1% triethylamine) to obtain a compound 15 as a yellow crystal (4.73 g, 7.7 mmol, 48%).

$^1$H-NMR (400 MHz, CDCl$_3$) δ: 8.13 (s, 1H), 7.63 (d, 2H, J=8.8 Hz), 6.89 (d, 2H, J=8.8 Hz), 5.90 (d, 1H, J=8.8 Hz), 5.38 (t, 1H, J=9.6 Hz), 3.76 (d, 2H, J=8.8 Hz), 3.71 (q, 1H, J=7.2 Hz), 3.38 (t, 1H, J=9.6 Hz), 2.02 (s, 3H), 2.00 (s, 3H), 1.98 (s, 3H), 1.85 (s, 3H), 0.87 (s, 9H), 0.01 (d, 6H, J=8.0 Hz). HRMS (ESI, m/z, [M+Na]$^+$); Calculated For C$_{26}$H$_{39}$NNaO$_9$Si: 560.22918, Found: 560.22084.

Synthesis of 1,3,4-tri-O-acetyl-β-D-glucopyranose Hydrochloride (16)

The compound 15 (260 mg, 0.56 mmol) was dissolved in acetone (0.95 mL), and the solution was warmed in a water bath at 40° C. Then, 5 N hydrochloric acid (149.00 μL) was added, and the mixture was stirred. After 45 minutes, the disappearance of the compound 15 was confirmed by TLC. The precipitate was collected by suction filtration and washed with 1,4-dioxane to obtain a compound 16 as a white crystal (123 mg, 0.36 mmol, 65%).

$^1$H-NMR (400 MHz, DMSO-d$_6$) δ: 8.68 (s, 2H), 5.88 (d, 1H, J=8 Hz), 5.30 (t, 1H, J=10 Hz), 4.85 (t, 1H, J=10 Hz), 3.97-3.93 (m, 1H), 3.55-3.44 (m, 2H), 3.40 (d, 1H, J=8 Hz), 2.13 (s, 3H), 1.99 (s, 31H), 1.95 (s, 3H). HRMS (ESI, m/z, [M+Na]$^+$); Calculated For C$_{12}$H$_{19}$NNaO$_8$: 328.10084, Found: 328.09630.

Synthesis of 1,3,4-tri-O-acetyl-2-N-trifluoroacetyl-β-D-glucopyranose (17)

The compound 16 (686 mg, 2.24 mmol) was dissolved in pyridine (6.8 mL), and the solution was stirred in an ice bath. Then, trifluoroacetic anhydride was added, the ice bath was removed, and the mixture was stirred. The disappearance of the compound 16 was confirmed by TLC after 6 hours. After extraction with chloroform and distilled water, the organic layer was washed with brine, dried over anhydrous sodium sulfate, and distilled under reduced pressure. Then, the residue was purified by silica gel column chromatography (hexane/ethyl acetate=5/1-1/1) to obtain a compound 17 as a white crystal (739 mg, 1.84 mmol, 82%).

$^1$H-NMR (400 MHz, DMSO-d$_6$) δ: 8.12 (d, 1H, J=5.2 Hz), 7.66 (d, 1H, J=5.2 Hz), 5.87 (t, 1H, J=4.0 Hz), 5.32 (t, 1H, J=5.4 Hz), 4.93 (t, 1H), 4.08 (q, 1H, J=5.4 Hz), 3.92 (s, 1H), 3.55-3.47 (m, 1H), 2.12 (s, 3H), 1.98 (s, 3H), 1.93 (s, 3H). HRMS (ESI, m/z, [M+Na]$^+$); Calculated For C$_{14}$H$_{18}$F$_3$NNaO$_9$: 424.08313, Found: 424.08165.

Further, a trifluoroacetylglucosamine derivative 19 having an azide group and a thiophenol group was synthesized through the following synthetic mute.

[Chemical Formula 20]

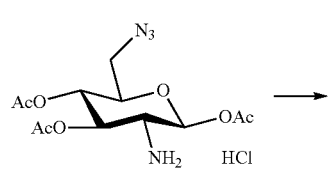

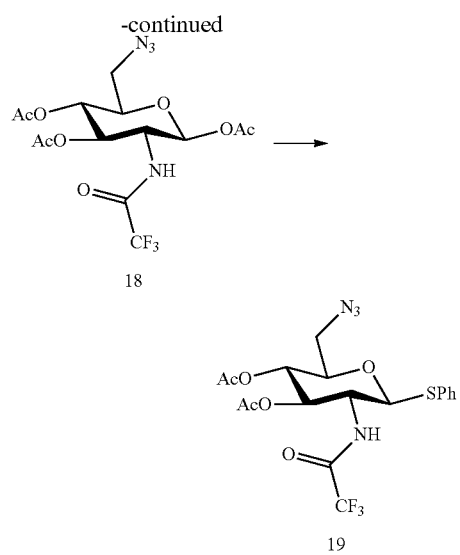

Synthesis of 1,3,4-tri-O-acetyl-2-N-trifluoroacetyl-6-azido-β-D-glucopyranose (18)

2-amino-1,3,4-O-acetyl-6-azido-β-D-glucopyranose hydrochloride (250 mg, 0.8 mmol), dichloromethane (dehydrated) (7.5 mL), pyridine (1.2 mL, 7.6 mmol), and trifluoroacetic anhydride (175.0 μL, 0.9 mmol) were added, and the mixture was stirred. The disappearance of the raw material was confirmed by TLC after 4 hours. Distilled water was added to quench the reaction. After extraction with chloroform and distilled water, the organic layer was washed with brine, dried over anhydrous sodium sulfate, and distilled under reduced pressure. Then, the residue was purified by silica gel column chromatography (hexane/ethyl acetate=2/1) to obtain a compound 18 as a white crystal (294 mg, 0.7 mmol, 87%).

$^1$H-NMR (400 MHz, CDCl$_3$) δ: 7.12 (d, H, J=9.2 Hz), 5.77 (d, 1H, J=9.2 Hz), 5.35 (t, 1H, J=10 Hz), 5.07 (t, 1H, J=10 Hz), 4.36 (q, 1H, J=9.6 Hz), 3.88 (m, 1H), 3.45-3.36 (m, 2H), 2.13 (s, 3H), 2.10 (s, 3H), 2.07 (s, 3H). HRMS (ESI, m/z, [M+Na]$^+$); Calculated For C$_{14}$H$_{17}$F$_3$N$_4$NaO$_8$: 499.08962, Found: 449.08529.

Synthesis of 1-thiophenyl-2-N-trifluoroacetyl-3,4-di-O-acetyl-6-azido-β-D-glucopyranose (19)

The compound 18 (500 mg, 1.3 mmol) was dissolved in dichloromethane (dehydrated) (4.50 mL). Then, thiophenol (0.18 mL, 1.8 mmol) and boron trifluoride diethyl ether complex (0.47 mL, 3.8 mmol) were added, and the mixture was stirred. The disappearance of the raw material was confirmed by TLC after 18 hours. Then, 10 mL of an aqueous solution of saturated aqueous sodium hydrogen carbonate solution:saturated aqueous sodium carbonate solution:brine=1:1:0.5 was added, and the mixture was stirred. After extraction with an aqueous solution of saturated aqueous sodium hydrogen carbonate solution:saturated aqueous sodium carbonate solution=1:1, the organic layer was dried by adding anhydrous sodium sulfate and then distilled under reduced pressure. Then, the residue was purified by silica gel column chromatography (chloroform/methanol=70/1) to obtain a compound 19 as a white crystal (580 mg, 1.24 mmol, 95%).

$^1$H-NMR (400 MHz, CDCl$_3$) δ: 7.54-7.51 (m, 2H), 7.38-7.32 (m, 3H), 6.54 (d, 1H, J=8.8 Hz), 5.25 (t, 1H, J=9.8 Hz), 4.99 (t, 1H, J=9.8 Hz), 4.84 (d, 1H, J=8.8 Hz), 3.99 (q, 1H, J=8.5 Hz), 3.70-3.66 (m, 1H), 3.41-3.33 (m, 2H), 2.01 (s, 6H). HRMS (ESI, m/z, [M+Na]$^+$); Calculated For C$_{18}$H$_{18}$F$_3$N$_4$NaO$_6$S$_1$: 500.07548, Found: 500.08002.

Synthesis of 2-N-trifluoroacetyl-3,4-O-trifluoroacetyl-6-azido-β-D-glucopyranosyl-(1→6)-1,3,4,-O-acetyl-2-N-trifluoroacetyl-β-D-glucopyranose (20)

A trifluoroacetylglucosamine derivative 20 was synthesized by combining the compound 19 and the compound 17 synthesized in the above manner.

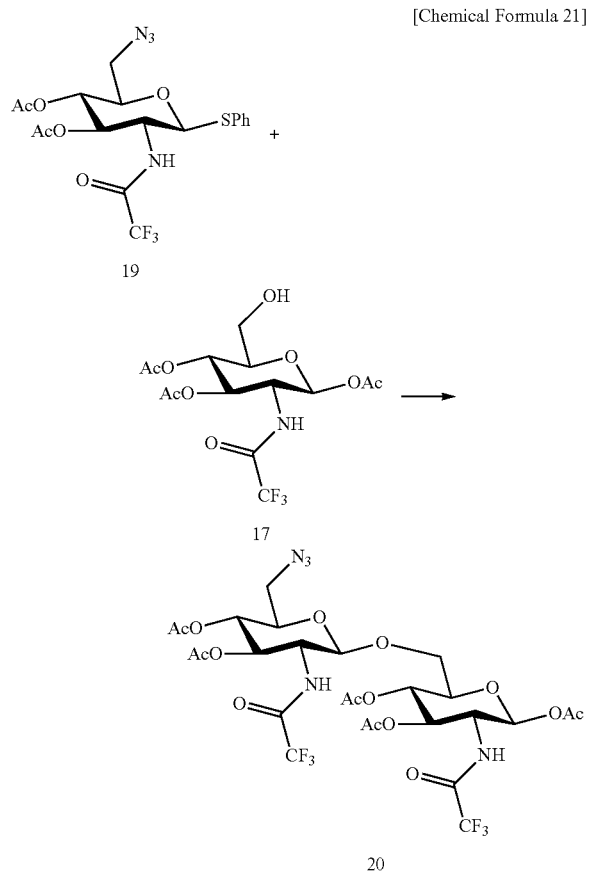

The compound 19 (200.2 mg, 0.50 mmol) and the compound 17 (170.0 mg, 0.36 mmol) were dissolved in dichloromethane (dehydrated) (16.8 mL), molecular sieves 4A (1.6 g) were added, and the mixture was stirred. Then, the mixture was cooled to −25° C., and N-iodosuccinimide (87.6 mg, 0.40 mmol) was added. After 30 minutes, trifluoromethanesulfonic acid (28.0 µL) was added, and the mixture was stirred at 0° C. The disappearance of the compound 17 was confirmed by TLC after 30 minutes. The molecular sieves 4A were removed by suction filtration, and then the filtrate was diluted by adding ethyl acetate (50 mL). The organic layer was washed with a saturated aqueous sodium thiosulfate solution (40 mL), a saturated aqueous sodium hydrogen carbonate solution, and brine. The organic layer was dried by adding anhydrous sodium sulfate, filtered, and distilled under reduced pressure. The residue was purified by silica gel column chromatography (chloroform/methanol=30/1-10/1) to obtain a compound 20 as a white crystal (251 mg, 0.46 mmol, 91%).

$^1$H-NMR (400 MHz, DMSO-d) δ: 9.64 (d, 1H, J=9.2 Hz), 9.40 (d, 1H, J=9.2 Hz), 5.74 (d, 1H, J=9.2 Hz), 5.20 (t, 1H, J=9.8 Hz), 5.11 (t, 1H, J=9.8 Hz), 4.93 (t, 1H, J=9.8 Hz), 4.85 (t, 1H, J=9.8 Hz), 4.77 (t, 1H, J=8.8 Hz), 3.86-3.77 (m, 3H), 3.53-3.43 (m, 2H), 3.29-3.25 (m, 2H), 1.97 (s, 3H), 1.95 (s, 3H), 1.91 (s, 3H), 1.87 (s, 3H), 1.84 (s, 3H). MALDI-TOF/Ms (m/z, [M+Na]$^+$); Calculated For C$_{26}$H$_{31}$F$_6$N$_5$NaO$_{15}$: 790.5, Found: 792.4.

Further, various compounds for introducing a linker moiety were synthesized. The details thereof will be described below.

Synthesis of Undecanoic Acid, 11-[(4-(azidomethyl)benzoyl)amino]-(23)

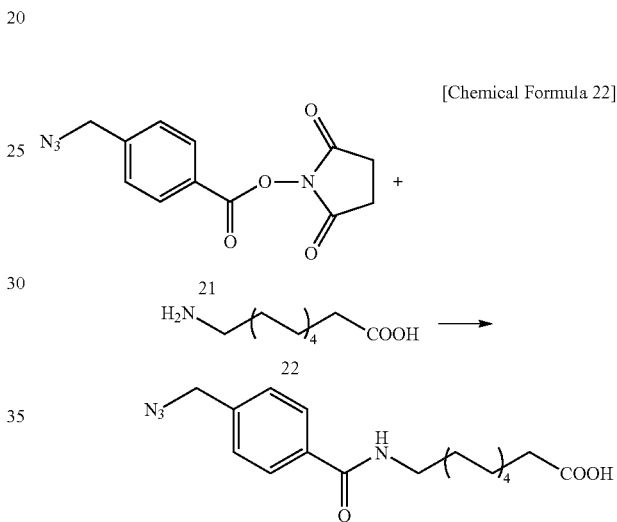

First, 11-aminoundecanoic acid 22 (2.64 g, 13.1 mmol, 1.2 eq.) and triethylamine (3.80 mL, 27.3 mmol, 2.5 eq.) were dissolved in DMF (54.5 mL), succinimidyl 4-(azidomethyl)benzoate 21 (2.99 g, 10.9 mmol) was added, and the mixture was stirred. It is to be noted that the compound 21 was synthesized by a method described in A. Gopin, S. Ebner, B. Attali, and D. Shabat, Bioconjugate Chem., 2006, 17, 1432-1440. The disappearance of the raw material was confirmed by TLC after 48 hours. Then, 5% citric acid was added to the reaction solution to adjust pH<2. After extraction with ethyl acetate, the reaction solution was subjected to liquid-liquid extraction with distilled water three times. The organic layer was washed with brine, dried over anhydrous sodium sulfate, filtered, and distilled under reduced pressure. Then, the residue was purified by silica gel column chromatography (chloroform:methanol 50:1→25:1) to obtain a compound 23 as a white crystal (3.65 g, 10.1 mmol, 93%).

$^1$H-NMR (400 MHz, CDCl$_3$) δ: 7.79-7.76 (d, 2H, J=8.4 Hz), 7.39-7.26 (d, 2H, J=7.6 Hz), 6.14 (s, 1H), 4.39 (s, 2H), 3.46-3.43 (m, 2H, J=6.4 Hz), 2.34-2.32 (q, 2H, J=7.2 Hz), 1.65-1.58 (m, 4H, J=8.6 Hz), 1.33-1.25 (q, 12H, J=15.4 Hz).

Synthesis of 4-(azidomethyl)-N-[2-[2-(2-aminoethoxy)ethoxy]ethyl]benzamide (25)

[Chemical Formula 23]

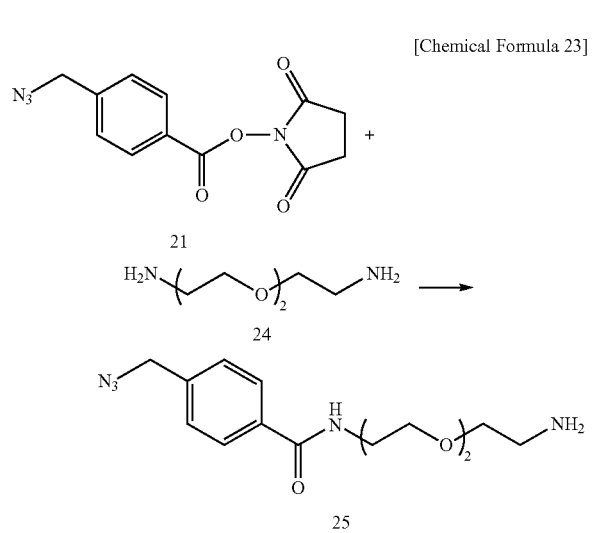

Succinimidyl 4-(azidomethyl)benzoate 21 (1.25 g, 4.56 mmol) was dissolved in dichloromethane (30 mL), a solution obtained by dissolving 1,2-bis(2-aminoethoxy)ethane 24 (3.35 g, 22.8 mmol, 5.0 eq.) in dichloromethane (16 mL) was added dropwise with a dropping funnel, and the mixture was stirred. After 18 hours, the disappearance of the raw material was confirmed by TLC, and the reaction solution was distilled under reduced pressure. Then, the residue was purified by silica gel column chromatography (chloroform:methanol=10:1+0.05% $NH_3$ aq.→5:1+0.05% $NH_3$ aq.→3:1→0.05% $NH_3$ aq.) to obtain a compound 25 (0.97 g, 2.39 mmol, 52%) as an oil.

1H-NMR (400 MHz, $CDCl_3$) δ: 7.88-7.86 (d, 2H, J=8.8 Hz), 7.39-7.37 (d, 2H, J=8.8 Hz), 7.17 (s, 1H), 4.39 (s, 2H), 3.69-3.65 (m, 8H), 3.51 (t, 2H, J=5.2 Hz), 2.86 (s, 2H), 2.28 (s, 2H).

Synthesis of 1-[3,4-O-acetyl-6-azido-2-N-trifluoroacetyl-β-D-glucopyranosyl-(1→6)-1,3,4,-O-acetyl-2-N-trifluoroacetyl-B-D-glucopyranose]-4-[3,5-bis(hydroxymethyl)phenyl]-1H-1,2,3-triazole (26)

[Chemical Formula 24]

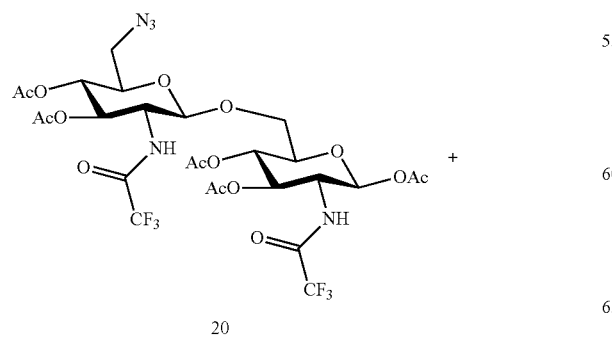

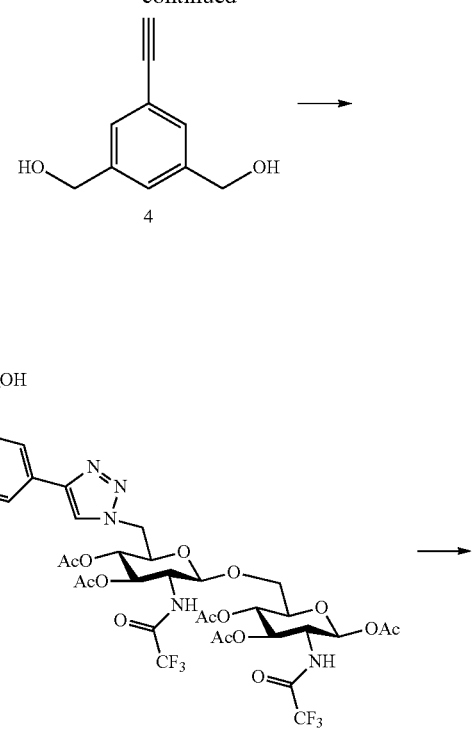

First, 5-ethynyl-1,3-benzenedimethanol (BE) 4 (100 mM solution in DMSO, 2 μL, 0.2 μmol), the compound 20 (100 mM solution in DMSO, 2 μL, 0.2 μmol), copper sulfate pentahydrate (1 M solution in Milli-Q water, 2 μL, 2 μmol), sodium ascorbate (1 M solution in Milli-Q water, 2 μL, 2 μmol), acetonitrile (4 μL), 1 M phosphate buffer (pH 7.0) (4 μL), and Milli-Q water (24 μL) were added to an Eppendorf tube and mixed for 1 second by a vortex mixer, and the mixture was allowed to stand at room temperature for 15 minutes. After lyophilization, the structure of the compound 26 was confirmed by MALDI-TOF/Ms. MALDI-TOF/Ms ([M+Na]+); Calculated For $C_{36}H_{41}N_5NaO_{15}$: 953.2, Found: 952.5.

[Chemical Formula 25]

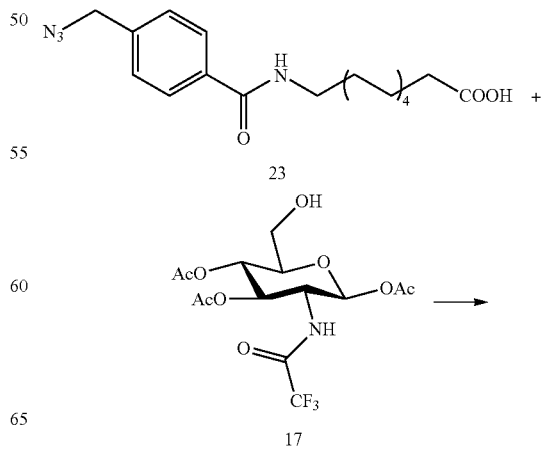

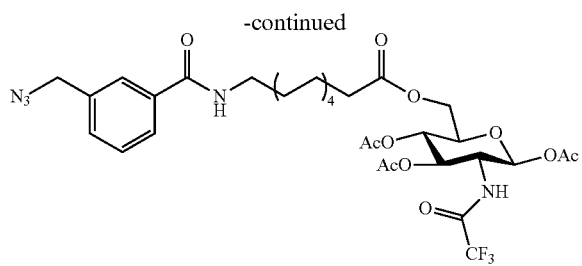

27

Synthesis of Compound (27)

The compound 17 (100 mg, 249 μmol), the compound 23 (135 mg, 375 μmol, 1.51 eq.), and DMAP (3 mg, 25 μmol, 0.1 eq.) were dissolved in pyridine (1 mL), and EDCHCl (72 mg, 376 μmol, 1.51 eq.) was added with ice cooling. After 1 day, the disappearance of the raw material was confirmed by TLC, and therefore the reaction solution was diluted with ethyl acetate (10 mL) and subjected to liquid-liquid extraction with distilled water twice and with an aqueous sodium hydrogen carbonate solution once. The organic layer was washed with brine, dried over anhydrous sodium sulfate, and distilled under reduced pressure. Flash column chromatography (hexane/ethyl acetate=4/1→3/1→1/1→ethyl acetate) was performed to obtain a compound 27 as a white crystal (196 mg, 264 μmol, 106%).

1H NMR (400 MHz, CDCl3) δ; 7.79-7.77 (d, 2H), 7.40-7.38 (d, 2H), 7.31-7.29 (d, 1H), 6.19 (s, 1H), 5.81-5.79 (d, 1H), 5.32-5.28 (t, 1H), 5.14-5.10 (t, 1H), 4.40 (s, 1H), 4.36-4.14 (m, 2H), 3.85-3.81 (m, 1H), 3.48-3.43 (dd, 2H), 2.36-2.33 (t, 2H), 2.11 (s, 3H), 2.054 (s, 3H), 2.046 (s, 3H), 1.35-1.30 (m, 13H).

The trifluoroacetylglucosamine derivatives 20 and 27 obtained in such a manner as described above can readily modify oligonucleotides by a click reaction using the azide group present in their molecules as a foothold. The thus modified oligonucleotide derivative is recognized by a receptor that is present on cell membrane surfaces and that recognizes an amino sugar, and is therefore easily taken into the nuclei of cells by endocytosis. Therefore, the modified oligonucleotide derivative can be expected to be introduced into cells without using a lipofection reagent. Further, it is considered that when a receptor on cell membrane surfaces easily receives a hydrophobic functional group, permeability is increased due to an increase in hydrophobicity achieved by the introduction of fluorine atoms.

[Chemical Formula 26]

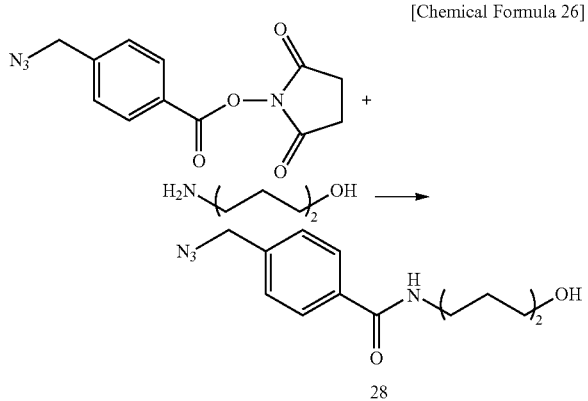

28

Synthesis of Compound 28

Succinimidyl 4-(azidomethyl)benzoate[1] (793 mg, 2.89 mmol) and 6-aminohexanol (538 mg, 4.59 mmol, 1.6 eq.) were dissolved in MeOH (30 ml), and the mixture was stirred at room temperature. The disappearance of the raw material was confirmed by TLC (EtOAc, UV, anisaldehyde) after 1 hour. The reaction solution was diluted with ethyl acetate and subjected to liquid-liquid extraction with 1 N HCl and distilled water. The organic layer was washed with brine, dried over anhydrous sodium sulfate, and distilled under reduced pressure. Then, flash column chromatography (chloroform:methanol 100:0→100:1) was performed. A compound 28 (422 mg, 1.53 mmol, 53%) was obtained as a white powder.

$^1$H NMR (400 MHz, DMSO-d$_6$) δ 8.46-8.43 (t, J=5.0 Hz 1H), 7.86-7.84 (d, J=8.0 Hz, 2H), 7.45-7.43 (d, J=8.0 Hz, 2H), 4.51 (s, 2H), 4.34-4.31 (t, J=6.0 Hz, 1H), 3.40-3.35 (q, J=8.0 Hz, 2H), 3.26-3.21 (q, J=8.0 Hz, 2H), 1.53-1.29 (m, 8l).

[Chemical Formula 27]

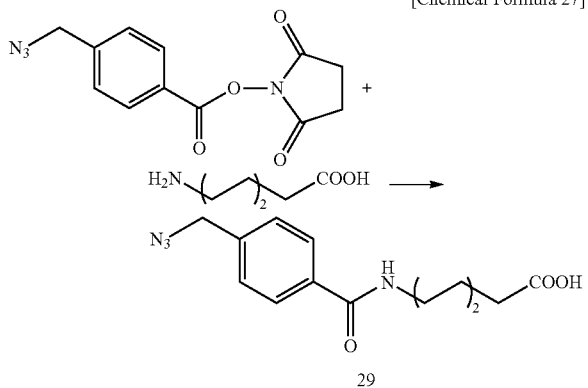

29

Synthesis of Compound 29

Under an argon purge, DMF (15 mL) and TEA (1.00 mL) were added to succinimidyl 4-(azidomethyl)benzoate[1] (823 mg, 3.00 mmol) and ε-aminocaproic acid (472 mg, 3.60 mmol, 1.2 eq). After 3 days, TLC (chloroform:methanol=5:1, detection with UV) was performed to confirm the occurrence of reaction and the disappearance of the raw material. The reaction solution was diluted with ethyl acetate and subjected to extraction with a 1 N aqueous HCl solution. The organic layer was washed with brine once and dehydrated with anhydrous sodium sulfate, and the solvent was distilled off under reduced pressure. The obtained residue was purified by silica gel column chromatography (chloroform:methanol=100:1→100:2→100:4). The solvent was distilled off under reduced pressure to obtain a compound 29 (888 mg, 2.99 mmol, 99%) as a white crystal.

$^1$H-NMR (400 MHz, CDCl$_3$) δ 7.79-7.77 (d, J=8.0 Hz, 2H), 7.39-7.37 (d, J=8.0 Hz, 2H), 6.21 (s, 1H), 4.40 (s, 2H), 3.50-3.49 (q, J=7.2 Hz, 2H), 2.41-2.37 (t, J=7.4 Hz, 2H), 1.74-1.62 (m, 4H), 1.50-1.42 (m, 2H)

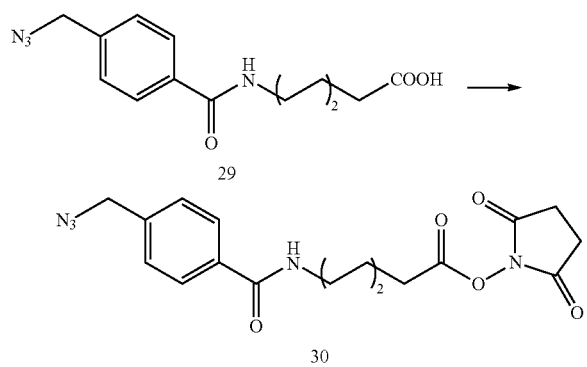

Synthesis of Compound 30

Under an argon purge, the compound 29 (581 mg, 2.00 mmol) and NHS (279 mg, 2.40 mmol, 1.2 eq) were dissolved in DMF (10 mL). WSC (581 mg, 3.00 mmol, 1.5 eq) was added, and the mixture was stirred. After 18 hours, the disappearance of the raw material was confirmed by TLC (ethyl acetate, detection with UV). The reaction solution was diluted with ethyl acetate and then subjected to liquid-liquid extraction with distilled water three times. Then, the organic layer was washed with brine once. The organic layer was dehydrated with anhydrous sodium sulfate, and the solvent was distilled off under reduced pressure. The residue was purified by column chromatography (hexane: ethyl acetate=1:1→ethyl acetate) to isolate a desired compound. As a result, a compound 30 (650 mg, 1.68 mmol, 84%) was obtained as a white crystal.

$^1$H-NMR (400 MHz, CDCl$_3$) δ 7.81-7.79 (d, J=8.4 Hz, 2H), 7.39-7.37 (d, J=8.0 Hz, 2H), 6.33 (s, 1H), 4.40 (s, 2H), 3.50-3.46 (q, J=7.0 Hz, 2H), 2.83 (s, 4H), 2.66-2.62 (t, J=7.2 Hz, 2H), 1.87-1.79 (m, 2H), 1.72-1.65 (m, 2H), 1.58-1.26 (m, 2H).

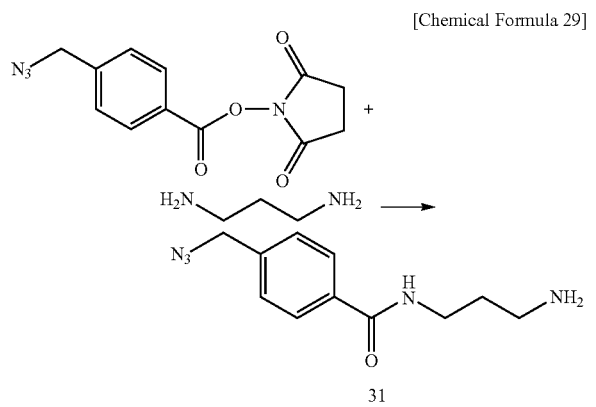

Synthesis of Compound 31

First, 1,3-diaminopropane (73.7 mg, 1.0 mmol) was dissolved in CH$_2$Cl$_2$ (10 mL), and a solution obtained by dissolving succinimidyl 4-(azidomethyl)benzoate[1] (274.2 mg, 1.0 mmol) in CH$_2$Cl$_2$ (10 mL) was slowly added dropwise (drop time: 25 minutes). After 18 hours, TLC (chloroform:methanol=3:1+1% NH$_3$ aq., UV and ninhydrin reagent) was performed to confirm that the raw material did not remain in the reaction solution. Column chromatography was performed using an elution solvent of chloroform: methanol=10:1+1% NH$_3$ aq. A yellow liquid of a compound 31 (197.1 mg, 0.8 mmol, 84%) was obtained.

$^1$H-NMR (400 MHz, CDCl$_3$): δ 7.85-7.82 (2H, t, J=4.0 Hz), 7.39-7.37 (2H, d, J=8.0 Hz), 4.40 (2H, s), 3.63-3.59 (2H, m), 2.97-2.94 (2H, t, J=6.0 Hz), 1.79-1.75 (2H, t, J=8.0 Hz).

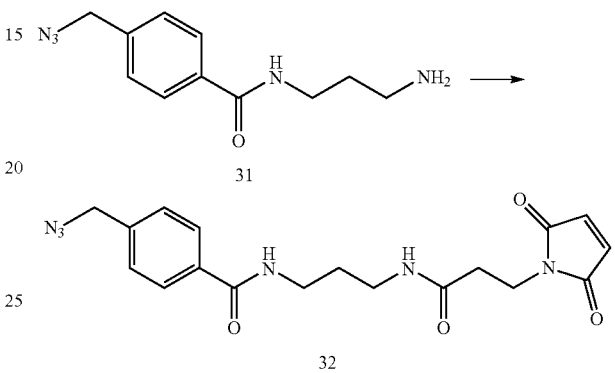

Synthesis of Compound 32

Under an argon purge, the compound 15 (108.1 mg, 0.5 mmol) was dissolved by adding DMF (6 mL), succinimido 4-maleimidohexanoate[2] (183.7 mg, 0.7 mmol, 1.5 eq) was added, and the mixture was stirred. After 6 hours, TLC (dichloromethane:acetone=1:1, UV and ninhydrin reagent) was performed to confirm that the raw material did not remain, and the reaction solution was distilled under reduced pressure. Column chromatography was performed using an elution solvent of dichloromethane:acetone=1:1 to obtain a pale yellow solid of a compound 32 (23.8 mg, 0.1 mmol, 13%).

$^1$H-NMR (400 MHz, DMSO_d$_6$): δ 8.46 (1H, s), 7.98 (1H, s), 7.87-7.85 (2, d, J=8.0 Hz), 7.47-7.45 (2H, d, J=8.0 Hz), 7.02 (2H, s), 4.53 (2H, s), 3.63-3.61 (2H, d, J=8.0 Hz), 3.25-3.23 (2H, d, J=8.0 Hz), 3.07-3.05 (2H, d, J=8.0 Hz), 2.36-2.32 (2H, t, J=8.0 Hz), 1.63-1.62 (2H, d, J=4.0 Hz).

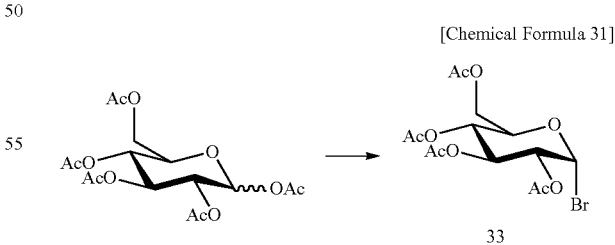

Synthesis of Compound 33

D-glucose penta acetate (1.5 g, 3.84 mmol) was dissolved in 19 mL of DCM, and hydrogen bromide (2.26 mL, 5.0 eq.) was added thereto in an ice bath. After the dropwise addition, the ice bath was removed, and the mixture was stirred at room temperature for 4 hours. After the completion of reaction, H$_2$O was added, and the mixture was subjected to extraction with CHCl$_3$. The organic layer was washed with brine, dried by adding anhydrous sodium sulfate, and then distilled under reduced pressure. Then, the residue was purified by column chromatography (hexane:EtOAc=1:1) to isolate and obtain a compound 33 (0.70 g, 44%) as a white crystal.

$^1$H NMR (400 MHz, CDCl$_3$) δ=6.60 (d, J=4.12 Hz, 1H), 5.55 (dd, J=10.08, 9.60 Hz, 1H), 5.15 (dd, J=10.52, 9.64 Hz, 1H), 4.83 (dd, J=10.52, 4.12 Hz, 1H), 4.33-4.27 (m, 2H), 4.13-4.10 (m, 1H), 2.10 (s, 3H), 2.09 (s, 3H), 2.04 (s, 3H), 2.02 (s, 3H).

[Chemical Formula 32]

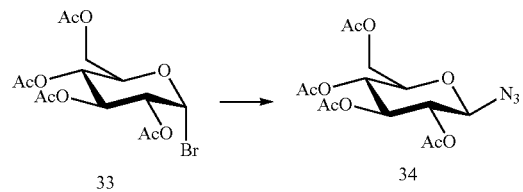

33    34

Synthesis of Compound 34

The compound 33 (0.58 g, 1.4 mmol) was dissolved in 14 mL of DMF, NaN$_3$ (0.46 g, 5.0 eq.) was added, and the mixture was stirred in an oil bath at 50° C. for 24 hours. After the completion of reaction, H$_2$O was added, and the mixture was subjected to extraction with EtOAc. The organic layer was washed with brine, dried by adding anhydrous sodium sulfate, and then distilled under reduced pressure. Then, the residue was purified by column chromatography (Hexane:EtOAc=1:1) to isolate and obtain a compound 34 (0.48 g, 91%) as a white crystal.

$^1$H NMR (400 MHz, CDCl$_3$) δ=5.21 (t, J=10.08, 9.60 Hz, 1H), 5.09 (t, J=10.08 Hz, 1H), 4.94 (dd, J=9.60, 9.16 Hz, 1H), 4.63 (d, J=8.72 Hz, 1H), 4.26 (dd, J=12.84, 4.60 Hz, 1H), 4.16 (dd, J=12.84, 2.28 Hz, 1H) 3.78 (dddd, J=2.28, 4.60, 10.08 Hz, 1H), 2.09 (s, 3H), 2.07 (s, 3H), 2.02 (s, 3H), 2.02 (s, 3H).

[Chemical Formula 33]

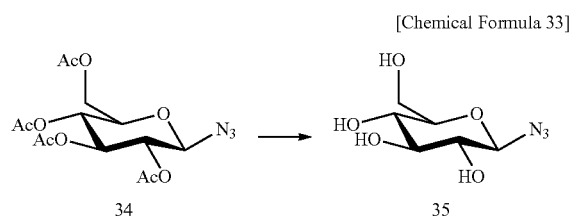

34    35

Synthesis of Compound 35

First, 10 mL of 16% NH$_3$/MEOH was added to the compound 2 (0.36 g, 0.96 mmol), and the mixture was stirred at room temperature for 8 hours. The completion of reaction was confirmed by TLC, and then the reaction solution was distilled under reduced pressure to quantitatively obtain a compound 35 as a transparent oil.

$^1$H NMR (400 MHz, DMSO-d$_6$) δ=5.46 (d, J=5.60 Hz, 1H), 5.07 (d, J=5.60 Hz, 1H), 5.00 (d, J=5.60 Hz, 1H), 4.59 (d, J=6.00 Hz, 1H), 4.42 (d, J=8.8 Hz, 1H), 3.66-3.61 (m, 1H) 3.43-3.37 (m, 1H), 3.22-3.16 (m, 1H), 3.14-3.11 (m, 1H), 3.02 (ddd, J=9.20, 5.60 Hz, 1H), 2.94 (ddd, J=5.60, 9.00 Hz, 1H).

$^{13}$C NMR (100.5 MHz, DMSO-d$_6$) δ=90.6, 79.7, 77.1, 73.8, 70.1, 61.3.

[Chemical Formula 34]

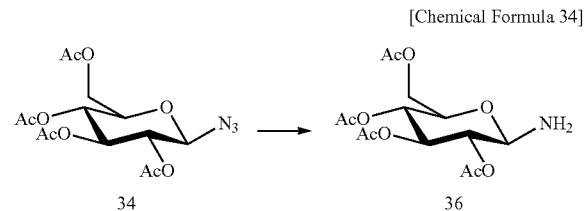

34    36

Synthesis of Compound 36

The compound 34 (0.44 g, 1.4 mmol) was dissolved in 11.8 mL of MeOH, Pd/C (44 mg, 10 wt %) was added, and the mixture was stirred under a hydrogen atmosphere for 3 hours. After the completion of reaction, the reaction solution was filtered through Celite with EtOAc, and the organic layer was distilled under reduced pressure. Then, the residue was purified by column chromatography (hexane:EtOAc=1:1) to isolate and obtain a compound 36 (0.30 g, 73%) as a white crystal.

$^1$H NMR (400 MHz, CDCl$_3$) δ=5.23 (dd, J=10.08, 9.64 Hz, 1H), 5.03 (dd, J=10.08, 9.64 Hz, 1H), 4.82 (dd, J=9.60, 9.16 Hz, H), 4.24-4.17 (m, 2H), 4.11-4.07 (m, 1H), 3.68 (dddd, J=2.28, 4.60, 10.08 Hz, 1H), 2.06 (s, 3H), 2.04 (s, 3H), 2.00 (s, 3H), 1.99 (s, 3H). $^{13}$C NMR (98.5 MHz, CDCl$_3$) δ=170.8, 170.3, 169.7, 85.1, 73.2, 72.8, 72.1, 68.8, 62.4, 20.9, 20.7.

[Chemical Formula 35]

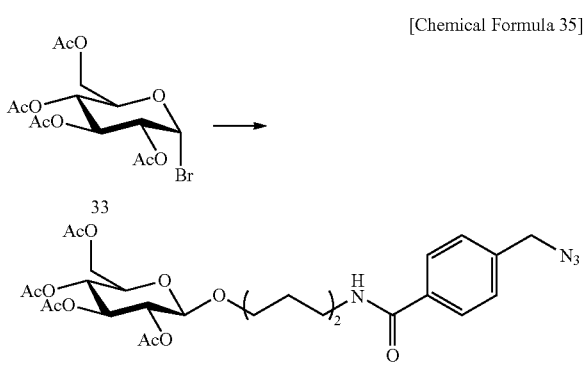

Synthesis of Compound 37

The compound 33 (1.13 g, 2.0 eq.) and the compound 28 (0.40 g, 1.38 mmol) were dissolved in 5 mL of pyridine, Ag$_2$CO$_3$ (1.52 g, 4.0 eq.) was added, and the mixture was stirred for 19 hours. After the completion of reaction, 5% HCl was added, and the mixture was subjected to extraction with EtOAc. The organic layer was washed with H$_2$O, a saturated aqueous sodium hydrogen carbonate solution, and brine, dried by adding anhydrous sodium sulfate, and then distilled under reduced pressure. Then, the residue was purified by column chromatography (hexane:EtOAc=:1:1) to isolate and obtain a compound 37 (0.49 g, 64%) as a white crystal.

$^1$H NMR (400 MHz, CDCl$_3$) δ 7.77 (d, J=8.40 Hz, 2H), 7.37 (d, J=8.40 Hz, 2H), 6.19-6.16 (m, 1H), 5.67 (d, J=7.60 Hz, 1H), 5.23 (t, J=9.20 Hz, 1H), 5.16-5.10 (m, 2H) 4.39 (s, 2H), 4.27 (dd, J=12.40, 4.40 Hz, 1H), 4.21-4.09 (m, 3H), 3.82 (dddd, J=2.40, 4.40, 10.00 Hz, 1H), 3.44 (dd, J=6.60, 11.80 Hz, 2H), 2.07 (s, 3H), 2.03 (s, 3H), 2.02 (s, 3H), 2.00 (s, 3H), 1.70-1.60 (m, 4H), 1.42-1.39 (m, 4H).

$^{13}$C NMR (100.5 MHz, CDCl$_3$) δ=170.7, 170.2, 169.2, 153.5, 138.8, 134.8, 128.3, 127.5, 95.0, 72.8, 70.2, 69.1, 67.7, 61.4, 54.3, 40.0, 29.6, 28.4, 26.6, 25.4, 20.8, 20.7, 20.7.

[Chemical Formula 36]

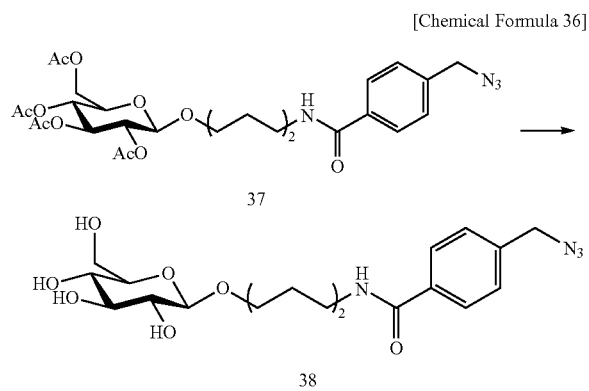

Synthesis of Compound 38

The compound 37 (0.72 g) was dissolved in dry MeOH, an appropriate amount of 28% Sodium Methoxide Methanol Solution was added, and the mixture was shaken. After 5 minutes, the completion of reaction was confirmed by TLC. Then, DOWEX 50 WX8-100 ion-exchange resin was added, and the mixture was shaken, filtered through a cotton plug, and distilled under reduced pressure. Then, the residue was purified by column chromatography (CHCl$_3$:CH$_3$OH=5:1) to isolate and obtain a compound 38 (0.19 g) as a white crystal.

$^1$H NMR (400 MHz, DMSO-d$_6$) δ=8.43 (t, J=5.60 Hz, 1H), 7.81 (d, J=8.40 Hz, 1H), 7.41 (d, J=8.40 Hz, 1H), 4.91 (d, J=4.80 Hz, 1H), 4.87 (d, J=4.80 Hz, 1H), 4.84 (d, J=4.4 Hz, 1H) 4.48 (s, 2H), 4.43 (t, J=6.00 Hz, 1H), 4.05 (d, J=7.60 Hz, 1H), 3.75-3.69 (m, 1H), 3.64-3.59 (m, 1H), 3.42-3.34 (m, 2H), 3.23-3.18 (m, 2H), 3.10-2.98 (m, 3H), 2.89 (ddd, J=5.20, 8.20 Hz, 1H).

$^{13}$C NMR (100.5 MHz, DMSO-d$_6$) δ=166.2, 139.0, 135.0, 128.7, 128.1, 103.4, 77.3, 74.0, 70.6, 69.0, 61.6, 53.6, 29.8, 29.6, 26.9, 25.8.

[Chemical Formula 37]

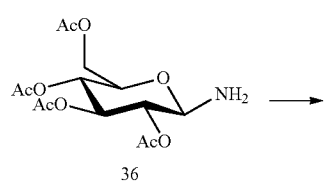

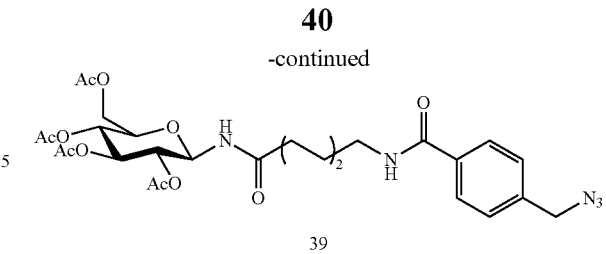

Synthesis of Compound 39

The compound 36 (0.25 g, 2.2 eq.) was added to the compound 36 (0.1 g, 0.29 mmol), and the mixture was stirred in 1 mL of THF overnight. Then, the reaction solution was distilled under reduced pressure, and the residue was purified by column chromatography (CHCl$_3$:CH$_3$OH=50:1) to isolate and obtain a compound 39 (17.9 mg, 11%) as a white crystal.

$^1$H NMR (400 MHz, DMSO-d$_6$) δ=8.59 (d, J=9.64, 1H), 8.43 (t, J=5.50 Hz, 1H), 7.81 (d, J=8.24 Hz, 1H), 7.40 (d, J=8.72 Hz, 1H), 5.37-5.27 (m, 2H), 4.86-4.77 (m, 2H) 4.48 (s, 2H), 4.13-4.03 (m, 2H), 3.93-3.90 (m, 2H), 3.21-3.16 (m, 2H), 2.08-2.03 (m, 2), 2.05 (s, 3H), 1.96 (s, 3H), 1.95 (s, 3H), 1.94 (s, 3H), 1.47-1.44 (m, 4H), 1.24-1.19 (m, 2H).

[Chemical Formula 38]

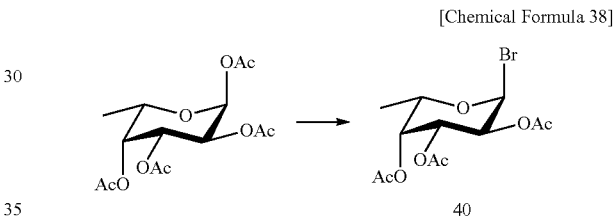

Synthesis of Compound 40

1,2,3,4-tetra-O-acetyl-a-$_L$-fucopyranose (1.5 g, 4.50 mmol) was dissolved in 22.5 mL of DCM, and hydrogen bromide (2.26 mL, 5.0 eq.) was added thereto in an ice bath. After the dropwise addition, the ice bath was removed, and the mixture was stirred at room temperature for 3.5 hours. After the completion of reaction, H$_2$O was added, and the mixture was subjected to extraction with CHCl$_3$. The organic layer was washed with brine, dried by adding anhydrous sodium sulfate, and then distilled under reduced pressure. Then, the residue was purified by column chromatography (hexane:EtOAc=4:1) to isolate and obtain a compound 40 (1.33 g, 84%) as a white crystal.

[Chemical Formula 39]

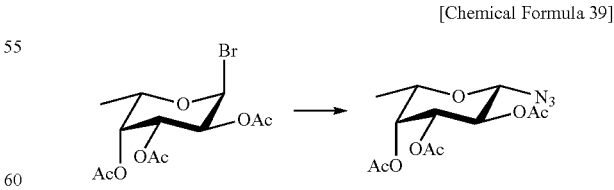

Synthesis of Compound 41

The compound 40 (1.23 g, 3.48 mmol) was dissolved in 17 mL of DMF, NaN$_3$ (1.13 g, 5.0 eq.) was added, and the mixture was stirred in an oil bath at 50° C. for 24 hours. After the completion of reaction, H₂O was added, and the mixture was subjected to extraction with EtOAc. The organic layer was washed with brine, dried by adding anhydrous sodium sulfate, and then distilled under reduced pressure. Then, the residue was purified by column chromatography (hexane:EtOAc=1:1) to isolate and obtain a compound 41 (0.74 g, 52%) as a white crystal.

¹H NMR (400 MHz, CDCl₃) δ=5.26-5.25 (m, 1H), 5.13 (dd, J=10.0, 8.80 Hz, 1H), 5.02 (dd, J=10.0, 3.60 Hz, 1H), 4.57 (d, J=8.80 Hz, 1H), 3.89 (ddd, J=6.40, 0.80 Hz, 1H), 2.18 (s, 3H), 2.07 (s, 3H), 1.98 (s, 3H), 1.24 (d, J=6.40 Hz, 3H).

¹³C NMR (100.5 MHz, CDCl₃) δ=170.6, 170.2, 169.6, 88.3, 71.6, 71.2, 70.0, 68.3, 20.8, 20.7, 20.7, 16.1.

[Chemical Formula 40]

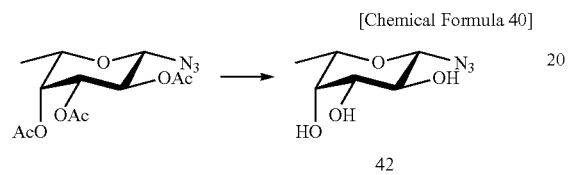

42

Synthesis of Compound 42

First, 15 mL of 16% NH₃/MEOH was added to the compound 41 (0.51 g. 1.62 mmol), and the mixture was stirred at room temperature for 4 hours. The completion of reaction was confirmed by TLC, and then the reaction solution was distilled under reduced pressure to quantitatively obtain a compound 42 (0.39 g) as a transparent oil.

¹H NMR (400 MHz, DMSO-d₆) δ=5.23 (d, J=5.20 Hz, 1H), 4.81 (d, J=5.60 Hz, 1H), 4.56 (d, J=4.40 Hz, 1H), 4.31-4.29 (m, 1H), 3.61 (dd, J=12.80, 6.40 Hz, 1H), 3.40-3.39 (m, 1H), 3.30-3.26 (m, 2H), 3.13 (d, J=5.20 Hz, 1H), 1.10 (d, J=6.40 Hz, 3H).

¹³C NMR (100.5 MHz, DMSO-d₆) δ=91.0, 73.9, 73.0, 71.4, 70.4, 17.1.

[Chemical Formula 41]

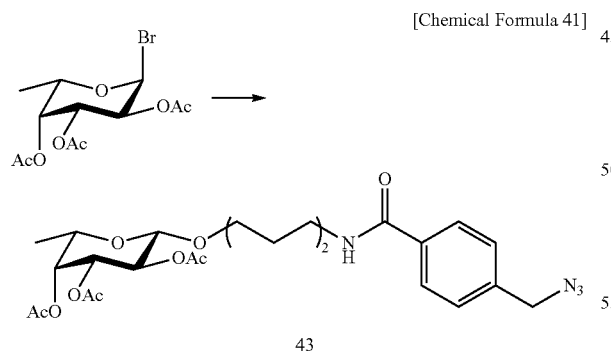

43

Synthesis of Compound 43

The compound 40 (0.60 g, 1.5 eq.) and the compound 28 (0.33 g, 1.14 mmol) were dissolved in 5 mL of pyridine, Ag₂CO₃ (1.25 g, 4.0 eq.) was added, and the mixture was stirred for 24 hours. After the completion of reaction, 5% HCl was added, and the mixture was subjected to extraction with EtOAc. The organic layer was washed with H₂O, a saturated aqueous sodium hydrogen carbonate solution, and brine, dried by adding anhydrous sodium sulfate, and then distilled under reduced pressure. Then, the residue was purified by column chromatography (hexane:EtOAc=1:1).

[Chemical Formula 42]

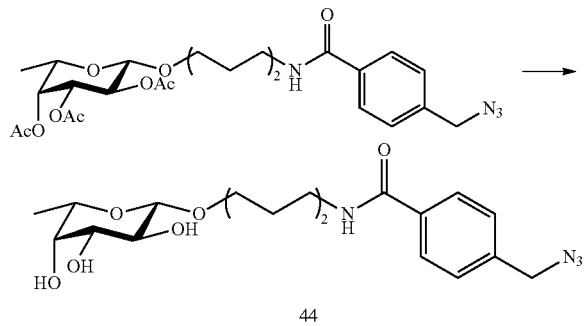

44

Synthesis of Compound 44

The compound 43 (0.20 g, mixture) was dissolved in 3 mL of dry MeOH, an appropriate amount of 28% Sodium Methoxide Methanol Solution was added, and the mixture was shaken. After 5 minutes, the completion of reaction was confirmed by TLC. Then, DOWEX 50 WX8-100 ion-exchange resin was added, and the mixture was shaken, filtered through a cotton plug, and distilled under reduced pressure. Then, the residue was purified by column chromatography (CHCl₃:CH₃OH=5:1) to isolate and obtain a compound 44 (10 mg, 7% (2 steps)) as a white crystal.

¹H NMR (400 MHz, DMSO-d₆) δ=8.43 (t, J=6.00 Hz, 1H), 7.81 (d, J=8.40 Hz, 2H), 7.41 (d, J=8.40 Hz, 2H), 4.73 (d, J=4.00 Hz, 1H), 4.58 (d, J=5.20 Hz, 1H), 4.48 (s, 2H), 4.32 (d, J=5.20 Hz, 1H), 3.99 (d, J=6.80 Hz, 1H), 3.68-3.62 (m, 1H), 3.46-3.41 (m, 1H), 3.38-3.33 (m, 2H), 3.26-3.15 (m, 4H), 1.51-1.46 (m, 4H), 1.28 (m, 4H), 1.06 (d, J=6.40 Hz, 3H).

[Chemical Formula 43]

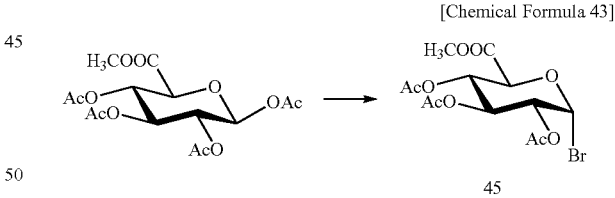

45

Synthesis of Compound 45

Methyl-1,2,3,4-tetra-O-acetyl-β-$_D$-glucuronate (1.5 g, 4.50 mmol) was dissolved in 20 mL of DCM, and hydrogen bromide (2.34 ml., 3.0 eq.) was added thereto in an ice bath. After the dropwise addition, the ice bath was removed, and the mixture was stirred at room temperature for 4 hours. After the completion of reaction, H₂O was added, and the mixture was subjected to extraction with CHCl₃. The organic layer was washed with brine, dried by adding anhydrous sodium sulfate, and then distilled under reduced pressure. Then, the residue was purified by column chromatography (hexane:EtOAc=4:1) to isolate and obtain a compound 45 (0.22 g, 14%) as a white crystal.

[Chemical Formula 44]

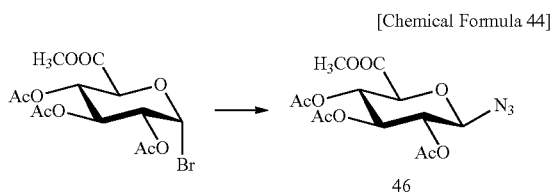

Synthesis of Compound 46

The compound 45 (0.22 g, 0.55 mmol) was dissolved in 5.5 mL of DMF, NaN$_3$ (0.18 g, 5.0 eq.) was added, and the mixture was stirred in an oil bath at 50° C. for 24 hours. After the completion of reaction, H$_2$O was added, and the mixture was subjected to extraction with EtOAc. The organic layer was washed with brine, dried by adding anhydrous sodium sulfate, and then distilled under reduced pressure. Then, the residue was purified by column chromatography (hexane:EtOAc=1:1) to isolate and obtain a compound 46 (0.12 g, 61%) as a white crystal.

$^1$H NMR (400 MHz, CDCl$_3$) δ=5.26-5.22 (m, 2H), 4.95 (dd, J=9.60, 9.16 Hz, 1H), 4.70 (d, J=9.16 Hz, 1H), 4.10 (d, J=9.64 Hz, 1H), 3.77 (s, 3H), 2.07-2.00 (m, 9H).

$^1$C NMR (98.5 MHz. CDCl$_3$) δ=170.1, 169.2, 88.2, 74.3, 71.9, 70.5, 69.1, 53.2, 20.7, 20.7, 20.6.

[Chemical Formula 45]

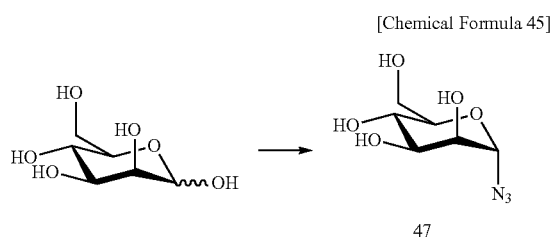

Synthesis of Compound 47

D-mannose (0.18 g, 1.80 mmol) was dissolved in H$_2$O/1,4-dioxane (=1:1, 4 mL), and the solution was cooled to −10° C. 2-chloro-1,3-dimethylimidazolium chloride (0.50 g, 2.96 mmol, 1.6 eq.), NaN$_3$ (0.59 g, 9.08 mmol, 5.0 eq.), and TEA (1.3 mL, 9.33 mmol, 5.2 eq.) were added, and the mixture was stirred. After 23 hours, the disappearance of the raw material was confirmed by TLC (CHCl$_3$:MeOH 3:1, 5% sulfuric acid in MeOH). The solvent was distilled off under reduced pressure. Flash column chromatography (CHCl$_3$:CH$_3$OH=10:1) was performed. A compound 47[3] (0.16 g, 0.76 mmol, 75%) was obtained as a white solid.

[Chemical Formula 46]

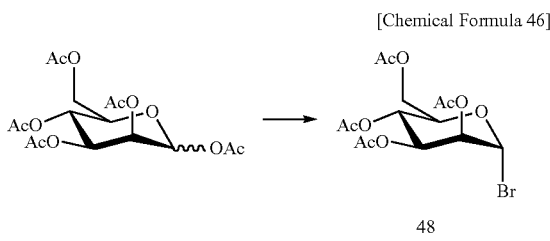

Synthesis of Compound 48

D-mannose penta acetate (0.70 g, 1.80 mmol) was dissolved in CH$_2$Cl$_2$ (40 mL), and 0.69 M HBr in AcOH (7 mL) was slowly added dropwise with ice cooling under an Ar atmosphere. After the completion of the dropwise addition, the reaction solution was returned to room temperature and stirred. After 23 hours, the disappearance of the raw material was confirmed by TLC (hexane:EtOAc 2:1, 5% sulfuric acid in MeOH). The reaction solution was cooled with ice, brine was added, and the mixture was stirred. After 30 minutes, the aqueous layer was removed, saturated sodium bicarbonate water was added, and the mixture was stirred. The reaction solution was diluted with CH$_2$Cl$_2$ and then subjected to liquid-liquid extraction with a saturated aqueous sodium hydrogen carbonate solution and water. After washed with brine, the organic layer was dried over anhydrous sodium sulfate and distilled under reduced pressure. A compound 48 (0.63 g, 1.53 mmol, 85%) was obtained as an oil.

$^1$H NMR (400 MHz, CDCl$_3$) δ6.29 (s, 1H), 5.74-5.70 (dd, J=13.7, 7.6 Hz, 1H), 5.45 (s, 1H), 5.40-5.35 (t, J=10.2 Hz, 1H), 4.36-4.31 (dd, J=17.6, 4.9 Hz, 1H), 4.24-4.20 (m, 1H), 4.16-4.12 (m, 1H), 2.18 (s, 3H), 2.11 (s, 3H), 2.08 (s, 3H), 2.01 (s, 3H).

[Chemical Formula 47]

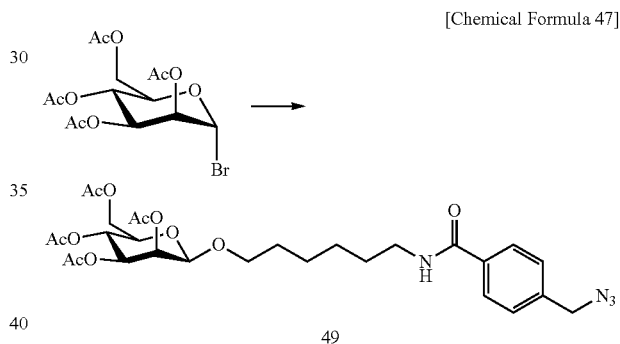

Synthesis of Compound 49

Under an Ar purge, the compound 48 (0.21 g, 0.50 mmol) was dissolved in CH$_2$Cl$_2$ (3 mL), the compound 28 (0.22 g, 0.81 mmol, 1.6 eq.) and Na$_2$SO$_3$ (30 mg) were added, and the mixture was stirred. After 30 minutes, Ag$_2$CO$_3$ (0.15 g, 0.53 mmol, 1.1 eq.) and DIPEA (0.1 ml, 0.57 mmol, 1.1 eq.) were added, and the mixture was stirred. After 9 hours, the disappearance of the raw material was confirmed by TLC (hexane:EtOAc=1:1, UV, 5% sulfuric acid in MeOH). The reaction solution was filtered, and the solvent was distilled off under reduced pressure. The residue was purified by column chromatography (hexane:EtOAc=2:1→1:1). A compound 49 (0.10 g, 0.17 mmol, 33%) was obtained as a white powder.

$^1$H-NMR (400 MHz, CDCl$_3$) δ: 6.69-6.68 (d, J=6.4 Hz, 1H), 6.29-6.27 (d, J=8.3 Hz, 1H), 5.50-5.47 (t, J=5.2 Hz, 1H), 4.37-4.36 (d, J=2.8 Hz, 1H), 4.14-4.04 (m, 2H), 3.48-3.46 (t, J=3.0 Hz, 1H), 3.31 (s, 2H), 3.11-3.01 (m, 2H), 2.61-2.57 (m, 1H), 2.42-2.27 (m, 4H), 0.97 (s, 3H), 0.94 (s, 3H), 0.93 (s, 3H), 0.58 (s, 3H), 0.51 (m, 4H), 0.31-0.21 (m, 4H).

$^{13}$C NMR (100 MHz, CDCl$_3$) δ165.93, 165.62, 165.04, 162.13, 134.27, 130.37, 123.64, 122.87, 119.70, 92.85, 90.43, 72.17, 66.61, 66.07, 61.01, 57.71, 57.55, 49.70, 49.54, 49.28, 49.00, 48.73, 48.47, 35.42, 25.02, 24.84, 22.15, 21.26, 20.33, 16.03, 16.00.

bicarbonate water was added, and the mixture was stirred. The reaction solution was diluted with $CH_2Cl_2$ and then subjected to liquid-liquid extraction with a saturated aque-

[Chemical Formula 48]

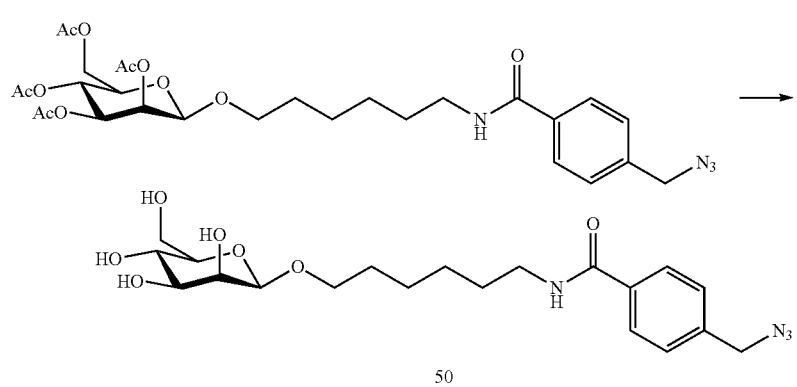

Synthesis of Compound 50

The compound 49 (92.5 mg, 0.15 mmol) was dissolved in 3 mL of dry MeOH, sodium methoxide (9.9 mg, 0.18 mmol, 1.2 eq.) was added, and the mixture was stirred. On the next day, the completion of reaction was confirmed by TLC ($CHCl_3$:MeOH=5:1, UV, 5% $H_2SO_4$ in EtOH), and the reaction solution was neutralized by adding DOWEX 50 WX8-100 ion-exchange resin. The reaction solution was filtered through a cotton plug and concentrated under reduced pressure. A compound 50 was quantitatively obtained as a white solid.

$^{13}$C NMR (100 MHz, $CD_3OD$) δ172.48, 169.67, 140.72, 135.60, 129.31, 128.68, 93.02, 74.92, 73.97, 72.94, 72.25, 70.38, 68.96, 68.69, 62.83, 62.76, 54.94, 40.96, 33.52, 30.45, 27.87, 26.62, 20.92.

ous sodium hydrogen carbonate solution and water. After washed with brine, the organic layer was dried over anhydrous sodium sulfate and distilled under reduced pressure. A compound 51 (0.51 g, 1.09 mmol, 85%) was obtained as an oil.

$^1$H NMR (400 MHz, $CDCl_3$) δ6.7-6.68 (d, J=9.8 Hz, 1H), 6.55-6.54 (d, J=5.4 Hz, 1H), 5.42-5.36 (t, J=10.2 Hz, 1H), 5.31-5.26 (t, J=9.8 Hz, 1H), 4.36-4.32 (m, 2H), 4.28-4.25 (m, 1H), 4.16-4.13 (d, J=12.7 Hz, 1H), 2.12 (s, 3H), 2.08 (s, 3H), 2.07 (s, 3H).

[Chemical Formula 49]

[Chemical Formula 50]

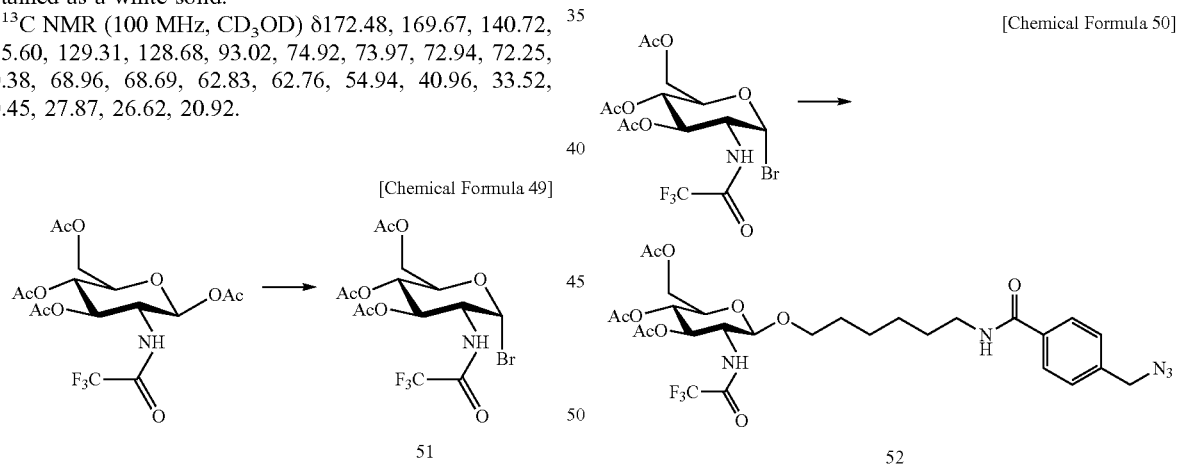

Synthesis of Compound 51

β-D-glucopyranose, 2-deoxy-2-[(2,2,2-trifluoroacetyl)amino]-, 1,3,4,6-tetraacetate (0.57 g, 1.28 mmol) was dissolved in $CH_2Cl_2$ (30 mL), and 0.69 M HBr in AcOH (6 mL) was slowly added dropwise with ice cooling under an Ar atmosphere. After the completion of the dropwise addition, the reaction solution was returned to room temperature and stirred. After 16 hours, the disappearance of the raw material was confirmed by TLC (hexane:EtOAc=1:2, 5% sulfuric acid in MeOH). The reaction solution was cooled with ice, brine was added, and the mixture was stirred. After 30 minutes, the aqueous layer was removed, saturated sodium

Synthesis of Compound 52

Under an Ar purge, the compound 51 (0.23 g, 0.50 mmol) was dissolved in $CH_2Cl_2$ (3 mL), the compound 28 (0.21 g, 0.75 mmol, 1.5 eq.) and $Na_2SO_3$ (30 mg) were added, and the mixture was stirred. After 30 minutes, $Ag_2CO_3$ (0.15 g, 0.54 mmol, 1.1 eq.) and DIPEA (0.1 mL, 0.57 mmol, 1.1 eq.) were added, and the mixture was stirred. After 9 hours, the disappearance of the raw material was confirmed by TLC (hexane:EtOAc=1:1, UV, 5% sulfuric acid in MeOH). The reaction solution was filtered, and the solvent was distilled off under reduced pressure. The residue was purified by column chromatography (hexane:EtOAc=2:1→1:1). A compound 52 (0.17 g, 0.26 mmol, 53%) was obtained as a white powder.

$^1$H-NMR (400 MHz, CD$_3$OD) δ: 7.50-7.47 (d, J=9.2 Hz, 1H), 7.06-7.04 (d, J=8.2 Hz, 1H), 6.63-6.61 (d, J=8.2 Hz, 1H), 6.04-6.01 (t, J=5.7 Hz, 1H), 4.67-4.53 (m, 1H), 4.27-4.23 (t, J=9.9 Hz, 1H), 3.90-3.88 (d, J=8.2 Hz, 1H), 3.64 (s, 2H), 3.48-3.42 (m, 1H), 3.36-3.18 (m, 2H), 3.08-3.02 (m, 1H), 2.84-2.48 (m, 3H), 1.26 (s, 3H), 1.23 (s, 3M), 1.21 (s, 3H), 0.83-0.76 (m, 4H), 0.66-0.52 (m, 4H).

$^{13}$C NMR (100 MHz, CD$_3$OD) δ166.11, 166.04, 165.03, 162.79, 134.68, 129.97, 123.75, 123.04, 95.40, 67.56, 67.23, 64.95, 64.22, 57.55, 50.26, 49.54, 34.81, 24.72, 24.36, 21.41, 20.33, 16.01, 15.96, 15.78.

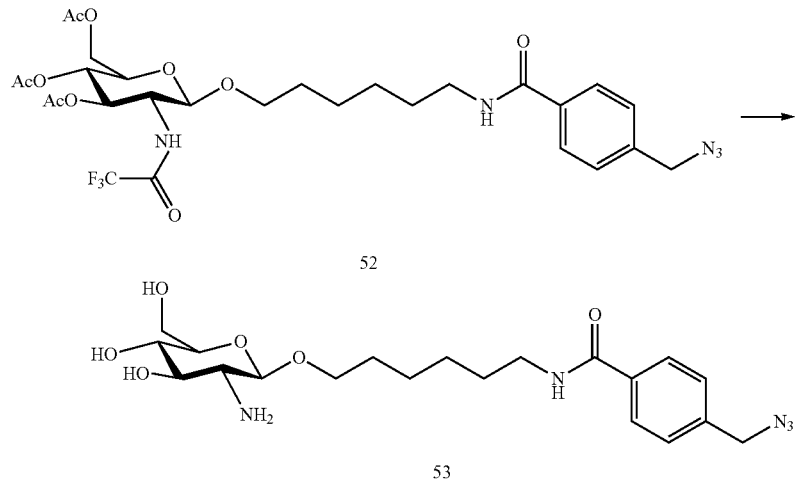

[Chemical Formula 51]

52

53

Synthesis of Compound 53

The compound 52 (108 mg, 0.16 mmol) was dissolved in 16% NH$_3$/MeOH (6 mL), and the solution was stirred. After 16 hours, the disappearance of the raw material was confirmed by TLC (CHCl$_3$:CH$_3$OH=5:1, UV, anisaldehyde). Then, the solvent was distilled off under reduced pressure. A compound 53 (70.1 mg, 0.16 mmol, 98%) was obtained as a yellow oil.

$^{13}$C NMR (100 MHz, CD$_3$OD) δ169.66, 140.73, 135.62, 129.33, 128.70, 103.68, 78.19, 76.88, 71.79, 70.65, 62.62, 58.17, 54.96, 40.91, 30.59, 30.38, 27.80, 26.81, 22.07.

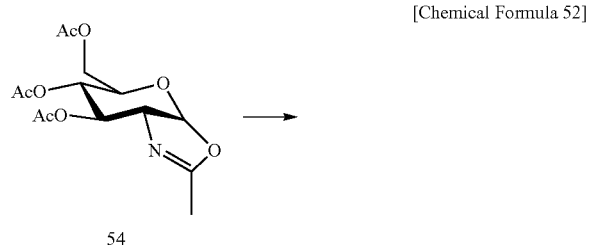

[Chemical Formula 52]

54

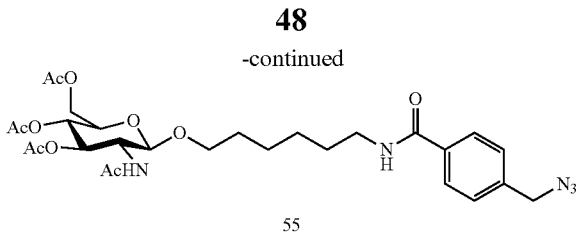

55

Synthesis of Compound 55

Under an Ar purge, oxazoline 54 (0.38 g, 1.14 mmol) was dissolved in CH$_2$Cl$_2$ (10 mL), the compound 28 (0.42 g, 1.53 mmol, 1.3 eq.) and (+)-10-camphorsulfonic acid (0.07 g, 0.31 mmol, 0.3 eq.) were added, and the mixture was stirred. After 19 hours, the disappearance of the raw material was confirmed by TLC (EtOAc, UV, 5% sulfuric acid in MeOH). TEACH was added, and the mixture was stirred for 30 minutes. The reaction solution was diluted with CH$_2$Cl$_2$ and then subjected to liquid-liquid extraction with saturated sodium hydrogen carbonate and water. The organic layer was washed with distilled water and dried over anhydrous sodium sulfate, and the solvent was distilled off under reduced pressure. The residue was purified by column chromatography (hexane:EtOAc→1:2→1:3→1:5→0:10).

A compound 55 (0.45 g, 0.73 mmol, 64%) was obtained as a white solid.

$^1$H-NMR (400 MHz, CDCl$_3$) δ: 7.84-7.82 (d, J=8.2 Hz, 1H), 7.36-7.34 (d, J=8.2 Hz, 1H), 6.99-6.96 (t, J=5.7 Hz, 1H), 6.70-6.68 (d, J=9.2 Hz, 1H), 5.28-5.23 (t, J=9.9 Hz, 1H), 5.00-4.96 (t, J=8.2 Hz, 1H), 4.36 (s, 2H), 4.21-4.17 (dd, J=17.0, 9.6 Hz, 1H), 4.07-4.04 (dd, J=15.6, 6.9 Hz, 1H), 3.86-3.78 (m, 1H), 3.60-3.56 (m, 1H), 3.49-3.30 (m, 3H), 2.01 (s, 3H), 1.98 (s, 3H), 1.97 (s, 3H), 1.88 (s, 3H), 1.58-1.49 (m, 4H), 1.37-1.31 (m, 4H).

$^{13}$C NMR (100 MHz, CDCl$_3$) δ170.79, 170.68, 169.51, 167.20, 138.84, 134.48, 128.23, 127.67, 100.67, 72.55, 71.62, 69.42, 68.89, 62.24, 60.43, 54.60, 54.21, 39.60, 29.27, 28.92, 26.13, 25.21, 23.23, 20.78, 20.72, 20.67, 14.19.

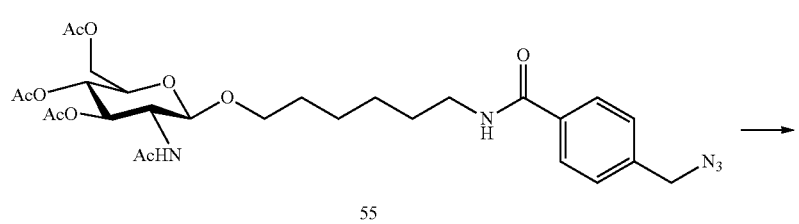

55

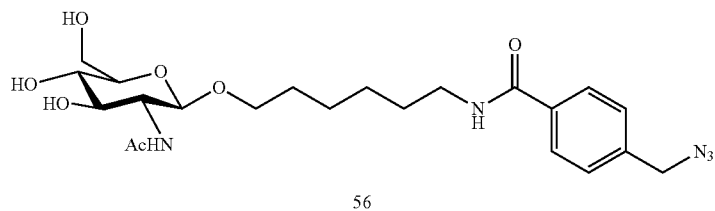

56

Synthesis of Compound 56

The compound 55 (345 mg, 0.57 mmol) was dissolved in 16% NH$_3$/MeOH (8 mL), and the solution was stirred. After 19 hours, the disappearance of the raw material was confirmed by TLC (CHCl$_3$:CH$_3$OH=5:1, UV, anisaldehyde). Then, the solvent was distilled off under reduced pressure. A compound 56 was quantitatively obtained as a white solid.

[Chemical Formula 54]

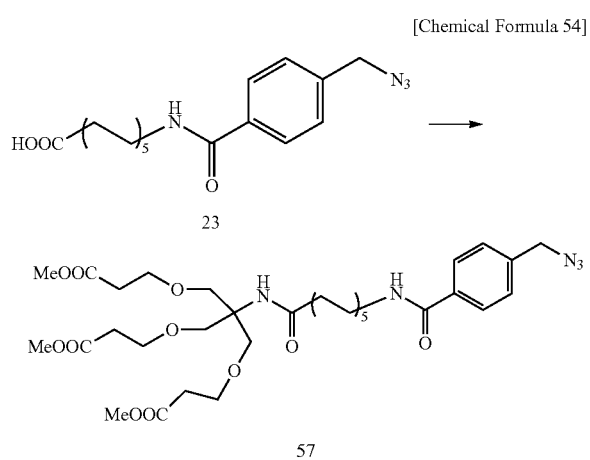

23

57

Synthesis of Compound 57

The compound 23 (1.21 g, 3.61 mmol), HOBt (0.59 g, 4.40 mmol, 1.2 eq.), DCC (1.21 g, 5.88 mmol, 1.6 eq.) were dissolved in CH$_2$Cl$_2$ (18 ml), and the solution was stirred at room temperature. After 10 hours, the disappearance of the raw material was confirmed by TLC (EtOAc, UV, anisaldehyde), and tris[(carboxyethoxy)ethyl]aminomethane trimethyl ester[3] (1.35 g, 3.55 mmol, 1.0 eq.) and TEA (1 mL) were added. After 3 days, the disappearance of the raw material was confirmed by TLC (CHCl$_3$:MeOH=10:1, UV, ninhydrin). Water was added to the reaction solution to quench the reaction, and then the reaction solution was diluted with CH$_2$Cl$_2$ and subjected to liquid-liquid extraction with saturated sodium bicarbonate water three times. The organic layer was washed with brine, dried over anhydrous sodium sulfate, and distilled under reduced pressure. Then, flash column chromatography (hexane:ethyl acetate=1:2) was performed. A compound 57 (2.36 g, 3.26 mmol, 90%) was obtained as a white oil.

$^1$H NMR (400 MHz, CDCl$_3$) δ7.79-7.77 (d, J=8.2 Hz, 2H), 7.40-7.37 (d, J=8.7 Hz, 2H), 6.16 (br, 1H), 5.90 (s, 1H), 4.40 (s, 2H), 3.70-3.67 (m, 20H), 3.47-3.42 (q, J=6.7 Hz, 2H), 2.56-2.53 (t, J=6.2 Hz, 6H), 2.15-2.11 (t, J=7.6 Hz, 2H), 1.63-1.57 (m, 7H), 1.37-1.24 (m, 20H).

[Chemical Formula 55]

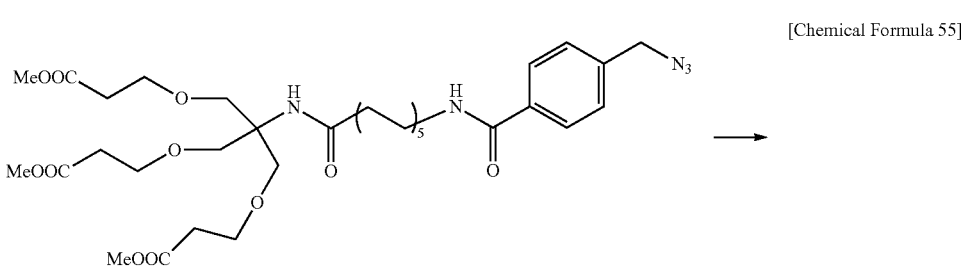

57

-continued

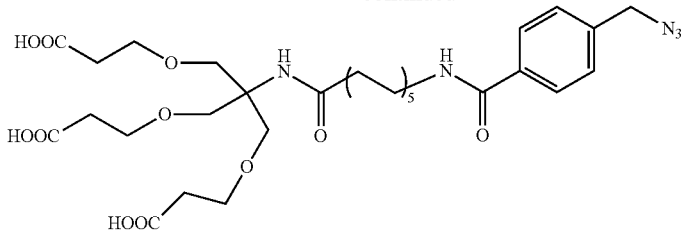

58

Synthesis of Compound 58

The compound 57 (2.25 g, 3.12 mmol) was dissolved in acetone (78 mL), and 0.4 M NaOH aq. (78 mL) was added with ice cooling. The reaction solution was returned to room temperature and stirred. After 1 day, the disappearance of the raw material was confirmed by TLC (CHCl$_3$:MeOH=10:1, UV, anisaldehyde), and acetone was distilled off under reduced pressure. The aqueous layer was washed with CH$_2$Cl$_2$, and then HCl was added with ice cooling until pH<2. Extraction with CH$_2$Cl$_2$ was performed to obtain a desired compound 58 (1.85 g, 2.72 mmol, 87%) as a white oil.

$^1$H NMR (400 MHz, DMSO-d6) δ12.21 (br, 1H), 8.53-8.50 (t, J=5.9 Hz, 1H), 7.92-7.90 (d, J=8.3 Hz, 2H), 7.51-7.49 (d, J=8.3 Hz, 2H), 6.98 (s, 1H), 4.58 (s, 2H), 3.39-3.23 (m, 16H), 2.60-2.56 (m, 24H), 2.11-2.07 (t, J=7.3 Hz, 2H), 1.57-1.47 (m, 4H), 1.33-1.29 (m, 14H).

were dissolved in DMF (13 ml), and the solution was stirred at room temperature. After 10 hours, the disappearance of the raw material was confirmed by TLC (CHCl$_3$:MeOH=5:1, UV, anisaldehyde), and (3-aminopropyl)carbamic acid tert-butyl ester[3] (1.80 g, 10.31 mmol, 4.0 eq.) dissolved in CH$_2$Cl$_2$ (2 mL) was added. After 2 days, the progress of reaction was confirmed by TlC (CHCl$_3$:MeOH=10:1, UV, ninhydrin). Water was added to the reaction solution to quench the reaction, and the precipitate was removed. The reaction solution was diluted with EtOAc and subjected to liquid-liquid extraction with saturated bicarbonate water three times. The organic layer was washed with brine, dried over anhydrous sodium sulfate, and distilled under reduced pressure. Then, flash column chromatography (CHCl$_3$:CH$_3$OH 10:1) was performed. A compound 59 (2.07 g, 1.80 mmol, 69%) was obtained as a white oil.

$^1$H NMR (400 MHz, CDCl$_3$) δ7.83-7.81 (d, J=8.3 Hz, 2H), 7.39-7.37 (d, J=7.8 Hz, 2H), 6.98 (br, 3H), 6.68 (br, 1H), 6.37 (s, 1H), 5.38-5.35 (t, J=6.1 Hz, 3H), 4.40 (s, 2H),

[Chemical Formula 56]

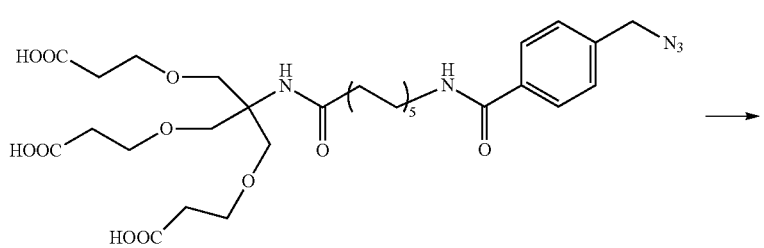

58

→

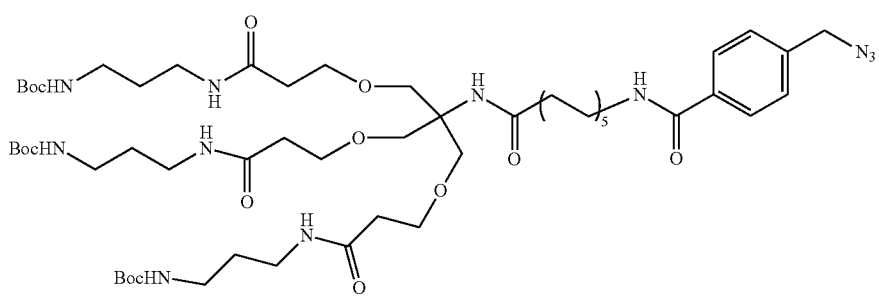

59

Synthesis of Compound 59

The compound 58 (1.76 g, 2.59 mmol), HOBt (1.41 g, 10.45 mmol, 4.0 eq.), and DCC (2.79 g, 13.53 mmol, 5.2 eq.)

3.46-3.41 (q, J=6.7 Hz, 2H), 3.32-3.27 (q, J=6.2 Hz, 6H), 3.17-3.12 (q, J=5.9 Hz, 6H), 2.44-2.41 (t, J=5.7 Hz, 6H), 2.19-2.16 (t, J=7.3 Hz, 2H), 1.64-1.57 (m, 12H), 1.43-1.35 (m, 35H), 1.27-1.07 (m, 16H).

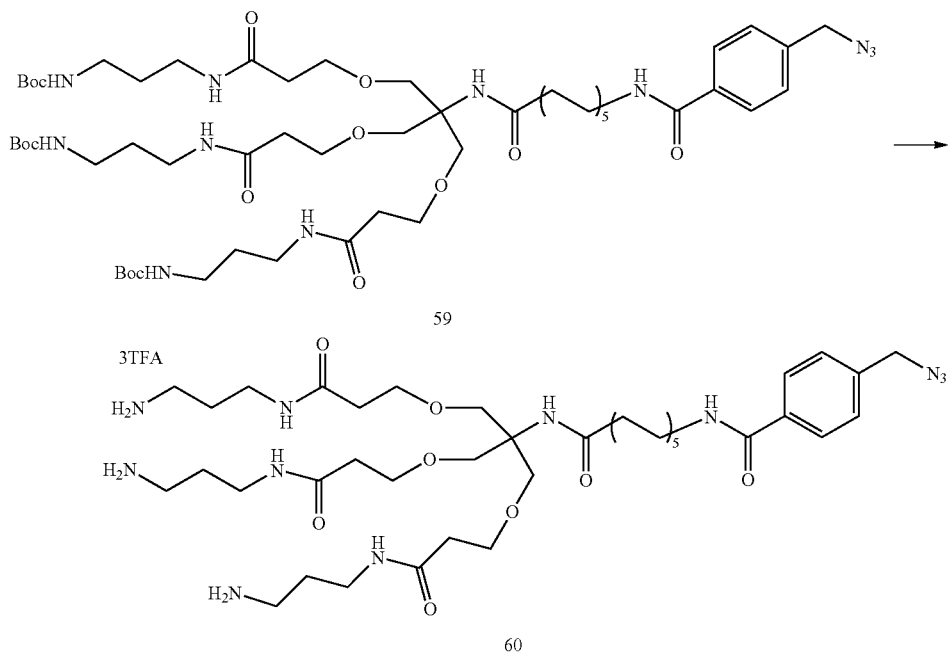

Synthesis of Compound 60

The compound 59 (1.99 g, 1.73 mmol) was dissolved in CH$_2$Cl$_2$ (10 mL), TFA (2 mL) was added, and the mixture was stirred at room temperature. After 4 hours, the disappearance of the raw material was confirmed by TLC (CHCl$_3$: MeOH=5:1, UV, anisaldehyde). The solvent was distilled off under reduced pressure to quantitatively obtain a desired compound 60 as a white oil.

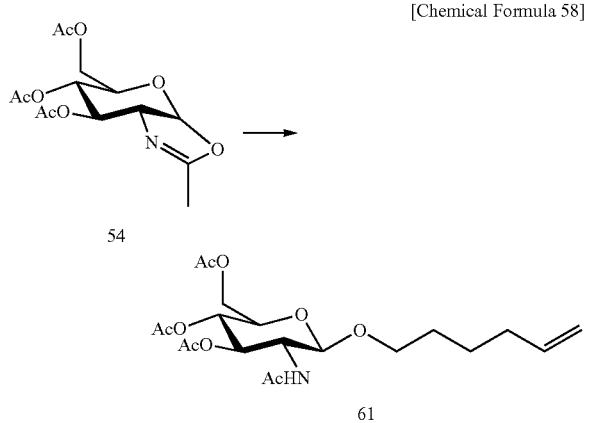

Synthesis of Compound 61

Under an Ar purge, oxazoline 54 (0.96 g, 2.91 mmol) was dissolved in CH$_2$Cl$_2$ (7 mL), 5-hexen-1-ol (0.4 mL, 3.39 mmol, 1.2 eq.) and molecular sieves 4A (1.04 g) were added, and the mixture was stirred. After 30 minutes, trimethylsilyl trifluoromethanesulfonate (0.3 mL, 1.64 mmol, 0.6 eq.) was added dropwise, and the mixture was stirred. After 15 hours, the disappearance of the raw material was confirmed by TLC (EtOAc, 5% sulfuric acid in MeOH). The reaction solution was subjected to suction filtration using CH$_2$Cl$_2$, and the filtrate was diluted with CH$_2$Cl$_2$ and subjected to liquid-liquid extraction with saturated sodium hydrogen carbonate. The organic layer was washed with distilled water and dried over anhydrous sodium sulfate, and the solvent was distilled off under reduced pressure. The residue was purified by column chromatography (hexane:EtOAc 1=1:1→1:2) to obtain a compound 61 (0.98 g, 79%) as a white powder.

$^1$H-NMR (400 MHz, CDCl$_3$) δ: 5.81-5.74 (m, 1H), 5.45-5.43 (d, 1H, J=8.0 Hz), 5.33-5.28 (t, 1H, J=10.0 Hz), 5.09-4.93 (m, 3H), 4.69-4.67 (d, 1H, J=8.0 Hz), 4.28-4.21 (m, 1H), 4.14-4.11 (m, 1H), 3.99-3.77 (m, 2H), 3.71-3.67 (m, 1H), 3.48-3.46 (m, 1H), 2.08-1.90 (m, 14H), 1.64-1.52 (m, 2H), 1.47-1.35 (m, 2H).

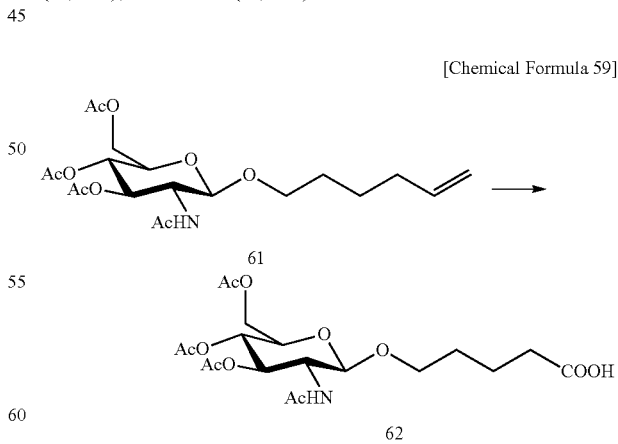

Synthesis of Compound 62

The compound 61 (2.58 g, 6.00 mmol) was dissolved in MeCN:CH$_2$Cl$_2$=1:1 (15 mL), NaIO$_4$/H$_2$O (5.13 g, 24.0 mmol, 4.0 eq.)/(12 mL) was added at 10° C., and the mixture was stirred. After 15 minutes, RuCl₃ (55.5 mg, 0.12 mmol, 0.02 eq.) was added. After 1 hour, NaIO₄ (1.30 g, 6.00 mmol, 1.0 eq.) was added. After 1.5 hours, the disappearance of the raw material was confirmed by TLC (CHCl₃:CH₃OH 5:1, 5% sulfuric acid in MeOH). A saturated aqueous sodium hydrogen carbonate solution was added to adjust the pH>7.0. Then, the reaction solution was diluted with CH₂Cl₂ and subjected to extraction. The aqueous layer was adjusted to pH<7.0 with 5% citric acid. Then, the aqueous layer was diluted with CH₂Cl₂ and subjected to extraction. The organic layer was dried over anhydrous sodium sulfate. Then, the solvent was distilled off under reduced pressure to obtain a compound 62 (1.73 g, 65%) as a white crystal.

¹H-NMR (400 MHz, CDCl₃) δ: 5.80-5.78 (d, 1H, J=8.8 Hz), 5.29-5.25 (t, 1H, J=7.6 Hz), 5.08-5.04 (t, 1H, J=9.6 Hz), 4.239-4.228 (m, 1H), 4.14-4.10 (m, 1H), 3.91-3.83 (m, 2H), 3.70-3.66 (m, 1H), 3.52-3.47 (m, 1H), 2.42-2.32 (m, 2H), 2.08-1.71 (t, 12H, J=14.0 Hz), 1.71-1.62 (m, 4H).

added. After 3 days, the disappearance of the intermediate was confirmed by TLC (CHCl₃:MeOH=5:1, UV, ninhydrin). Water was added to the reaction solution to quench the reaction, and the precipitate was removed. The reaction solution was diluted with CH₂Cl₂ and subjected to liquid-liquid extraction with saturated sodium bicarbonate water three times. The organic layer was washed with brine, dried over anhydrous sodium sulfate, and distilled under reduced pressure. Then, flash column chromatography (CHCl₃:CH₃OH=5:1) was performed. A compound 63 (1.14 g, 0.53 mmol, 83%) was obtained as a white foam. ¹H NMR (400 MHz, CDCl₃) δ$_H$=7.86-7.84 (d, J=8.2 Hz, 2H), 7.41-7.38 (d, J=11.5 Hz, 2H), 7.32-7.29 (t, J=6.6 Hz, 3H), 7.10-7.06 (t, J=8.0 Hz, 3H), 6.98-6.91 (m, 4H), 6.61 (s, 1H), 5.31 (s, 1H) 5.29-5.24 (t, J=9.9 Hz, 3H), 5.08-5.03 (t, J=9.6 Hz, 3H), 4.66-4.64 (d, J=8.2 Hz, 2H), 4.41 (s, 2H), 4.30-4.25 (dd, J=17.0, 5.0 Hz, 3H), 4.14-4.10 (d, 14.7 Hz, 3H), 3.95-3.88 (m, 5H), 3.72-3.68 (m, 15H), 3.53-3.42 (m, 4H), 3.27-3.21

[Chemical Formula 60]

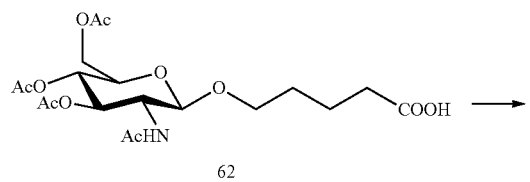

62

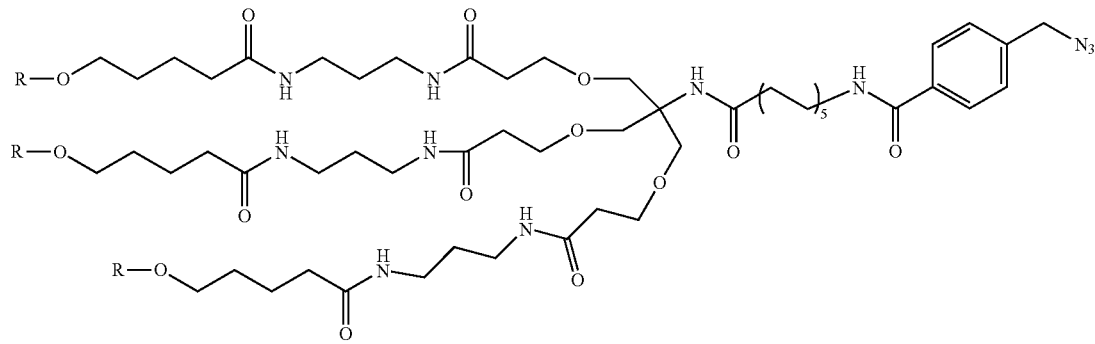

63

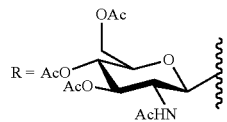

Synthesis of Compound 63

The compound 62 (0.86 g, 1.93 mmol), HOBt (0.34 g, 2.51 mmol, 1.3 eq.), DCC (0.64 g, 3.11 mmol, 1.6 eq.) were dissolved in CH₂Cl₂ (10 mL), and the solution was stirred at room temperature. After 17 hours, the disappearance of the raw material was confirmed by TLC (CHCl₃:CH₃OH=10:1, UV, anisaldehyde). The compound 60 (0.93 g, 0.78 mmol, 0.4 eq.) dissolved in pyridine (10 mL) and TEA (1 mL) were (m, 12H), 2.48-2.43 (t, J=8.8 Hz, 6H), 2.26-2.15 (m, 8H), 2.09 (s, 9H, 2.02 (s, 18H), 1.94 (s, 9H), 1.76-1.58 (m, 22H), 1.35-1.27 (m, 12H).

¹³C NMR (100 MHz, CDCl₃) δ173.98, 173.61, 171.94, 170.88, 170.67, 170.49, 169.43, 167.16, 138.66, 134.60, 128.11, 127.58, 100.59, 72.59, 71.54, 69.59, 69.41, 68.83, 67.40, 62.16, 59.50, 54.33, 54.11, 53.48, 40.14, 37.04, 36.66, 36.02, 35.89, 29.52, 29.45, 29.26, 29.15, 29.03, 28.27, 26.88, 25.70, 23.10, 22.53, 20.72, 20.64, 20.59.

[Chemical Formula 61]

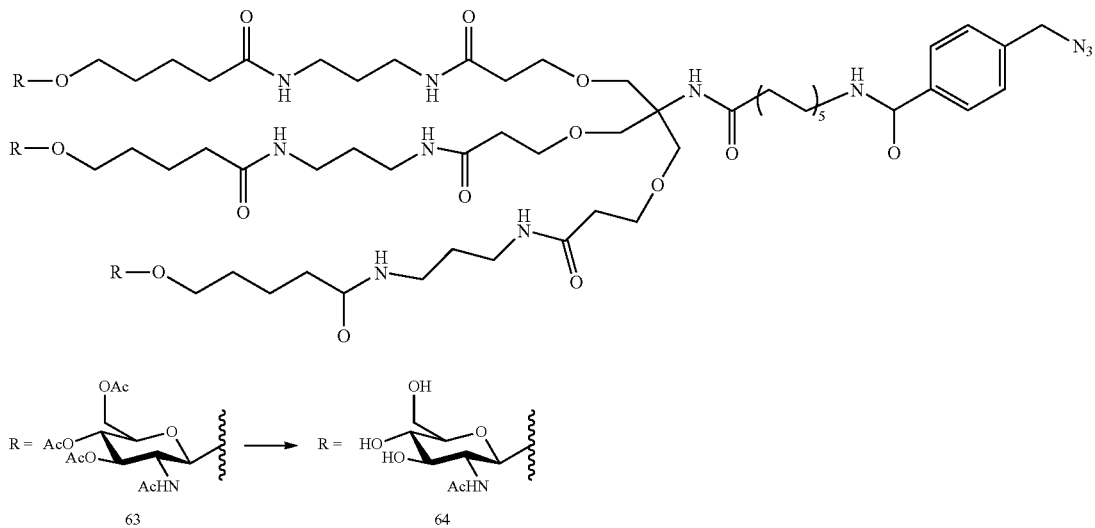

Synthesis of Compound 64

The compound 63 (0.21 g, 0.10 mmol) was dissolved in 2 mL of dry MeOH, sodium methoxide (6.4 mg, 0.12 mmol) was added, and the mixture was stirred. On the next day, the completion of reaction was confirmed by TLC ($CHCl_3$: MeOH=5:1, UV, 5% $H_2SO_4$ in EtOH), and then the reaction solution was neutralized by adding DOWEX 50 WX8-100 ion-exchange resin. The reaction solution was filtered through a cotton plug and concentrated under reduced pressure. A compound 64 (0.17 g, 0.10 mmol, 96%) was obtained as a white foam.

$^1$H NMR (400 MHz, DMSO-d6) $\delta_H$=8.47-8.44 (t, J=5.7 Hz, 1H), 7.85-7.83 (m, 5H), 7.75-7.72 (t, J=5.5 Hz, 31H), 7.68-7.66 (d, J=9.2 Hz, 3H) 7.44-7.43 (d, J=8.2 Hz, 2H), 7.26 (br, 1H), 6.99 (s, 1H), 4.96-4.95 (d, J=4.1 Hz, 3H), 4.89-4.88 (d, J=5.0 Hz, 3H), 4.54-4.50 (m, 5H), 4.24-4.22 (d, J=8.4 Hz, 3H), 4.10-4.08 (m, 1H), 3.72-3.64 (m, 6H), 3.54-3.51 (m, 12H), 3.45-3.15 (m, 30H), 3.07-3.00 (m, 19H), 2.28-2.25 (t, J=6.8 Hz, 6H), 2.05-2.01 (t, J=7.1 Hz, 8H), 1.78 (s, 9H), 1.51-1.40 (m, 24H), 1.26-1.22 (m, 12H).

$^{13}$C NMR (100 MHz, $CD_3OD$) $\delta$176.41, 176.09, 173.98, 173.71, 129.37, 128.74, 102.65, 77.98, 76.11, 72.11, 70.10, 68.66, 62.80, 57.35, 54.97, 41.08, 37.90, 37.82, 37.65, 36.73, 30.66, 30.47, 30.37, 30.27, 29.97, 28.11, 27.08, 23.76, 23.11, 22.06.

[Chemical Formula 62]

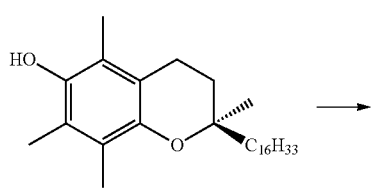

-continued

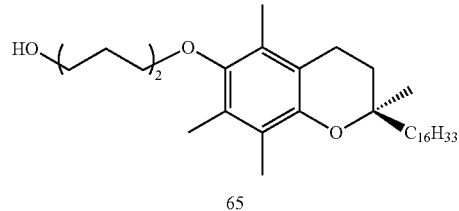

Synthesis of Compound 65

Tocopherol (864 mL, 2.01 mmol) was dissolved in acetone (20 mL). Then, 6-bromo-1-hexanol (816 μL 6.03 nmol) and potassium carbonate (829 mg, 6.03 mmol) were added thereto, and the mixture was refluxed at 76° C. After 48 hours, the completion of reaction was confirmed by TLC, and then acetone was distilled off under reduced pressure. The obtained residue was subjected to extraction with distilled water and ethyl acetate, and the organic layer was washed with brine and dried over anhydrous sodium sulfate. Then, the organic layer was distilled under reduced pressure using an evaporator. The obtained residue was purified by silica gel column chromatography (hexane:EtOAc=8:1). A compound 65 (855 mg, 1.61 mmol, 80%) was obtained as a yellow oil.

[Chemical Formula 63]

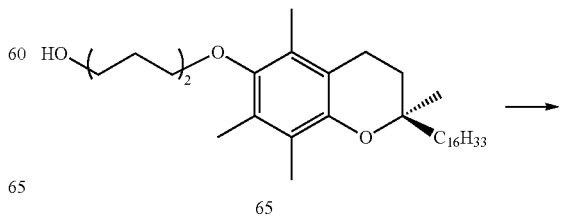

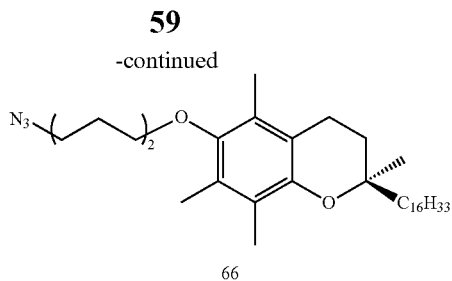

66

Synthesis of Compound 66

The compound 65 (367 mg, 0.69 mmol) was dissolved in DMF (7 mL) under an argon atmosphere. Triphenylphosphine (239 mg, 0.91 mmol), sodium azide (228 mg, 3.51 mmol), and carbon tetrabromide (348 mg, 1.05 mmol) were added, and the mixture was well stirred. After 48 hours, the completion of reaction was confirmed by TLC. Then, the reaction solution was subjected to extraction with distilled water and ethyl acetate, and then the organic layer was washed with brine and dried over anhydrous sodium sulfate. Then, the organic layer was distilled under reduced pressure using an evaporator, and the obtained residue was purified by neutral silica gel column chromatography (hexane:EtOAc=200:1→100:1→50:1→20:1). A compound 66[4] (257 mg, 0.46 mmol, 67%) was obtained as a white powder.

[Chemical Formula 64]

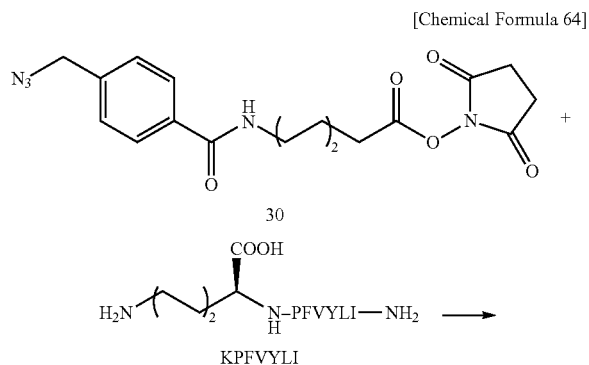

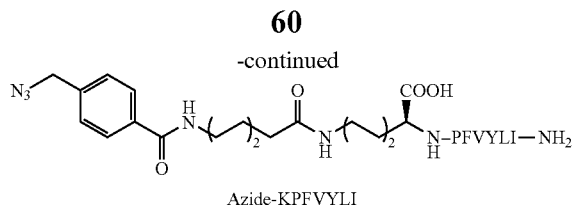

Azide-KPFVYLI

Synthesis of Azide-KPFVYLI

A peptide KPFVYLI (2.1 mg, 3 μmol) was placed in a vial, and dissolved in HEPES buffer (250 μL, pH 8.5). The compound 30 (1.3 mg, 3 μmol) dissolved in DMSO (25 μL) was added, and the mixture was stirred at room temperature. MeCN (about 100 μL) was added until the precipitated compound 30 was dissolved, and the solution was further stirred at room temperature for 4 hours. The completion of reaction was confirmed by TLC (developing solvent $CHCl_3$:MeOH=1:1, 1% $NH_4OH$, detection with UV and ninhydrin), and then the solvent was distilled off under reduced pressure. The obtained residue was washed with a mixture of MeCN/$H_2O$=1:1 (10 mL). Centrifugation (4300 rpm×15 min, 4° C.) was performed to obtain a precipitate, and azide-KPFVYLI was quantitatively obtained as a white powder from the precipitate.

MALDI-TOF/MS calcd for $C_{60}H_{86}N_{12}O_{11}$ $[M+H]^+$ 1151.7, found 1151.9.

[Chemical Formula 65]

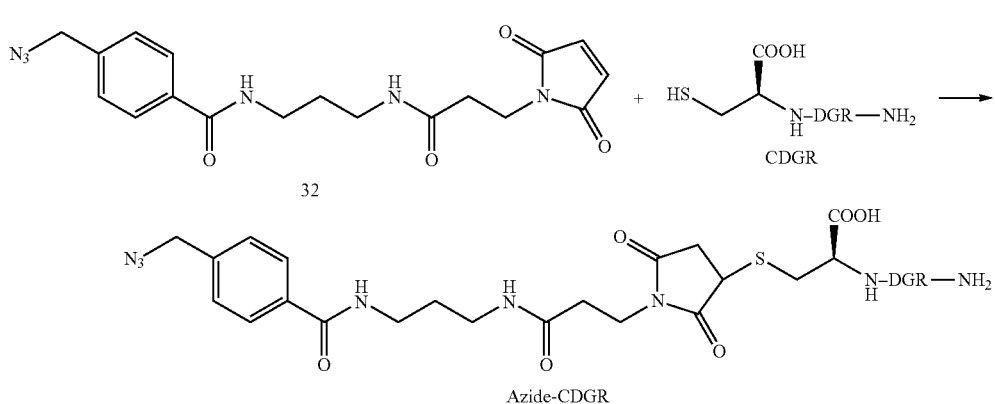

Azide-CDGR

Synthesis of Azide-CDGR

A peptide CDGR (13 mg, 30 μmol) and the compound 32 (17 mg, 45 μmol) were placed in a 5 mL eggplant flask and dissolved in MeCN (1 mL) and $H_2O$ (0.5 mL). TEA (6 μL) and TCEP.HCl (0.4 mg) were added, and the mixture was stirred for 8 hours. Then, the reaction solution was purified by HPLC.

The solvent of the fractionated solution was distilled off under reduced pressure. MeCN was added to the obtained residue, and then ultrasonic treatment was performed to precipitate a crystal. Centrifugation (4300 rpm×15 min, 4° C.) was performed to obtain a precipitate, and azide-CDGR (3 mg, 4 μmol, 12%) was obtained as a white powder from the precipitate. MALDI-TOF/MS calcd for $C_{33}H_{47}N_{13}O_{11}S$ $[M+H]^+$ 834.3, found v 834.2.

Click Reaction Between Compound 19 and RNA

Figure 10:
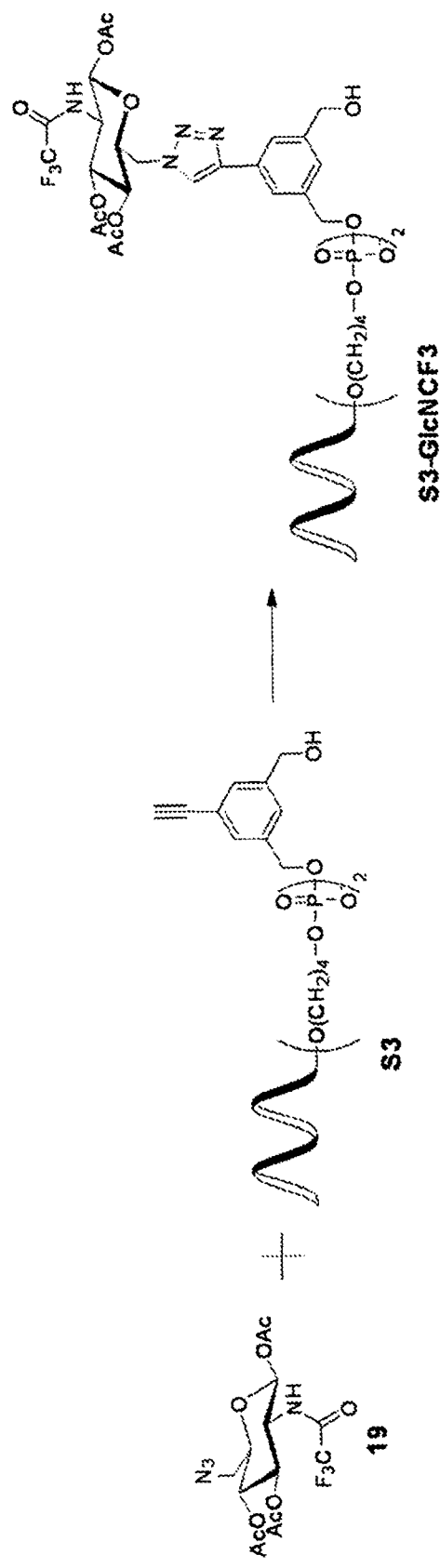
FIG. 10 illustrates click reaction between compound 19 and RNA.

The S3 (0.5 mM solution in $H_2O$, 1 μL, 0.5 nmol) and the compound 19 (5 mM solution in DMSO, 3 μL, 15 nmol) were added to sterilized 1 M phosphate buffer (pH 7.0) (1

μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in H$_2$O, 1 μL, 25 nmol) were added in order, and the mixture was vortexed for about 1 minute and allowed to stand at 37° C. for 15 minutes. The reaction solution was purified by HPLC to obtain a desired product (S3-GlcNCF3). (See FIG. 10)

MALDI-TOF/MS calcd for 6846.0, found 6843.5.

Click Reaction Between Compound 38 and RNA

Figure 11:
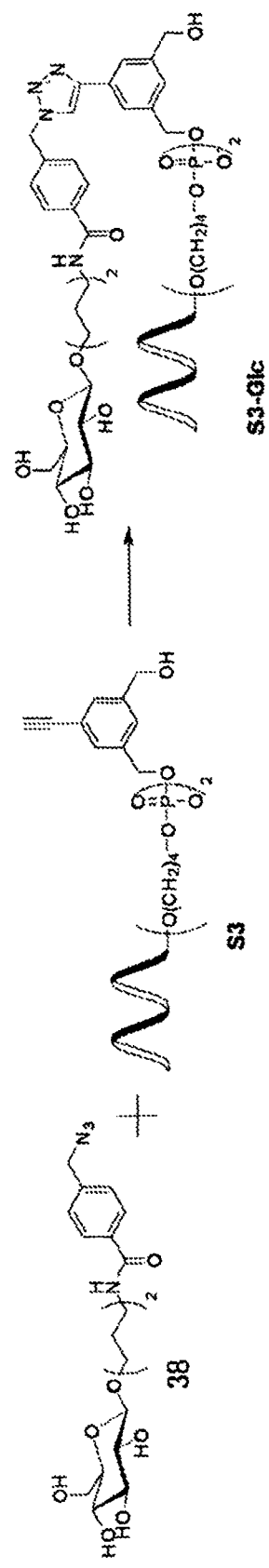
FIG. 11 illustrates click reaction between compound 38 and RNA.

The S3 (0.5 mM solution in H$_2$O, 1 μL, 0.5 nmol), and the compound 38 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in H$_2$O, 1 μL, 25 nmol) were added in order, and the mixture was vortexed for about 1 minute and allowed to stand at 37° C. for 15 minutes. The reaction solution was purified by HPLC to obtain a desired product (S3-C6Glc deAc). (See FIG. 11) MALDI-TOF/MS Calcd for 6858.1, Found 6857.9.

Click Reaction Between Compound 50 and RNA

Figure 12:
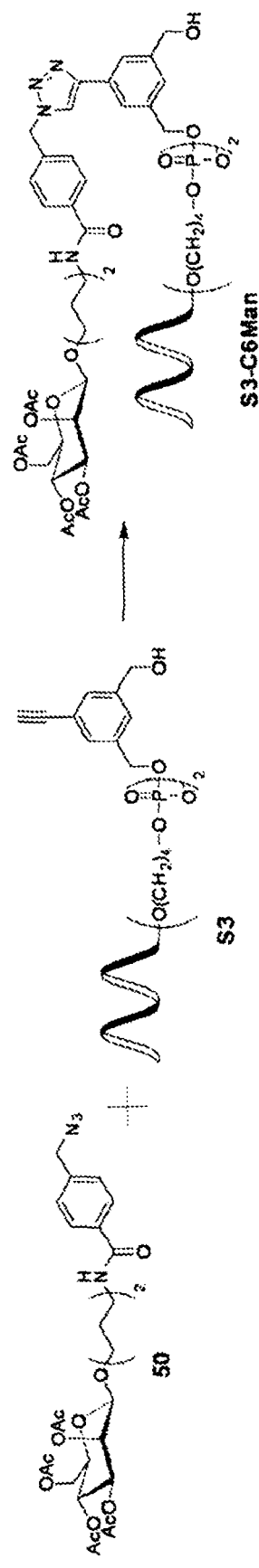
FIG. 12 illustrates click reaction between compound 50 and RNA.

The S3 (0.5 mM solution in H$_2$O, 1 μL, 0.5 nmol) and the compound 50 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in H$_2$O, 1 μL, 25 nmol) were added in order, and the mixture was vortexed for 1 minute and allowed to stand at 37° C. for 15 minutes. The reaction solution was purified by HPLC to obtain a desired product (S3-C6Man). (See FIG. 12)

MALDI-TOF/MS calcd for 7026.1, found 7027.5.

Click Reaction Between Compound 52 and RNA

Figure 13:
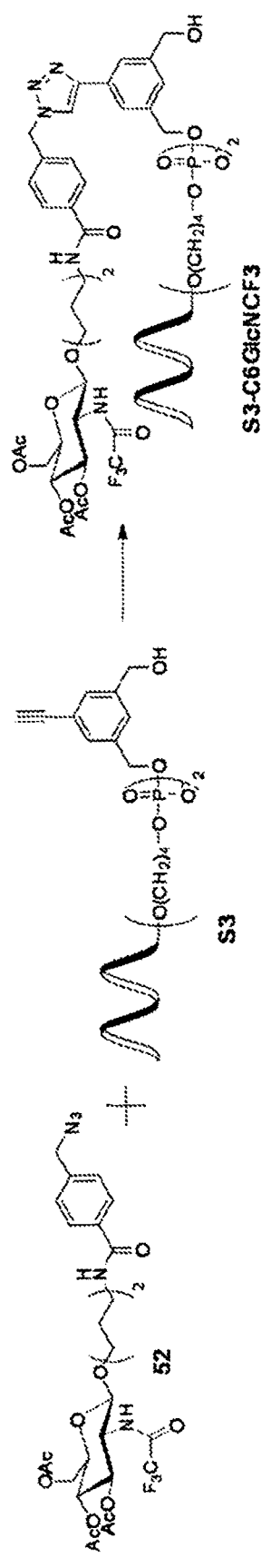
FIG. 13 illustrates click reaction between compound 52 and RNA.

The S3 (0.5 mM solution in H$_2$O, 1 μL, 0.5 nmol) and the compound 52 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in H$_2$O, 1 μL, 25 nmol) were added in order, and the mixture was vortexed for about 1 minute and allowed to stand at 37° C. for 15 minutes. The reaction solution was purified by HPLC to obtain a desired product (S3-C6GlcCF$_3$). (See FIG. 13)

MALDI-TOF/MS calcd for 7079.1, found 7075.2.

Click Reaction Between Compound 53 and RNA

Figures 14, 15:
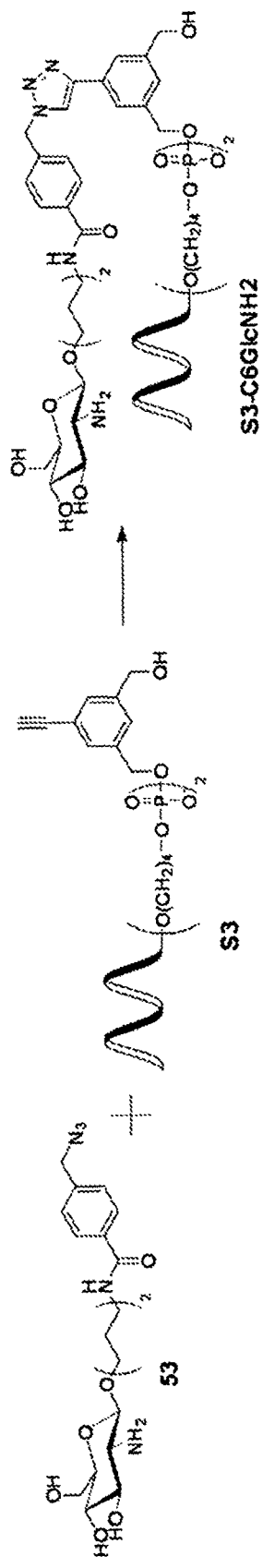
FIG. 14 illustrates click reaction between compound 53 and RNA.
FIG. 15 illustrates click reaction between compound 55 and RNA.

The S3 (0.5 mM solution in H$_2$O, 1 μL, 0.5 nmol) and the compound 53 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in H$_2$, 1 μL, 25 nmol) were added in order, and the mixture was vortexed for about 1 minute and allowed to stand at 37° C. for 15 minutes. The reaction solution was purified by HPLC to obtain a desired product (S3-C6GlcNH$_2$). (See FIG. 14)

MALDI-TOF/MS calcd for 6857.1, found 6861.5.

Click Reaction Between Compound 55 and RNA

The S3 (0.5 mM solution in H$_2$O, 1 μL, 0.5 nmol) and the compound 55 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in H$_2$O, 1 μL, 25 nmol) were added in order, and the mixture was vortexed for about 1 minute and allowed to stand at 37° C. for 15 minutes. The reaction solution was purified by HPLC to obtain a desired product (S3-C6GlcNAc). (See FIG. 15)

MALDI-TOF/MS calcd for 7025.1, found 7031.0.

Click Reaction Between Compound 56 and RNA

Figure 16:
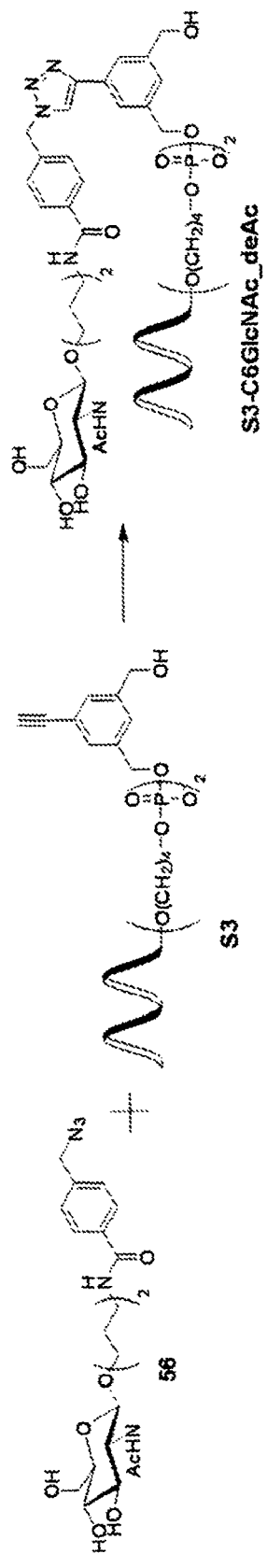
FIG. 16 illustrates click reaction between compound 56 and RNA.

The S3 (0.5 mM solution in H$_2$O, 1 μL, 0.5 nmol) and the compound 56 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in 20, 1 μL, 25 nmol) were added in order, and the mixture was vortexed for about 1 minute and allowed to stand at 37° C. for 15 minutes. The reaction solution was purified by HPLC to obtain a desired product (S3-C6GlcNAc deAc). (See FIG. 16)

MALDI-TOF/MS calcd for 6899.1, found 6901.1.

Click Reaction Between Compound 63 and RNA

Figure 17:
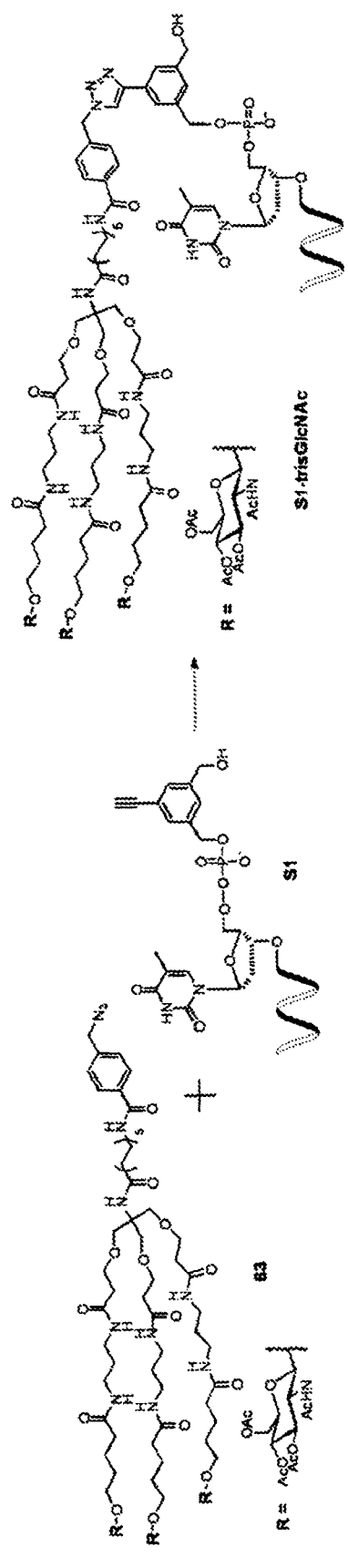
FIG. 17 illustrates click reaction between compound 63 and RNA.

The S1 (0.5 mM solution in H$_2$O, 1 μL, 0.5 nmol) and the compound 63 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$, 1 μL, 25 nmol) and copper sulfate pentahydrate (25 mM solution in H$_2$O, 1 μL, 25 nmol) were added in order, and the mixture was vortexed for about 1 minute and allowed to stand at 37° C. for 15 minutes. The reaction solution was purified by HPLC to obtain a desired product (S1-trisGlcNAc). (See FIG. 17)

MALDI-TOF/MS calcd for 8554.9, found 8551.4.

Click Reaction Between Compound 64 and RNA

Figure 18:
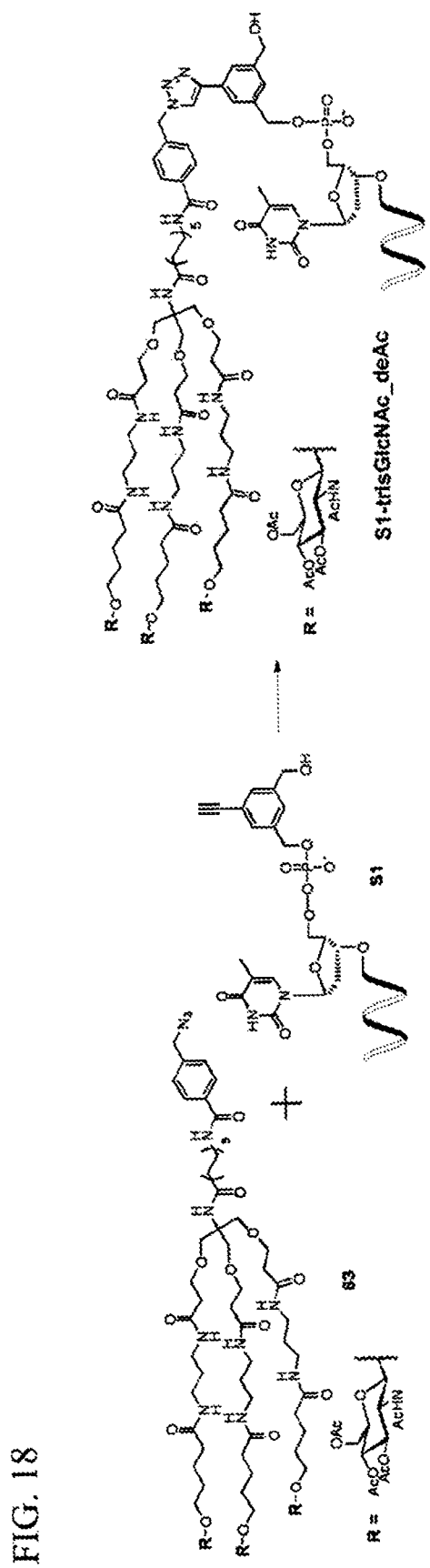
FIG. 18 illustrates click reaction between compound 64 and RNA.

The S1 (0.5 mM solution in H$_2$O, 1 μL, 0.5 nmol) and the compound 64 (5 mM solution in DMSO, 3 μL, 15 nmol) were added to sterilized 1 M phosphate buffer (pH 7.0) (1 μL) and sterilized water (3 μL) in an Eppendorf tube, and the mixture was vortexed for about 1 minute. Then, sodium ascorbate (25 mM solution in H$_2$O, 1 μL, 25 nmol) and copper sulfate pentahydrate (25 mM solution in H$_2$O, 1 μL, 25 nmol) were added in order, and the mixture was vortexed for about 1 minute and allowed to stand at 37° C. for 15 minutes. The reaction solution was purified by HPLC to obtain a desired product (S1-trisGlcNAc_deAc). (See FIG. 18)

MALDI-TOF/MS calcd for 8176.8, found 8173.4.

Click Reaction Between Azide-CDRG and RNA

Figure 19:
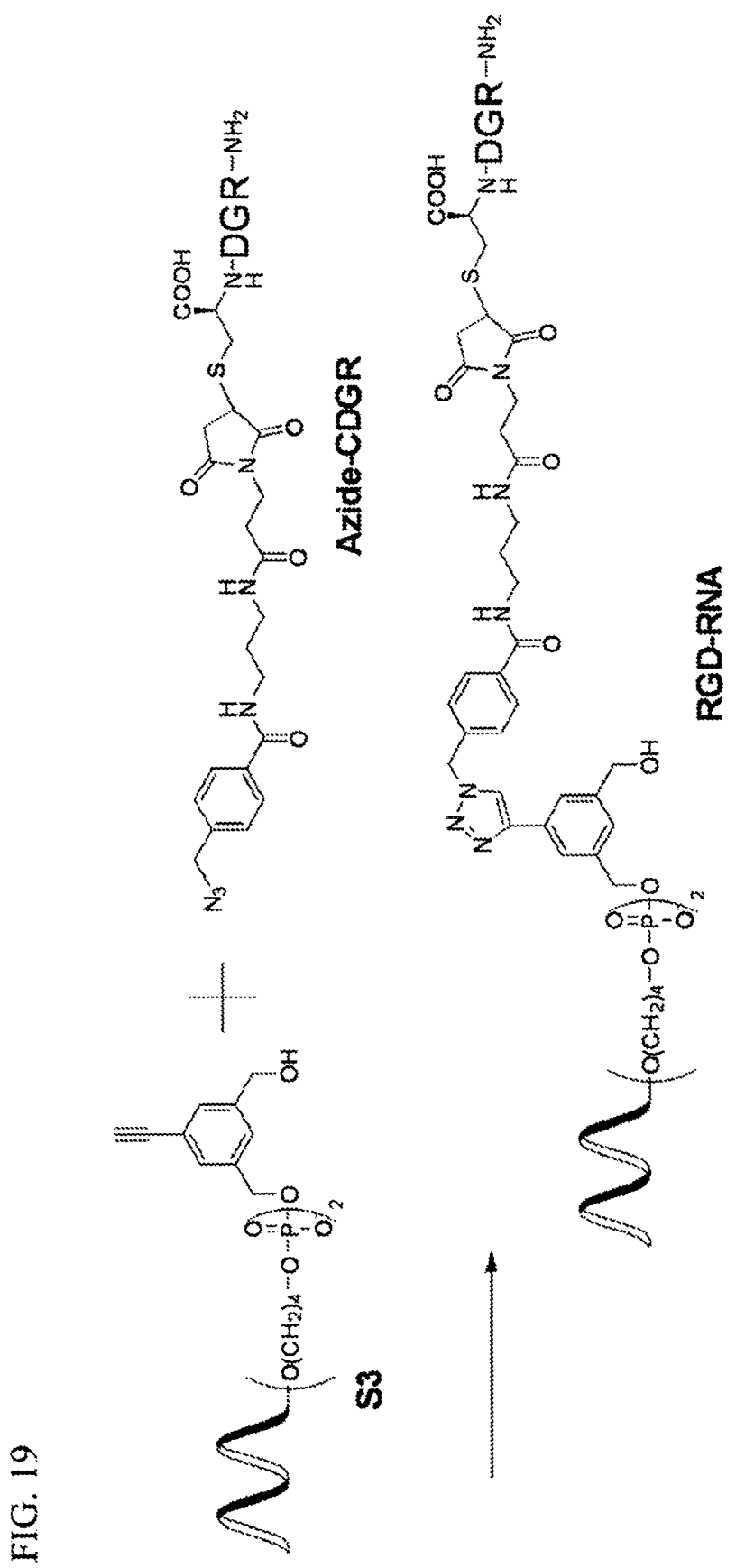
FIG. 19 illustrates click reaction between Azide-CDRG and RNA.

The S3 (0.5 mM solution in H$_2$O, 2 μL, 1 nmol), the Azide-CDGR (15 mM solution in DMSO, 1 μL, 15 nmol), and acetonitrile (1.0 μL) were added to sterilized 1 M phosphate buffer (pH 7.0) (1.0 μL) and sterilized water (3 μL) in an Eppendorf tube, and the mixture was vortexed for about 1 minute. Then, sodium ascorbate (50 mM solution in H$_2$O, 1 μL, 50 nmol) and copper sulfate pentahydrate (50 mM solution in 1420, 1 μL, 50 nmol) were added in order, and the mixture was vortexed for about 1 minute and allowed to stand at room temperature for 15 minutes. The reaction solution was subjected to centrifugal filtration (15000×g, 15 min, 4° C.) using Amicon Ultra (3K) to obtain desired RGD-RNA. (See FIG. 19)

MALDI-TOF/MS calcd for 7277.2, found 7277.5.

Uptake of Modified RNA Duplex into Cells

The sugar- or RGD peptide-modified RNA and RNA having a fluorescein-modified 5' end were annealed in PBS buffer to form a duplex.

The modified RNA duplex was dissolved in OPTI-MEM to a final concentration of 400 nM, and the solution was added to HeLa cells. A positive control was also prepared by introducing an unmodified fluorescein-labeled RNA duplex (final concentration: 100 nM) into HeLa cells using Trans-Fast (Promega). A negative control was also prepared by adding, to HeLa cells, a solution obtained by dissolving an unmodified fluorescein-labeled RNA duplex in OPTI-MEM to a final concentration of 400 nM. After 4 hours, uptake of the modified RNA duplex into HeLa cells was observed using a confocal microscope (LSM 710, Carl Zeiss).

Figure 5:
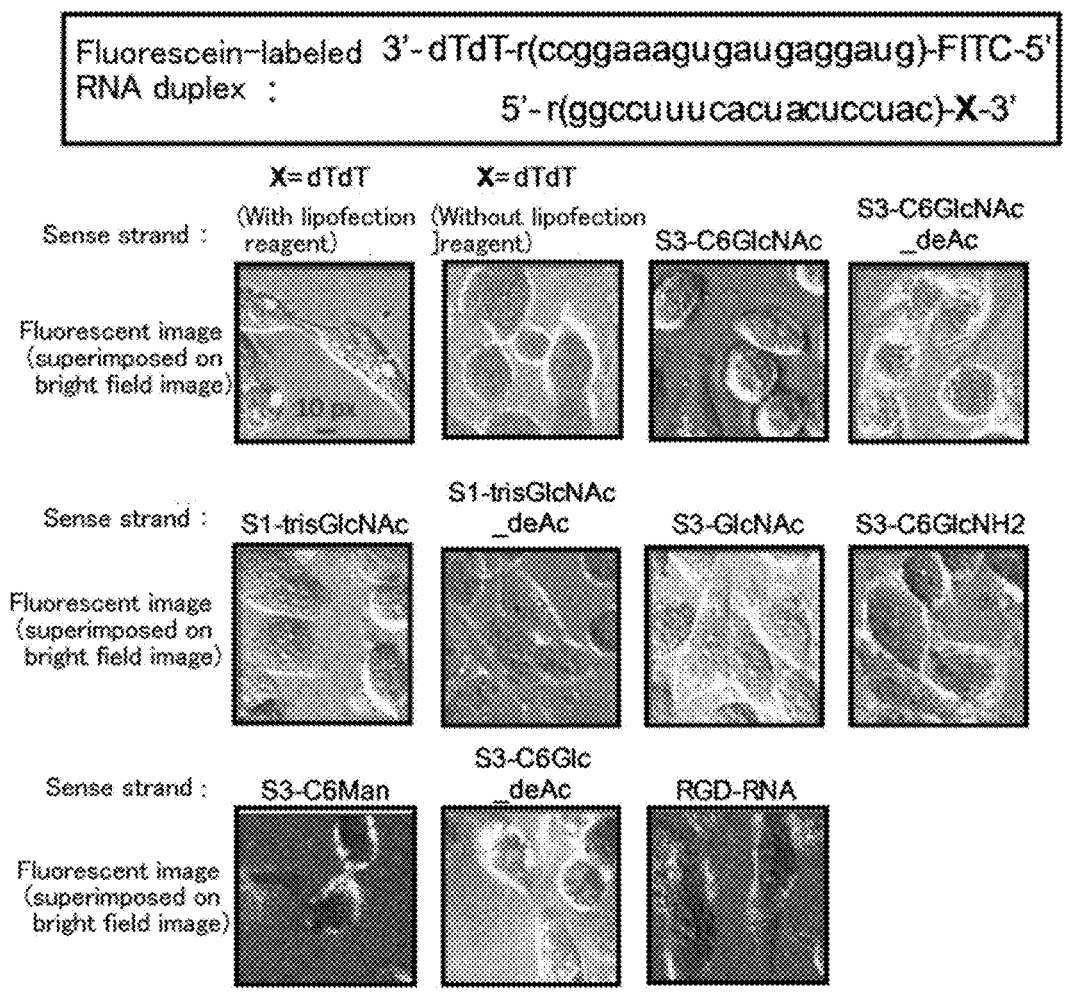
FIG. 5 shows photographs showing the observation results of uptake of duplexes of sugar- or RGD peptide-modified RNA and RNA having a fluorescein-modified 5' end and an unmodified fluorescein-labeled RNA duplex by HeLa cells with the use of a confocal microscope.

The results are shown in FIG. 5.

In the case of the positive control using a lipofection reagent, the green fluorescence of fluorescein of the fluorescein labeled-RNA duplex (X=dTdT) was observed in the cells. However, in the case of the negative control using no lipofection reagent, green fluorescence of the fluorescein-labeled RNA duplex (X=dTdT) was observed only outside the cells. On the other hand, when the sugar- or peptide-modified RNA duplex was used, green fluorescence was observed also in the cells as in the case of the positive control. This revealed that the sugar- or peptide-modified RNA duplex was taken into the cells even without a lipofection reagent.

REFERENCES

[1] a) J. Morel, Helv. Chim. Acta, 1958, 41, 1501-1504; b) S. Ogawa, H. Fujimori, T. Suami, Bull. Soc. Chim. Jpn., 1976, 49, 2585-2586.

[2] H. Y. Song, M. H. Ngai, Z. Y. Song. P. A. MacAry, J. Hobley and M. J. Lear, Org. Biomol. Chem., 2009, 7, 3400-3406.

[3] T. Machida, K. Lang, L. Xue, J. W. Chin and N. Winssinger, Bioconjugate Chem. 2015, 26, 802-806.

[4] L.-A. Jouanno, A. Chevalier, N. Sekkat, N. Perzo, H. Castel, A. Romieu, N. Lange, C. Sabot and P.-Y. Renard, J. Org Chem., 2014, 79, 10353-10366.

The present invention is not limited to the above embodiments and examples according to the present invention. Various modifications are also included in the present invention as long as they are readily conceivable by those skilled in the art and do not depart from the scope of claims.

INDUSTRIAL APPLICABILITY

According to the present invention, it is possible to provide a means using a nucleic acid oligomer which is useful in the medical field such as RNA drug discovery expected to be developed into personalized medicine.

SEQUENCE LISTING

PAF0039 Sequence Listing.txt

---

The invention claimed is:

1. An oligonucleotide derivative represented by the following formula (1): (wherein $R^1$ and $R^2$ each independently represent hydrogen or a phosphate group; a, b, and c are independently integers of 0 or more, and at least one of them is 1 or more; A and B are independently modified or unmodified oligonucleotides whose combined chain length is 3 or more, and A and B do not contain hydroxyl groups at 3' and 5' ends of the oligonucleotide; and $S_1$ is a substituent represented by the following (α)):

[Chemical Formula 1]

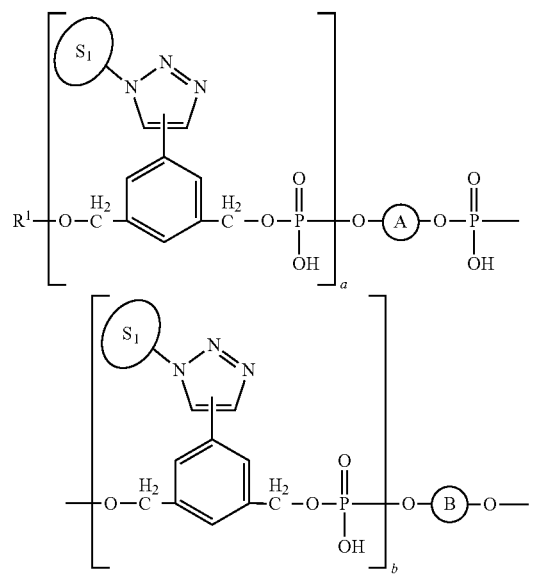

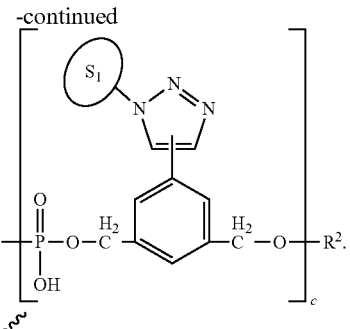

(1)

(α)

2. The oligonucleotide derivative according to claim 1, wherein the modified or unmodified oligonucleotides have a partial structure —$(CH_2)n$-, where n is a natural number of 1 or greater.

3. The oligonucleotide derivative according to claim 1, wherein $R^1$ and $R^2$ are H.

4. The oligonucleotide derivative according to claim 1, wherein b is 0.

5. The oligonucleotide derivative according to claim 1, wherein a and b are both 0.

6. The oligonucleotide derivative according to claim 1, wherein c is 1 or more and 5 or less.

7. The oligonucleotide derivative according to claim 1, wherein the combined chain length of A and B is 10 or more and 35 or less.

8. The oligonucleotide derivative according to claim 1, wherein A and B are oligoribonucleotides.

9. An oligonucleotide construct for regulating gene expression, comprising the oligonucleotide derivative according to claim 1, wherein the construct is selected from single- and double-stranded DNAs, single- and double-stranded RNAs, DNA/RNA chimeras, and DNA/RNA hybrids.

10. The construct according to claim 9, being selected from anti-genes, antisenses, aptamers, siRNAs, miRNAs, shRNAs, and ribozymes.

11. The construct according to claim 9, which has a unit represented by the following formula (4) or (5) at a dangling end (wherein $S_1$ is a substituent represented by the following ($\alpha$), letters "LINKER" surrounded by a rectangular frame represent a linker, $S_2$ is a substituent represented by the following ($\beta$), ($\gamma$), ($\delta$), or ($\epsilon$) bound to an end of the linker (two or more $S_2$s may be bound to the linker), and n represents a natural number of 0 to 4), or a peptide chain ($\epsilon$) having an amino acid sequence of RGD at its end.

12. The construct according to claim 11, being a siRNA wherein in the oligonucleotide derivative, a and b are 0, c is 1 or 2, and a unit represented by the following formula (4) or (5) is contained at a 3' dangling end (wherein $S_1$ is a substituent represented by the following ($\alpha$), letters "LINKER" surrounded by a rectangular frame represent a linker, $S_2$ is a substituent represented by the following ($\beta$), ($\gamma$), ($\delta$), or ($\epsilon$) bound to an end of the linker (two or more $S_2$s may be bound to the linker), and n represents a natural number of 0 to 4),

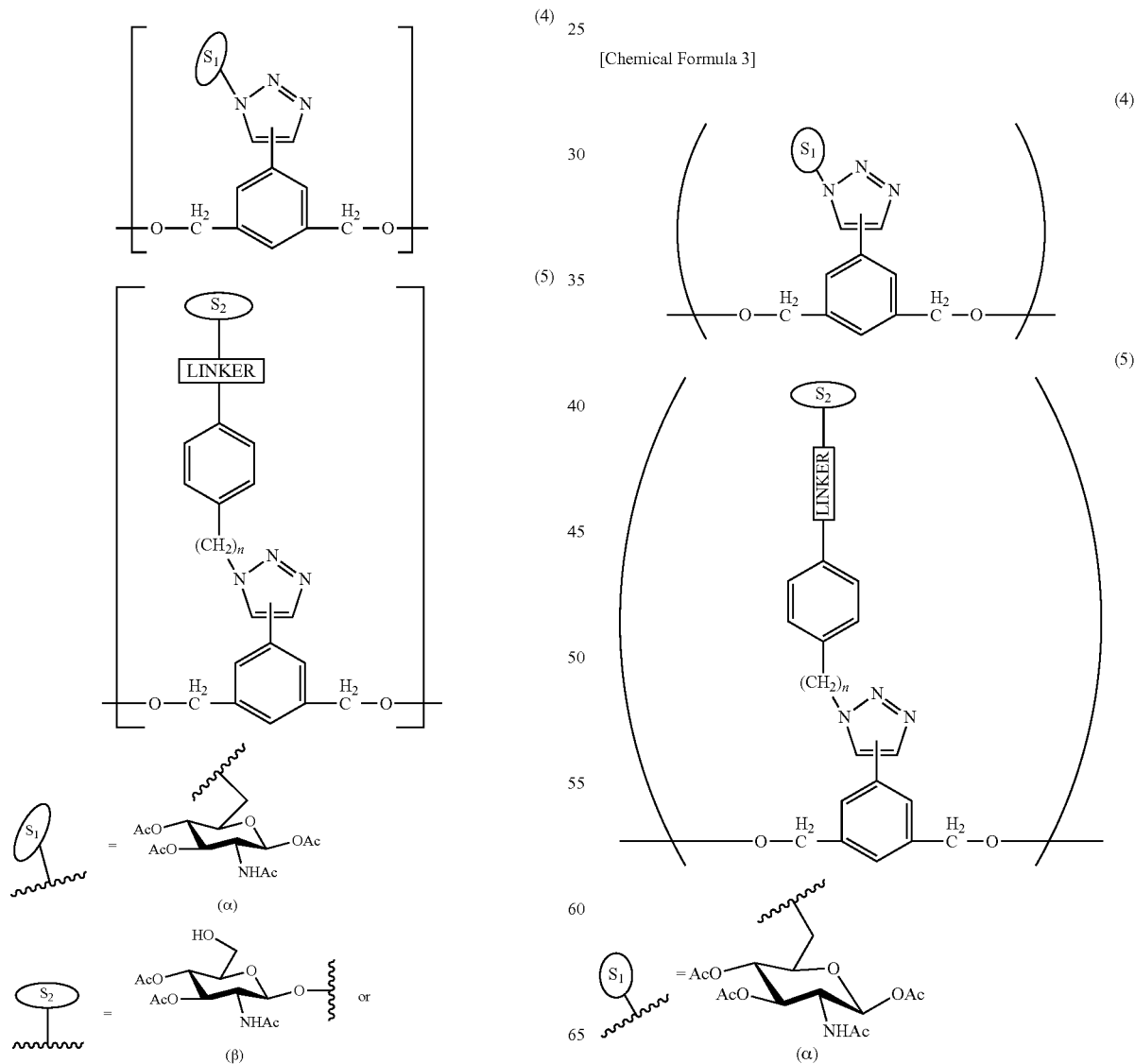

-continued

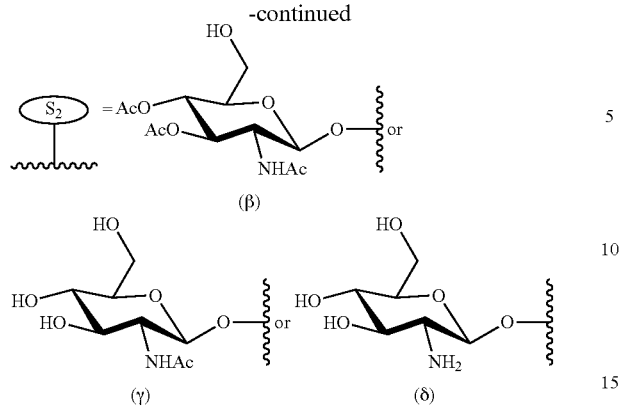

(β)

(γ)    (δ)

or a peptide chain (ε) having an amino acid sequence of RGD at its end.

13. An oligonucleotide derivative represented by the following formula (2): (wherein $R^1$ and $R^2$ each independently represent hydrogen or a phosphate group; a, b, and c are independently integers of 0 or more, and at least one of them is 1 or more; A and B are independently modified or unmodified oligonucleotides whose combined chain length is 3 or more, and A and B do not contain hydroxyl groups at 3' and 5' ends of the oligonucleotide; letters "LINKER" surrounded by a rectangular frame represent a linker; $S_2$ is a substituent represented by the following (β), (γ), (δ), or (ε) bound to an end of the linker (two or more $S_2$s may be bound to the linker); and n represents a natural number of 0 to 4:

[Chemical Formula 2]
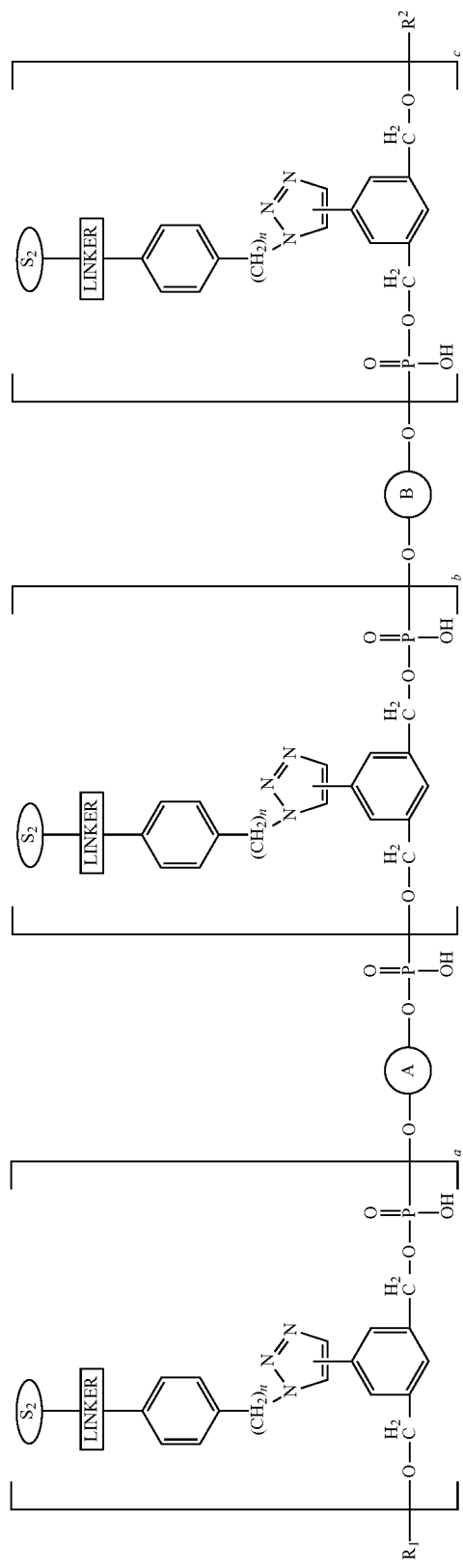

or a peptide chain (ε) having an amino acid sequence of RGD at its end.

14. The oligonucleotide derivative according to claim 13, wherein the modified or unmodified oligonucleotides have a partial structure —(CH$_2$)n-, where n is a natural number of 1 or greater.

15. The oligonucleotide derivative according to claim 13, wherein R$^1$ and R$^2$ are H.

16. The oligonucleotide derivative according to claim 13, wherein b is 0.

17. The oligonucleotide derivative according to claim 13, wherein a and b are both 0.

18. The oligonucleotide derivative according to claim 13, wherein c is 1 or more and 5 or less.

19. The oligonucleotide derivative according to claim 13, wherein the combined chain length of A and B is 10 or more and 35 or less.

20. The oligonucleotide derivative according to claim 13, wherein A and B are oligoribonucleotides.

21. An oligonucleotide construct for regulating gene expression, comprising the oligonucleotide derivative according to claim 13, wherein the construct is selected from single- and double-stranded DNAs, single- and double-stranded RNAs, DNA/RNA chimeras, and DNA/RNA hybrids.

22. The construct according to claim 21, being selected from anti-genes, antisenses, aptamers, siRNAs, miRNAs, shRNAs, and ribozymes.

23. The construct according to claim 21, which has a unit represented by the following formula (4) or (5) at a dangling end (wherein S$_1$ is a substituent represented by the following (α), letters "LINKER" surrounded by a rectangular frame represent a linker, S$_2$ is a substituent represented by the following (β), (γ), (δ), or (ε) bound to an end of the linker (two or more S$_2$s may be bound to the linker), and n represents a natural number of 0 to 4),

[Chemical Formula 3]

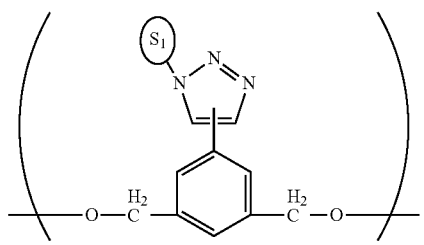

(4)

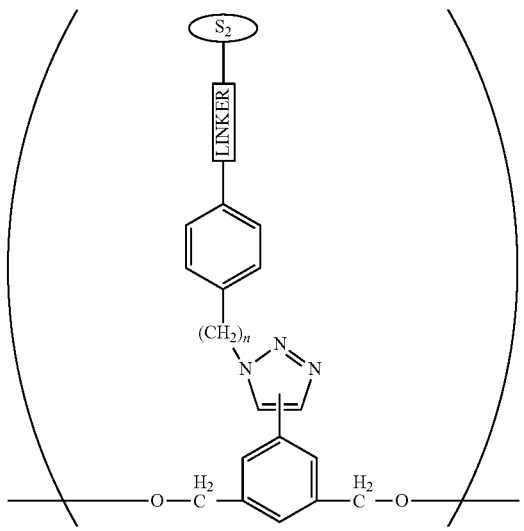

(5)

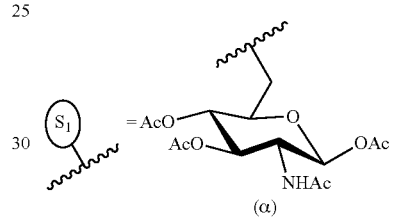

(α)

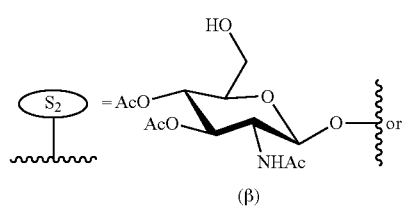

(β)

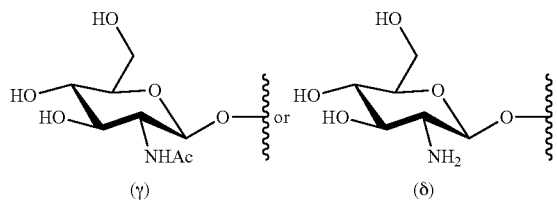

(γ)    (δ)

or a peptide chain (ε) having an amino acid sequence of RGD at its end.

24. The construct according to claim 23, being a siRNA wherein in the oligonucleotide derivative, a and b are 0, c is 1 or 2, and a unit represented by the following formula (4) or (5) is contained at a 3' dangling end (wherein S$_1$ is a substituent represented by the following (α), letters "LINKER" surrounded by a rectangular frame represent a linker, S$_2$ is a substituent represented by the following (β), (γ), (δ), or (ε) bound to an end of the linker (two or more S$_2$s may be bound to the linker), and n represents a natural number of 0 to 4),

[Chemical Formula 4]

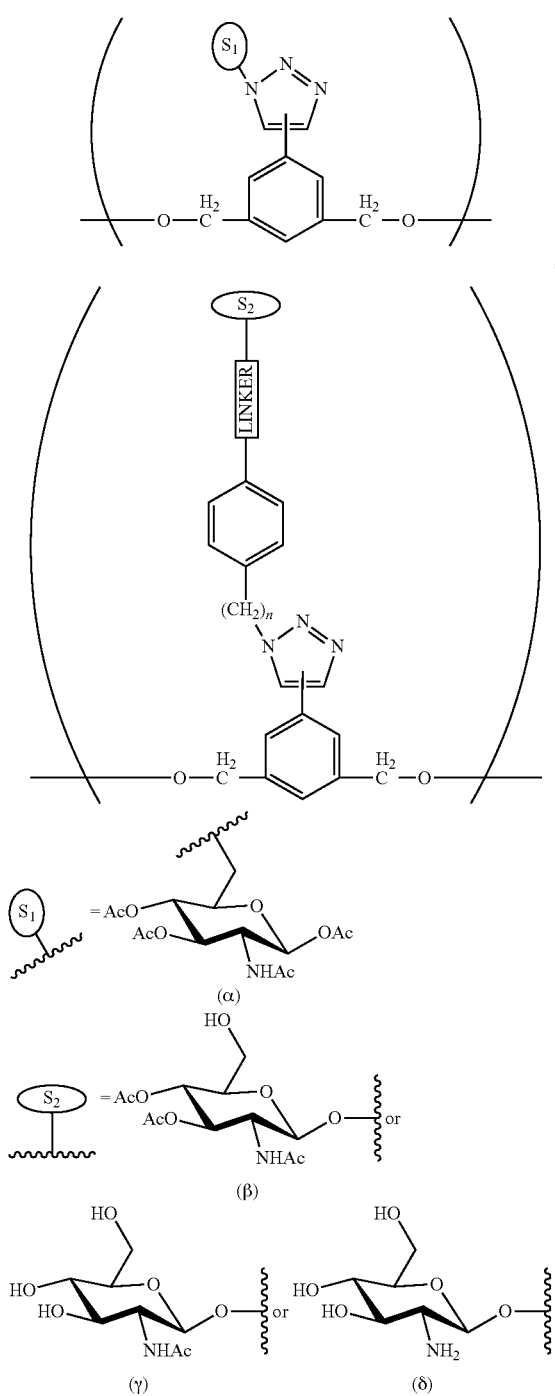

or a peptide chain (ε) having an amino acid sequence of RGD at its end.

25. A method for producing an oligonucleotide derivative, comprising performing a click reaction of compound (6) or (7) with an oligonucleotide having an ethynyl group to produce an oligonucleotide derivative comprising at least one unit represented by the following formula (4) or (5) (wherein $S_1$ is a substituent represented by the following (α), letters "LINKER" surrounded by a rectangular frame represent a linker, $S_2$ is a substituent represented by the following (β), (γ), (δ), or (ε) bound to an end of the linker (two or more $S_2$s may be bound to the linker), and n represents a natural number of 0 to 4),

[Chemical Formula 6]

[Chemical Formula 5]

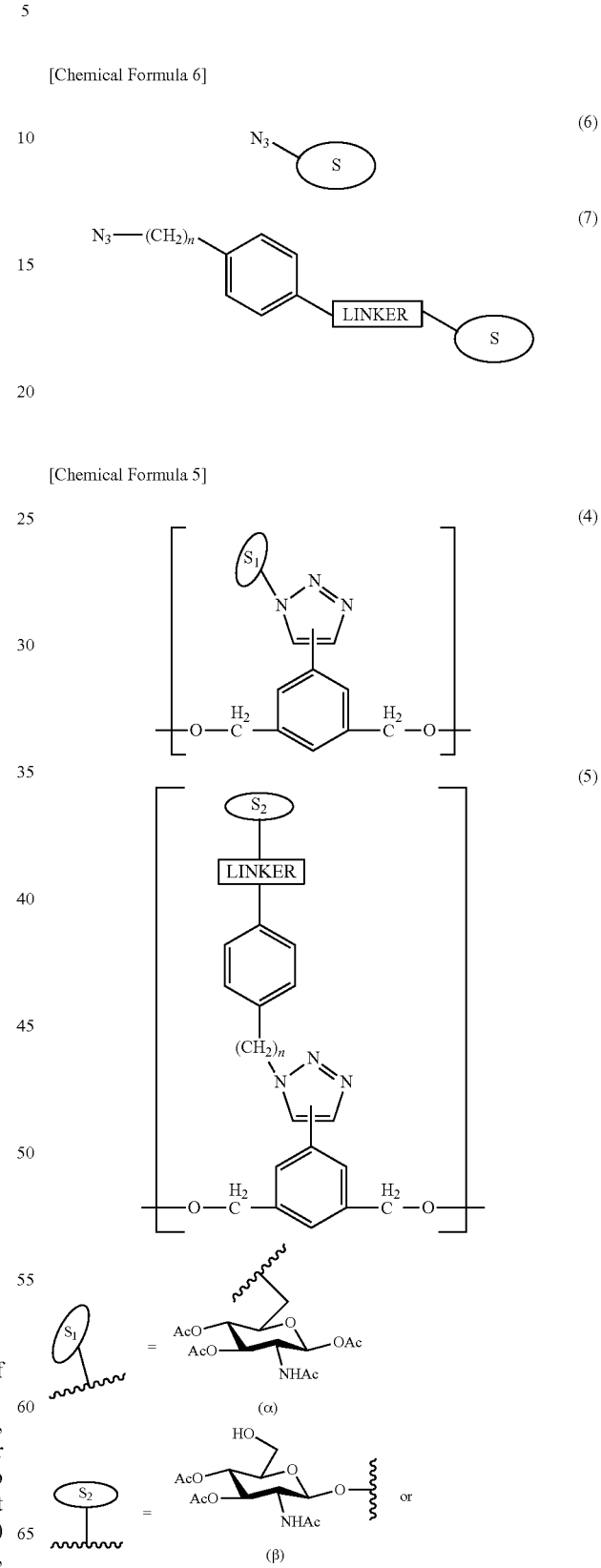

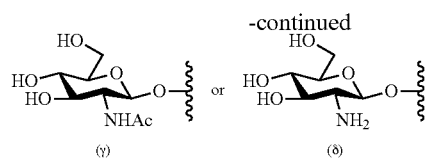
or a peptide chain (ε) having an amino acid sequence of RGD at its end.
* * * * *